US010457641B2

(12) United States Patent
Qian et al.

(10) Patent No.: US 10,457,641 B2
(45) Date of Patent: Oct. 29, 2019

(54) CERTAIN CHEMICAL ENTITIES, COMPOSITIONS, AND METHODS

(71) Applicant: NEUPHARMA, INC., Foster City, CA (US)

(72) Inventors: Xiangping Qian, Foster City, CA (US); Yong-Liang Zhu, Fremont, CA (US)

(73) Assignee: NEUPHARMA, INC., Foster City, CA (US)

( * ) Notice: Subject to any disclaimer, the term of this patent is extended or adjusted under 35 U.S.C. 154(b) by 0 days.

(21) Appl. No.: 15/599,339

(22) Filed: May 18, 2017

(65) Prior Publication Data
US 2017/0334859 A1 Nov. 23, 2017

Related U.S. Application Data

(63) Continuation of application No. 14/430,890, filed as application No. PCT/US2013/061464 on Sep. 24, 2013, now Pat. No. 9,688,635.

(60) Provisional application No. 61/705,037, filed on Sep. 24, 2012.

(51) Int. Cl.
| *A61K 31/47* | (2006.01) |
| *C07D 215/14* | (2006.01) |
| *A61K 45/06* | (2006.01) |
| *C07D 239/74* | (2006.01) |
| *A61J 1/03* | (2006.01) |
| *A61J 1/05* | (2006.01) |
| *A61K 31/517* | (2006.01) |

(52) U.S. Cl.
CPC .............. *C07D 215/14* (2013.01); *A61J 1/03* (2013.01); *A61J 1/05* (2013.01); *A61K 31/47* (2013.01); *A61K 31/517* (2013.01); *A61K 45/06* (2013.01); *C07D 239/74* (2013.01)

(58) Field of Classification Search
CPC ....... A61K 31/47; A61K 31/517; A61K 45/06
See application file for complete search history.

(56) References Cited

U.S. PATENT DOCUMENTS

| 4,464,533 | A | 8/1984 | Krass et al. |
| 4,761,172 | A | 8/1988 | Jahn et al. |
| 5,033,252 | A | 7/1991 | Carter |
| 5,052,558 | A | 10/1991 | Carter |
| 5,323,907 | A | 6/1994 | Kalvelage |
| 5,846,514 | A | 12/1998 | Foster et al. |
| 6,334,997 | B1 | 1/2002 | Foster et al. |
| 6,348,461 | B1 | 2/2002 | Takano et al. |
| 7,691,866 | B2 | 4/2010 | Ramurthy et al. |
| 8,071,616 | B2 | 12/2011 | Dumas et al. |
| 8,198,273 | B2 | 6/2012 | Ibrahim et al. |
| 9,249,110 | B2 | 2/2016 | Qian et al. |
| 9,249,111 | B2 | 2/2016 | Qian et al. |
| 9,295,671 | B2 | 3/2016 | Zhu et al. |
| 9,518,029 | B2 | 12/2016 | Qian et al. |
| 9,572,808 | B2 | 2/2017 | Zhu et al. |
| 9,670,180 | B2 | 6/2017 | Zhu et al. |
| 9,688,635 | B2 * | 6/2017 | Qian ...................... A61K 31/47 |
| 9,725,421 | B2 | 8/2017 | Xiangping et al. |
| 9,908,866 | B2 | 3/2018 | Zhu et al. |
| 10,047,059 | B2 | 8/2018 | Qian et al. |
| 10,065,932 | B2 | 9/2018 | Qian et al. |
| 10,137,125 | B2 | 11/2018 | Zhu et al. |
| 2004/0143117 | A1 | 7/2004 | Barnett et al. |
| 2005/0084835 | A1 | 4/2005 | Lau et al. |
| 2005/0085482 | A1 | 4/2005 | Ramurthy et al. |
| 2007/0232620 | A1 | 10/2007 | Dorsch et al. |
| 2008/0167338 | A1 | 7/2008 | Spevak et al. |
| 2008/0207616 | A1 | 8/2008 | Aquila et al. |
| 2009/0105474 | A1 | 4/2009 | Yokotani et al. |
| 2009/0131461 | A1 | 5/2009 | Davidson et al. |
| 2009/0306087 | A1 | 12/2009 | Ibrahim et al. |
| 2009/0317359 | A1 | 12/2009 | Ramurthy et al. |
| 2010/0190777 | A1 | 7/2010 | Wu et al. |
| 2010/0197688 | A1 | 8/2010 | Nantermet et al. |
| 2010/0286142 | A1 | 11/2010 | Ibrahim et al. |
| 2011/0059954 | A1 | 3/2011 | Gottschling et al. |
| 2011/0172245 | A1 | 7/2011 | Hirose et al. |
| 2012/0122860 | A1 | 5/2012 | Visor et al. |
| 2012/0245174 | A1 | 9/2012 | Ibrahim et al. |
| 2013/0053384 | A1 | 2/2013 | Zhu et al. |
| 2013/0237531 | A1 | 9/2013 | Wu et al. |
| 2013/0267525 | A1 | 10/2013 | Saxty et al. |
| 2014/0038948 | A1 | 2/2014 | Wu et al. |
| 2014/0343068 | A1 | 11/2014 | Qian et al. |
| 2015/0057276 | A1 | 2/2015 | Qian et al. |
| 2015/0057277 | A1 | 2/2015 | Zhu et al. |
| 2015/0158826 | A1 | 6/2015 | Qian et al. |
| 2015/0246885 | A1 | 9/2015 | Qian et al. |

(Continued)

FOREIGN PATENT DOCUMENTS

| CN | 101808994 A | 8/2010 |
| GB | 2189238 A | 10/1987 |

(Continued)

OTHER PUBLICATIONS

Ansel, et al. Pharmaceutical Dosage Forms and Drug Delivery Systems. Seventh Edition, Lippincott Williams & Wilkins, 1999.
Bollag, et al. Clinical efficacy of a RAF inhibitor needs broad target bloackade in BRAF-mutant melanoma. Nature. 2010; 467(7315):596-599.
Buchstaller, et al. Design and synthesis of isoquinolines and benzimidazoles as RAF kinase inhibitors. Bioorganic and Medicinal Chemistry Letters. 2011; 21(8):2264-2269.
Choi, et al. New diarylureas and diarylamides containing 1,3,4-triarylpyrazole scaffold: Synthesis, antiproliferative evaluation against melanoma cell lines, ERK kinase inhibition, and molecular docking studies. Eur J Med Chem. Dec. 2011;46(12):5754-62. doi: 10.1016/j.ejmech.2011.08.013. Epub Aug. 12, 2011.

(Continued)

*Primary Examiner* — Pancham Bakshi
(74) *Attorney, Agent, or Firm* — Wilson Sonsini Goodrich & Rosati

(57) ABSTRACT

Chemical entities that are kinase inhibitors, pharmaceutical compositions and methods of treatment of cancer are described.

22 Claims, No Drawings

(56) References Cited

U.S. PATENT DOCUMENTS

| | | | |
|---|---|---|---|
| 2016/0303118 | A1 | 10/2016 | Zhu et al. |
| 2017/0050938 | A1 | 2/2017 | Qian et al. |
| 2017/0183316 | A1 | 6/2017 | Qian et al. |
| 2018/0230128 | A1 | 8/2018 | Zhu et al. |

FOREIGN PATENT DOCUMENTS

| | | | | |
|---|---|---|---|---|
| JP | 2004513134 | A | 4/2004 | |
| JP | 2006512356 | A | 4/2006 | |
| JP | 2007509059 | A | 4/2007 | |
| JP | 2008516939 | A | 5/2008 | |
| JP | 2008546797 | A | 12/2008 | |
| JP | 2010533729 | A | 10/2010 | |
| JP | 2014530915 | A | 11/2014 | |
| WO | WO-9519169 | A2 | 7/1995 | |
| WO | WO-9722596 | A1 | 6/1997 | |
| WO | WO-9730035 | A1 | 8/1997 | |
| WO | WO-9732856 | A1 | 9/1997 | |
| WO | WO-9813354 | A1 | 4/1998 | |
| WO | WO-9902166 | A1 | 1/1999 | |
| WO | WO-0040529 | A1 | 7/2000 | |
| WO | WO-0041669 | A2 | 7/2000 | |
| WO | WO-0047212 | A1 | 8/2000 | |
| WO | WO-0041669 | A3 | 11/2000 | |
| WO | WO-0192224 | A1 | 12/2001 | |
| WO | WO-0194341 | A1 | 12/2001 | |
| WO | WO-0204434 | A1 | 1/2002 | |
| WO | WO-0208213 | A1 | 1/2002 | |
| WO | WO-0236734 | A2 | 5/2002 | |
| WO | WO-2004056830 | A1 | 7/2004 | |
| WO | WO-2005037285 | A1 | 4/2005 | |
| WO | WO-2007002325 | A1 | 1/2007 | |
| WO | WO-2007044729 | A2 | 4/2007 | |
| WO | WO-2009012283 | A1 | 1/2009 | |
| WO | WO-2009025358 | A1 | 2/2009 | |
| WO | WO-2009077766 | A1 | 6/2009 | |
| WO | WO-2009117080 | A1 | 9/2009 | |
| WO | WO-2009152087 | A1 | 12/2009 | |
| WO | WO-2010075197 | A1 | 7/2010 | |
| WO | WO-2010111527 | A1 | 9/2010 | |
| WO | WO-2010129567 | A1 | 11/2010 | |
| WO | WO-2010129570 | A1 | 11/2010 | |
| WO | WO-2011025938 | A2 | 3/2011 | |
| WO | WO-2011068187 | A1 | 6/2011 | |
| WO | WO-2011147764 | A1 | 12/2011 | |
| WO | WO-2012073017 | A1 | 6/2012 | |
| WO | WO-2012103810 | A1 | 8/2012 | |
| WO | WO2012/118492 | A1 * | 9/2012 | ........... A61K 31/517 |
| WO | WO-2012118492 | A1 | 9/2012 | |
| WO | WO-2013032951 | A1 | 3/2013 | |
| WO | WO-2013040515 | A1 | 3/2013 | |
| WO | WO-2013043935 | A1 | 3/2013 | |
| WO | WO-2013049701 | A1 | 4/2013 | |
| WO | WO-2013112950 | A2 | 8/2013 | |

OTHER PUBLICATIONS

Co-pending U.S. Appl. No. 14/967,124, filed Dec. 11, 2015.
Co-pending U.S. Appl. No. 14/973,438, filed Dec. 17, 2015.
Co-pending U.S. Appl. No. 15/224,422, filed Jul. 29, 2016.
Co-pending U.S. Appl. No. 15/400,720, filed Jan. 6, 2017.
Co-pending U.S. Appl. No. 15/489,679, filed Apr. 17, 2017.
Co-pending U.S. Appl. No. 15/617,505, filed Jun. 8, 2017.
European Office Action dated Mar. 10, 2017 for EP Application No. 13852971.4.
European search report and opinion dated Jan. 29, 2016 for EP Application No. 13838131.
European search report and opinion dated Mar. 21, 2016 for EP Application No. 13740892.
European search report and opinion dated Apr. 21, 2016 for EP Application No. 13852971.4.
European search report and written opinion dated Jan. 30, 2015 for EP Application No. 12833985.0.
European search report and written opinion dated Feb. 20, 2015 for EP Application No. 12831538.9.
European search report and written opinion dated Dec. 15, 2014 for EP Application No. 12828679.6.
Evans. Synthesis of radiolabeled compounds, J. Radioanal. Chem. 1981; 64(1-2):9-32.
Greene, et al. Protective Groups in Organic Synthesis. John Wiley & Sons, 1991.
Hackam, et al. Translation of research evidence from animals to humans. JAMA. Oct. 11, 2006;296(14):1731-2.
Higuchi, et al. Pro-drugs as novel drug delivery systems. American Chemical Society. ACS symposium series 14. 1975.
Hoover, J. Remington's Pharmaceutical Sciences. Mack Publishing Company, 1990.
International search report and written opinion dated Jan. 23, 2013 for PCT/US2012/058095.
International search report and written opinion dated Feb. 7, 2014 for PCT/US2013/061464.
International search report and written opinion dated Mar. 10, 2014 for PCT/US2013/069699.
International search report and written opinion dated Mar. 22, 2013 for PCT/US2013/023313.
International search report and written opinion dated Oct. 23, 2012 for PCT/US2012/052390.
International search report and written opinion dated Nov. 21, 2012 for PCT/US2012/056432.
International search report and written opinion dated Dec. 10, 2012 for PCT/US2012/055653.
Jordan. Tamoxifen: a most unlikely pioneering medicine. Nat Rev Drug Discov. Mar. 2003;2(3):205-13.
Kraska, et al. Disazo condensation pigments, derivatives of quinoxaline. Polish Journal of Chemistry. 1978; 52(9):1665-74.
Liberman, et al. Pharmaceutical Dosage Forms. Marcel Decker, New York, 1980.
Lombardo, et al. Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.
Mossman. Rapid colorimetric assay for cellular growth and survival: application to proliferation and cytotoxicity assays. J Immunol Methods. Dec. 16, 1983;65(1-2):55-63.
Notice of Allowance dated Feb. 10, 2017 and Jan. 26, 2017 for U.S. Appl. No. 14/374,216.
Notice of Allowance dated Mar. 1, 2017 for U.S. Appl. No. 14/430,890.
Notice of Allowance dated Apr. 27, 2017 for U.S. Appl. No. 14/374,216.
Notice of Allowance dated May 4, 2017 for U.S. Appl. No. 14/430,890.
Notice of Allowance dated May 19, 2017 for U.S. Appl. No. 14/442,084.
Notice of Allowance dated Aug. 16, 2017 for U.S. Appl. No. 15/343,935.
"Notice of allowance dated Sep. 28, 2015 for U.S. Appl. No. 14/346,692."
Notice of allowance dated Oct. 12, 2016 for U.S. Appl. No. 14/344,709.
"Notice of allowance dated Oct. 23, 2015 for U.S. Appl. No. 14/346,696."
Notice of Allowance dated Jan. 10, 2017 for U.S. Appl. No. 14/973,492.
Notice of Allowance dated Nov. 2, 2016 for U.S. Appl. No. 14/344,709.
"Notice of allowance dated Nov. 23, 2015 for U.S. Appl. No. 13/594,634."
Notice of Allowance dated Nov. 9, 2016 for U.S. Appl. No. 14/973,492.
Office Action dated Feb. 10, 2017 for U.S. Appl. No. 14/442,084.
Office action dated Mar. 27, 2014 for U.S. Appl. No. 13/594,634.
Office action dated Apr. 12, 2016 for U.S. Appl. No. 14/430,890.
Office action dated Apr. 13, 2015 for U.S. Appl. No. 14/346,692.
Office action dated Apr. 29, 2015 for U.S. Appl. No. 13/594,634.

(56) References Cited

OTHER PUBLICATIONS

Office Action dated May 1, 2017 for U.S. Appl. No. 15/343,935.
Office action dated May 12, 2016 for U.S. Appl. No. 14/344,709.
Office action dated Jun. 11, 2015 for U.S. Appl. No. 14/346,696.
Office action dated Jul. 25, 2016 for U.S. Appl. No. 14/374,216.
"Office action dated Aug. 27, 2015 for U.S. Appl. No. 14/346,692."
Office action dated Aug. 29, 2016 for U.S. Appl. No. 14/430,890.
Office action dated Sep. 22, 2014 for U.S. Appl. No. 13/594,634.
Office action dated Oct. 26, 2016 for U.S. Appl. No. 14/442,084.
Office action dated Dec. 5, 2014 for U.S. Appl. No. 14/346,696.
Remington. The Science and Practice of Pharmacy. Mack Publishing Company, 19th Edition, 1995.
RN 439126-39-3. Chemical Library File Registry. Entered STN: Jul. 17, 2002.
Stem, et al. Overview of monoclonal antibodies in cancer therapy: present and promise. Crit Rev Oncol Hematol. Apr. 2005;54(1):11-29.
Tsai, et al. Discovery of a selective inhibitor of oncogenic B-Raf kinase with potent antimelanoma activity. PNAS. 2008; 105(8):3041-3046.
U.S. Appl. No. 14/344,709, filed Mar. 13, 2014.
U.S. Appl. No. 14/430,890, filed Mar. 24, 2015.
U.S. Appl. No. 14/442,084, filed May 11, 2015.
Zambon, et al. Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Co-pending U.S. Appl. No. 15/785,146, filed Oct. 16, 2017.
Co-pending U.S. Appl. No. 15/875,751, filed Jan. 19, 2018.
European search report with written opinion dated Mar. 13, 2018 for EP Application No. 17195141.
Notice of allowance dated Apr. 20, 2018 for U.S. Appl. No. 14/617,505.
Notice of Allowance dated Oct. 23, 2017 for U.S. Appl. No. 15/489,679.
Office Action dated Jan. 19, 2018 for U.S. Appl. No. 15/617,505.
Office action dated Feb. 16, 2018 for U.S. Appl. No. 15/785,146.
Office action dated Mar. 8, 2018 for U.S. Appl. No. 15/400,720.
Notice of allowance dated Jun. 6, 2018 for U.S. Appl. No. 15/785,146.
Notice of allowance dated Jul. 19, 2018 for U.S. Appl. No. 15/400,720.
Notice of allowance dated Oct. 26, 2018 for U.S. Appl. No. 15/400,720.
Office action dated Dec. 14, 2018 for U.S. Appl. No. 15/875,751.

\* cited by examiner

CERTAIN CHEMICAL ENTITIES, COMPOSITIONS, AND METHODS

CROSS-REFERENCE

This application is a continuation of U.S. Utility application Ser. No. 14/430,890 filed Mar. 24, 2015, now U.S. Pat. No. 9,688,635, which is a National Phase Application under 35 U.S.C. § 371 of PCT/US2013/061464, filed Sep. 24, 2013, which claims the benefit of U.S. Provisional Application Ser. No. 61/705,037, filed on Sep. 24, 2012, each of which application is incorporated herein by reference in its entirety.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

The identification of effective small compounds which specifically inhibit signal transduction and cellular proliferation by modulating the activity of tyrosine and serine/threonine kinases to regulate and modulate abnormal or inappropriate cell proliferation, differentiation, or metabolism is therefore desirable. In particular, the identification of compounds that specifically inhibit the function of a kinase which is essential for processes leading to cancer would be beneficial.

SUMMARY OF THE INVENTION

In one aspect, provided is a compound of Formula I

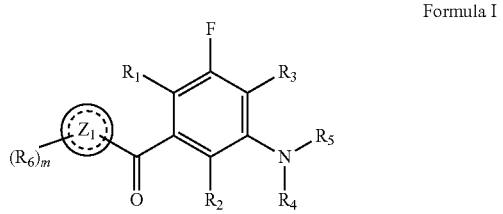

Formula I or a pharmaceutically acceptable salt thereof, wherein
$Z_1$ is optionally substituted heteroaryl;
$R_1$, $R_2$, and $R_3$ are independently hydrogen, cyano, halo, hydroxy, azido, nitro, carboxy, sulfinyl, sulfanyl, sulfonyl, optionally substituted alkoxy, optionally substituted aryloxy, optionally substituted heteroaryloxy, optionally substituted heterocycloalkyloxy, optionally substituted alkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl;
$R_4$ is hydrogen, optionally substituted alkyl, optionally substituted cycloalkyl, optionally substituted heterocycloalkyl, optionally substituted aryl, or optionally substituted heteroaryl;
$R_5$ is hydroxyl, formyl, optionally substituted alkoxy, optionally substituted alkyl, optionally substituted cycloalkyl, optionally substituted heterocycloalkyl, optionally substituted aryl, optionally substituted heteroaryl, —COR$_7$, —CO$_2$R$_7$, —CONR$_7$R$_8$, —C(NR$_9$)NR$_7$R$_8$, —C(NCN)NR$_7$R$_8$, —SO$_2$R$_7$, or —SO$_2$NR$_7$R$_8$, where R$_7$ is optionally substituted alkyl, optionally substituted cycloalkyl, optionally substituted heterocycloalkyl, optionally substituted aryl, or optionally substituted heteroaryl; and R$_8$ and R$_9$ are independently hydrogen, optionally substituted alkyl, optionally substituted cycloalkyl, optionally substituted heterocycloalkyl, optionally substituted aryl, or optionally substituted heteroaryl; or R$_7$ and R$_8$ may be joined together with any intervening atoms to form an optionally substituted heterocycloalkyl ring;
or $R_4$ and $R_5$ may be joined together with any intervening atoms to form an optionally substituted heterocycloalkyl ring;
for each occurrence, $R_6$ is independently hydrogen, cyano, halo, hydroxy, carboxy, azido, nitro, sulfonyl, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, or optionally substituted carbaminodoyl; and
m is 0, 1, 2, 3, 4, 5 or 6;
provided that $Z_1$ is not quinoxalin-6-yl.

In another aspect, the present disclosure provides a pharmaceutical composition comprising a pharmaceutically acceptable carrier and a compound or pharmaceutically acceptable salt of any one of compounds described herein. The pharmaceutical composition may be formulated in a form which is a tablet, capsule, powder, liquid, suspension, suppository, or aerosol. The pharmaceutical composition may be packaged with instructions for using the composition to treat a subject suffering from cancer.

In another aspect, the present disclosure provides a method of treating cancer in a subject which comprises administering to a subject in need thereof a therapeutically effective amount of a compound or pharmaceutically acceptable salt of any one of the compounds described herein. The cancer may be colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In a further embodiment, the cancer is melanoma, non-small cell lung cancer, thyroid cancer, ovarian cancer, or colon cancer. The melanoma may be unresectable or metastatic melanoma.

In another aspect, the present disclosure provides a method of treating a disorder mediated by Raf in a subject in need thereof, comprising administering to the subject a therapeutically effective amount of a compound or pharmaceutically acceptable salt of any one of the compounds described herein.

In another aspect, the present disclosure provides a method of treating a disorder in a subject in need thereof, comprising: a) determining the presence or absence of a B-Raf (BRAF) mutation in a biological sample isolated from the subject; and b) if a BRAF mutation is determined to be present in the subject, administering to the subject a therapeutically effective amount of a compound or pharmaceutically acceptable salt of any one of the compounds described herein.

The BRAF mutation may be V600E or may be in codon 600. In some embodiments, determining the presence of absence of the BRAF mutation comprises amplifying B-raf nucleic acid from the biological sample and sequencing the amplified nucleic acid. In some other embodiments, determining the presence of absence of the BRAF mutation comprises detecting a mutant B-raf polypeptide in the biological sample using a binding agent to a mutant B-raf polypeptide. The binding agent may be an antibody. The biological sample may be isolated from a tumor of the subject.

In another aspect, the present disclosure provides a method of treating a disorder mediated by KDR in a subject in need thereof, comprising administering to the subject a therapeutically effective amount of a compound or pharmaceutically acceptable salt of any one of the compounds described herein.

In some embodiments, the disorder is cancer. The cancer may be colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In a further embodiment, the cancer is melanoma, non-small cell lung cancer, thyroid cancer, ovarian cancer, or colon cancer. The melanoma may be unresectable or metastatic melanoma.

The treatment method described herein may further comprise administering an additional anti-cancer and/or cytotoxic agent.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION OF THE INVENTION

As used herein, the following words and phrases are generally intended to have the meanings as set forth below, except to the extent that the context in which they are used indicates otherwise.

The following abbreviations and terms have the indicated meanings throughout:
AcOH=acetic acid
Boc=tert-butoxycarbonyl
c-=cyclo
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
i-=iso
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram min=minute
mL=milliliter
mmol=millimole
n-=normal
NaOAc=sodium acetate
PE=petroleum ether
Ph=phenyl
Prep=preparative
quant.=quantitative
RP-HPLC=reverse phase-high pressure liquid chromatography
rt or RT=room temperature
s-=sec-=secondary
t-=tert-=tertiary
THF=tetrahydrofuran
TLC=thin layer chromatography
UV=ultraviolet As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —CONH$_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

As used herein, "formyl" refers to the group —C(O)H.

As used herein, "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

As used herein, "azido" refers to the group —$N_3$.

As used herein, "amino" refers to the group —$NH_2$.

As used herein, "mono- and di-(alkyl)amino" refers to secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" refers to the group —CONR$^b$R$^c$, where

R$^b$ is H, optionally substituted $C_1$-$C_6$ alkyl, optionally substituted cycloalkyl, optionally substituted heterocycloalkyl, optionally substituted aryl, optionally substituted heteroaryl, or optionally substituted alkoxy; and R$^c$ is hydrogen or optionally substituted $C_1$-$C_4$ alkyl; or R$^b$ and R$^c$ taken together with the nitrogen to which they are bound, form an optionally substituted 4- to 8-membered nitrogen-containing heterocycloalkyl which optionally includes 1 or 2 additional heteroatoms chosen from O, N, and S in the heterocycloalkyl ring;

where each substituted group is independently substituted with one or more substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), or —$NHSO_2$($C_1$-$C_4$ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.

As used herein, "aralkyl" refers to the group -alkyl-aryl.

As used herein, "carbamimidoyl" refers to the group —C(=NH)—$NH_2$.

As used herein, "substituted carbamimidoyl" refers to the group —C(=$NR^e$)—$NR^fR^g$ where $R^e$ is hydrogen, cyano, optionally substituted alkyl, optionally substituted cycloalkyl, optionally substituted aryl, optionally substituted heteroaryl, or optionally substituted heterocycloalkyl; and $R^f$ and $R^g$ are independently hydrogen optionally substituted alkyl, optionally substituted cycloalkyl, optionally substituted aryl, optionally substituted heteroaryl, or optionally substituted heterocycloalkyl, provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —OP(O)(O$R^b$)O$R^c$, sulfanyl (such as $SR^b$), sulfinyl (such as —$SOR^a$), or sulfonyl (such as —$SO_2R^a$ and —$SO_2NR^bR^c$), where $R^a$ is optionally substituted C1-C6 alkyl, optionally substituted aryl, or optionally substituted heteroaryl;

$R^b$ is H, optionally substituted C1-C6 alkyl, optionally substituted aryl, or optionally substituted heteroaryl; and $R^c$ is hydrogen or optionally substituted C1-C4 alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO2($C_1$-$C_4$ alkyl), —$SO_2$(phenyl), —$SO_2$($C_1$-$C_4$ haloalkyl), —$SO_2NH_2$, —$SO_2$NH($C_1$-$C_4$—$SO_2$NH(phenyl), —$NHSO_2$($C_1$-$C_4$ alkyl), —$NHSO_2$(phenyl), or —$NHSO_2$($C_1$-$C_4$ haloalkyl).

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoro ethyl.

As used herein, "heteroaryl" refers to:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 4- to 8-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein.

Substituted heteroaryl also includes ring systems substituted with one or more oxide ($-O^-$) substituents, such as pyridinyl N-oxides.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include but are not limited to, for example, pyrrolidinyl, morpholinyl, piperidinyl, piperazinyl, azetidinyl, diazepanyl, diazocanyl, pyrrolidinyl, morpholinyl, piperidinyl, piperazinyl, imidazolidinyl, pyrazolidinyl, dihydrofuranyl, and tetrahydrofuranyl. Substituted heterocycloalkyl can also include ring systems substituted with one or more oxo (=O) or oxide ($-O^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 7 ring atoms, optionally contains 1-3 heteroatoms independently chosen from oxygen, sulfur, and nitrogen and is not aromatic.

As used herein, "sulfanyl" refers to the groups: —S-(optionally substituted ($C_1$-$C_6$)alkyl), —S-(optionally substituted cycloalkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

As used herein, "sulfanyl" refers to the groups: —S(O)-(optionally substituted ($C_1$-$C_6$)alkyl), —S(O)-(optionally substituted cycloalkyl), —S(O)-(optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S($O_2$)-(optionally substituted ($C_1$-$C_6$)alkyl), —S($O_2$)-(optionally substituted cycloalkyl), —S($O_2$)-(optionally substituted aryl), —S($O_2$)-(optionally substituted heteroaryl), —S($O_2$)-(optionally substituted heterocycloalkyl), and —S($O_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), or sulfonyl (such as —$SO_2R^a$ and —$SO_2NR^bR^c$), where $R^a$ is optionally substituted $C_1$-$C_6$ alkyl, optionally substituted cycloalkyl, optionally substituted heterocycloalkyl, optionally substituted alkenyl, optionally substituted alkynyl, optionally substituted aryl, or optionally substituted heteroaryl; $R^b$ is hydrogen, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl), —$N(C_1$-$C_4$ alkyl)C(O)($C_1$-$C_4$ alkyl), —$N(C_1$-$C_4$ alkyl)C(O)(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), or —$NHSO_2(C_1$-$C_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), or sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$—$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —CON($C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —NHC(O)(phenyl), —$N(C_1$-$C_4$ alkyl)C(O)($C_1$-$C_4$ alkyl), —$N(C_1$-$C_4$ alkyl)C(O)(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), or —$NHSO_2(C_1$-$C_4$ haloalkyl).

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —NHC(O)(phenyl), —$N(C_1$-$C_4$ alkyl)C(O)($C_1$-$C_4$ alkyl), —$N(C_1$-$C_4$ alkyl)C(O)(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$—$SO_2NH$(phenyl), —$NHSO_2(C_1$-$C_4$ alkyl), —$NHSO_2$(phenyl), or —$NHSO_2(C_1$-$C_4$ haloalkyl).

In some embodiments, a substituted alkoxy group is "polyalkoxy" or —O-(optionally substituted alkylene)-(optionally substituted alkoxy), and includes groups such as —$OCH_2CH_2OCH_3$, and residues of glycol ethers such as polyethyleneglycol, and —$O(CH_2CH_2O)_xCH_3$, where x is an integer of 2-20, such as 2-10, and for example, 2-5. Another substituted alkoxy group is hydroxyalkoxy or —$OCH_2(CH_2)_yOH$, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$—SO$_2$NH(phenyl), —NHSO$_2$(C$_1$-C$_4$ alkyl), —NHSO$_2$(phenyl), or —NHSO$_2$(C$_1$-C$_4$ haloalkyl).

As used herein, "substituted amino" refers to the group —NHR$^d$ or —NR$^d$R$^e$ wherein R$^d$ is hydroxyl, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein R$^e$ is chosen from optionally substituted alkyl, optionally substituted cycloalkyl, optionally substituted aryl, optionally substituted heteroaryl, or optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^c$, —OCONR$^b$R$^c$, —OP(O)(OR$^b$)OR$^c$, sulfanyl (such as SR$^b$), sulfinyl (such as —SOR$^a$), or sulfonyl (such as —SO$_2$R$^a$ and —SO$_2$NR$^b$R$^c$), wherein R$^a$ is optionally substituted C$_1$-C$_6$ alkyl, optionally substituted alkenyl, optionally substituted alkynyl, optionally substituted aryl, or optionally substituted heteroaryl;

R$^b$ is H, optionally substituted C$_1$-C$_6$ alkyl, optionally substituted cycloalkyl, optionally substituted heterocycloalkyl, optionally substituted aryl, or optionally substituted heteroaryl; and R$^c$ is hydrogen or optionally substituted C$_1$-C$_4$ alkyl; or R$^b$ and R$^c$, and the nitrogen to which they are attached, form an optionally substituted heterocycloalkyl group; and wherein each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), or —NHSO$_2$(C$_1$-C$_4$ haloalkyl); and wherein optionally substituted acyl, optionally substituted alkoxycarbonyl, sulfinyl and sulfonyl are as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Similarly, "pharmaceutically acceptable forms" of compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the pharmaceutically acceptable salts, as well as mixtures thereof.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates.

Compounds of Formula I also include other pharmaceutically acceptable forms of the recited compounds, including chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, pharmaceutically acceptable salts include "non-covalent complexes" of pharmaceutically acceptable salts.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

The compounds disclosed herein can be used in different enriched isotopic forms, e.g., enriched in the content of $^2H$, $^3H$, $^{11}C$, $^{13}C$ and/or $^{14}C$. In one particular embodiment, the compound is deuterated at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

As used herein, the terms "group", "radical" or "fragment" are synonymous and are intended to indicate functional groups or fragments of molecules attachable to a bond or other fragments of molecules.

As used herein, the term "leaving group" refers to the meaning conventionally associated with it in synthetic organic chemistry, i.e., an atom or group displaceable under nucleophilic displacement conditions. Examples of leaving groups include, but are not limited to, dimethylhydroxylamino (e.g. Weinreb amide), halogen, alkane- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

As used herein, the term "protective group" or "protecting group" refers to a group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block certain reactive sites present in the reactants. Examples of protecting groups can be found in Wuts et al., *Green's Protective Groups in Organic Synthesis*, (J. Wiley, 4th ed. 2006).

As used herein, the term "deprotection" or "deprotecting" refers to a process by which a protective group is removed after a selective reaction is completed. Certain protective groups may be preferred over others due to their convenience or relative ease of removal. Without being limiting, deprotecting reagents for protected amino or anilino group include strong acid such as trifluoroacetic acid (TFA), concentrated HCl, $H_2SO_4$, or HBr, and the like.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly)

another factor to increase or decrease the target activity, or by (directly or indirectly) increasing or decreasing the amount of target present in the cell or organism.

As used herein, "active agent" is used to indicate a chemical entity which has biological activity. In certain embodiments, an "active agent" is a compound having pharmaceutical utility. For example an active agent may be an anti-cancer therapeutic.

As used herein, "significant" refers to any detectable change that is statistically significant in a standard parametric test of statistical significance such as Student's T-test, where $p<0.05$.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of at least one compound of Formula I, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

As used herein, "subject" refers to a mammal that has been or will be the object of treatment, observation or experiment. The methods described herein can be useful in both human therapy and veterinary applications. In some embodiments, the subject is a human.

The term "mammal" is intended to have its standard meaning, and encompasses humans, dogs, cats, sheep, and cows, for example.

As used herein, the terms "BRAF", "B-raf", "B-Raf" and the like are used interchangeably to refer to the gene or protein product of the gene.

A. Compounds

In one aspect, provided is a compound of Formula I

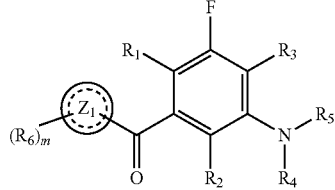

Formula I or a pharmaceutically acceptable salt thereof, wherein
$Z_1$ is optionally substituted heteroaryl;
$R_1$, $R_2$, and $R_3$ are independently hydrogen, cyano, halo, hydroxy, azido, nitro, carboxy, sulfinyl, sulfanyl, sulfonyl, optionally substituted alkoxy, optionally substituted aryloxy, optionally substituted heteroaryloxy, optionally substituted heterocycloalkyloxy, optionally substituted alkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl;

$R_4$ is hydrogen, optionally substituted alkyl, optionally substituted cycloalkyl, optionally substituted heterocycloalkyl, optionally substituted aryl, or optionally substituted heteroaryl;

$R_5$ is hydroxyl, formyl, optionally substituted alkoxy, optionally substituted alkyl, optionally substituted cycloalkyl, optionally substituted heterocycloalkyl, optionally substituted aryl, optionally substituted heteroaryl, —$COR_7$, —$CO_2R_7$, —$CONR_7R_8$, —$C(NR_9)NR_7R_8$, —$C(NCN)NR_7R_8$, —$SO_2R_7$, or —$SO_2NR_7R_8$, where $R_7$ is optionally substituted alkyl, optionally substituted cycloalkyl, optionally substituted heterocycloalkyl, optionally substituted aryl, or optionally substituted heteroaryl; and $R_8$ and $R_9$ are independently hydrogen, optionally substituted alkyl, optionally substituted cycloalkyl, optionally substituted heterocycloalkyl, optionally substituted aryl, or optionally substituted heteroaryl; or $R_7$ and $R_8$ may be joined together with any intervening atoms to form an optionally substituted heterocycloalkyl ring;

or $R_4$ and $R_5$ may be joined together with any intervening atoms to form an optionally substituted heterocycloalkyl ring;

for each occurrence, $R_6$ is independently hydrogen, cyano, halo, hydroxy, carboxy, azido, nitro, sulfonyl, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, or optionally substituted carbaminodoyl; and m is 0, 1, 2, 3, 4, 5 or 6;
provided that $Z_1$ is not quinoxalin-6-yl.

In some embodiments, $R_1$, $R_2$, and $R_3$ are independently hydrogen, cyano, or halo. In some embodiments, $R_1$ and $R_2$ are independently hydrogen or halo. In some embodiments, $R_1$ and $R_2$ are independently hydrogen, fluoro or chloro. In some embodiments, $R_3$ is hydrogen. In some embodiments, $R_1$ and $R_2$ are independently hydrogen, fluoro or chloro, and $R_3$ is hydrogen.

In some embodiments, $R_4$ is hydrogen, optionally substituted alkyl, or optionally substituted cycloalkyl. In some embodiments, $R_4$ is hydrogen or optionally substituted lower alkyl. In some embodiments, $R_4$ is hydrogen.

In some embodiments, $R_5$ is —$COR_7$, —$CO_2R_7$, —$CONR_7R_8$, —$C(NR_9)NR_7R_8$, —$C(NCN)NR_7R_8$, —$SO_2R_7$, or —$SO_2NR_7R_8$. In some embodiments, $R_5$ is —$COR_7$, —$CONR_7R_8$, or —$SO_2R_7$.

In some embodiments, $R_7$ is optionally substituted alkyl, optionally substituted cycloalkyl, optionally substituted heterocycloalkyl, optionally substituted aryl, or optionally substituted heteroaryl. In some embodiments, $R_7$ is lower alkyl, aryl optionally substituted with one or two groups independently halo, cyano, lower alkyl, amino, and lower alkoxy, or heteroaryl optionally substituted with one or two groups independently halo, cyano, lower alkyl, amino, or lower alkoxy. In some embodiments, $R_7$ is propyl, cyclopropyl, phenyl, pyridyl, 5-fluoropyridin-3-yl, 5-chloropyridin-3-yl, 2-(trifluoroethyl)pyridin-4-yl, 3-fluorophenyl, 3-chlorophenyl, 4-fluorophenyl, 4-chlorophenyl, 3,4-di-fluoro-phenyl, 3,5-di-fluoro-phenyl, 3-chloro-4-fluoro-phenyl, 4-chloro-3-fluoro-phenyl, 3-fluoro-4-trifluromethyl-phenyl, 4-fluoro-3-trifluromethyl-phenyl, 3-chloro-4-trifluromethyl-phenyl, or 4-chloro-3-trifluromethyl-phenyl.

In some embodiments, $R_8$ is hydrogen or optionally substituted lower alkyl. In some embodiments, $R_8$ is hydrogen.

In some embodiments, $R_7$ and $R_8$ are joined together with any intervening atoms to form an optionally substituted 4- to 8-membered heterocycloalkyl ring. In some embodiments, $R_7$ and $R_8$ are joined together to form a 4- to 8-membered heterocycloalkyl ring chosen from pyrrolidin-1-yl, morpholin-4-yl (numbered wherein the oxygen is assigned priority 1), piperidin-1-yl, piperazin-1-yl, 1,4-diazepan-1-yl, and 1,4-diazocan-1-yl, each of which is optionally substituted with one or two groups independently hydroxyl, amino, oxo, or lower alkyl optionally substituted with hydroxy or amino.

In some embodiments, $R_9$ is hydrogen, optionally substituted alkyl, or optionally substituted cycloalkyl. In some embodiments, $R_9$ is hydrogen or optionally substituted lower alkyl. In some embodiments, $R_9$ is hydrogen.

In some embodiments, $R_4$ and $R_5$ are joined together with any intervening atoms to form an optionally substituted 4- to 8-membered heterocycloalkyl ring. In some embodiments, $R_4$ and $R_5$ are joined together to form a 4- to 8-membered heterocycloalkyl ring chosen from pyrrolidin-1-yl, morpholin-4-yl, piperidin-1-yl, piperazin-1-yl, 1,4-diazepan-1-yl, and 1,4-diazocan-1-yl, each of which is optionally substituted with one or two groups independently hydroxyl, amino, oxo, or lower alkyl optionally substituted with hydroxy or amino.

In some embodiments, $Z_1$ is 1,5-naphthyridin-2-yl, 1,7-naphthyridin-6-yl, 1H-pyrazolo[3,4-b]pyrazin-3-yl, 1H-pyrazolo[3,4-b]pyridin-3-yl, 5H-pyrrolo[2,3-b]pyrazin-7-yl, 7H-pyrrolo[2,3-c]pyridazin-5-yl, 7H-pyrrolo[2,3-d]pyrimidin-5-yl, benzo[d]oxazol-5-yl, benzo[d]oxazol-6-yl, benzo[d]thiazol-6-yl, oxazolo[5,4-b]pyridin-5-yl, pyrido[3,4-b]pyrazin-7-yl, quinazolin-6-yl, or quinolin-6-yl.

In some embodiments, $R_6$ is hydrogen, cyano, halo, hydroxy, carboxy, optionally substituted alkoxy, optionally substituted aryloxy, optionally substituted alkoxycarbonyl, optionally substituted alkyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or optionally substituted alkynyl. In a further embodiment, $R_6$ is hydrogen, cyano, optionally substituted alkoxy, optionally substituted aryloxy, optionally substituted amino, optionally substituted alkyl, optionally substituted aryl, optionally substituted heterocycloalkyl, or optionally substituted heteroaryl. In another further embodiment, $R_6$ is optionally substituted aryl, optionally substituted heterocycloalkyl, or optionally substituted heteroaryl. In another embodiment, $R_6$ is optionally substituted morpholinyl, optionally substituted piperazinyl, optionally substituted pyrrolidinyl, optionally substituted piperidinyl, optionally substituted imidazolyl, optionally substituted pyrazolyl, or optionally substituted pyridyl. In other embodiments, $R_6$ is pyrrolidin-1-yl, morpholin-4-yl, piperidin-1-yl, piperazin-1-yl, 1,4-diazepan-1-yl, or 1,4-diazocan-1-yl, each of which is optionally substituted with one or two groups independently chosen from hydroxyl, amino, oxo, and lower alkyl optionally substituted with hydroxy or amino. In other embodiments, $R_6$ is hydrogen, cyano, lower alkyl, lower alkoxy, amino, 1H-imidazol-1-yl optionally substituted with lower alkyl, 1H-pyrazol-4-yl optionally substituted with lower alkyl, 1H-pyrazol-3-yl optionally substituted with lower alkyl, pyridin-2-yl optionally substituted with lower alkyl, pyridin-3-yl optionally substituted with lower alkyl, or pyridin-4-yl optionally substituted with lower alkyl. In some embodiments, $R_6$ is hydrogen, methyl, cyano, methoxy, 1H-imidazol-1-yl, 2-methyl-1H-imidazol-1-yl, 5-methyl-1H-imidazol-1-yl, 4-methyl-1H-imidazol-1-yl, 1H-pyrazol-4-yl, 1H-pyrazol-3-yl, pyridin-3-yl, 6-methyl-pyridin-3-yl, pyridin-4-yl, morpholin-4-yl, pyrrolidin-1-yl, or piperazin-1-yl. In other embodiments, $R_6$ is optionally substituted heteroaryl. For example, $R_6$ is 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolyl, 2,4-imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, or 5,6,7,8-tetrahydroisoquinolinyl. In yet other embodiments, $R_6$ is optionally substituted heterocycloalkyl. For example, $R_6$ is pyrrolidinyl such as 2-pyrrolidinyl, imidazolidinyl such as 2,4-imidazolidinyl, pyrazolidinyl such as 2,3-pyrazolidinyl, piperidyl such as 2-piperidyl, 3-piperidyl, or 4-piperidyl, piperazinyl such as 2,5-piperazinyl, pyrrolidinyl, azetidinyl, pyranyl, dihydrofuranyl such as 2,3-dihydrofuranyl, or 2,5-dihydrofuranyl, morpholinyl such as 2-morpholinyl or 3-morpholinyl, piperidinyl N-oxide, morpholinyl-N-oxide, 1-oxo-1-thiomorpholinyl or 1,1-dioxo-1-thiomorpholinyl.

In some embodiments, in is 0, 1, 2 or 3. In some embodiments, wherein m is 0. In some embodiments, in is 1.

In another aspect, the present disclosure provides a compound or pharmaceutically acceptable salt chosen from the group consisting of:

N-(2-chloro-5-fluoro-3-(quinoline-6-carbonyl)phenyl)propane-1-sulfonamide,

N-(2-chloro-5-fluoro-3-(3-methylquinoline-6-carbonyl)phenyl)propane-1-sulfonamide, N-(2-chloro-3-(3-cyanoquinoline-6-carbonyl)-5-fluorophenyl)propane-1-sulfonamide, N-(2-chloro-5-fluoro-3-(3-methoxyquinoline-6-carbonyl)phenyl)propane-1-sulfonamide, N-(2-chloro-3-(3-(4-chlorophenyl)quinoline-6-carbonyl)-5-fluorophenyl)propane-1-sulfonamide, N-(2-chloro-5-fluoro-3-(3-(pyridin-3-yl)quinoline-6-carbonyl)phenyl)propane-1-sulfonamide, N-(2-chloro-5-fluoro-3-(3-morpholinoquinoline-6-carbonyl)phenyl)propane-1-sulfonamide, N-(2-chloro-5-fluoro-3-(3-(piperazin-1-yl)quinoline-6-carbonyl)phenyl)propane-1-sulfonamide, N-(2-chloro-5-fluoro-3-(3-(2-hydroxyethoxy)quinoline-6-carbonyl)phenyl)propane-1-sulfonamide, N-(2-chloro-5-fluoro-3-(quinazoline-6-carbonyl)phenyl)propane-1-sulfonamide, N-(2-chloro-5-fluoro-3-(1,7-naphthyridine-6-carbonyl)phenyl)propane-1-sulfonamide, N-(2-chloro-5-fluoro-3-(pyrido[3,4-b]pyrazine-7-carbonyl)phenyl)propane-1-sulfonamide, N-(2-chloro-5-fluoro-3-(1,5-naphthyridine-2-carbonyl)phenyl)propane-1-sulfonamide, N-(3-(benzo[d]oxazole-6-carbonyl)-2-chloro-5-fluorophenyl)propane-1-sulfonamide,
N-(3-(benzo[d]oxazole-5-carbonyl)-2-chloro-5-fluorophenyl)propane-1-sulfonamide,
N-(2-chloro-5-fluoro-3-(oxazolo[5,4-b]pyridine-5-carbonyl)phenyl)propane-1-sulfonamide,
N-(3-(benzo[d]thiazole-6-carbonyl)-2-chloro-5-fluorophenyl)propane-1-sulfonamide,
N-(2-chloro-3-(3a,7a-dihydro-1H-pyrazolo[3,4-b]pyridine-3-carbonyl)-5-fluorophenyl)propane-1-sulfonamide,
N-(2-chloro-3-(7,7a-dihydro-4aH-pyrrolo[2,3-d]pyrimidine-5-carbonyl)-5-fluorophenyl)propane-1-sulfonamide,
N-(2-chloro-3-(5,7a-dihydro-4aH-pyrrolo[2,3-b]pyrazine-7-carbonyl)-5-fluorophenyl)propane-1-sulfonamide,
N-(2-chloro-3-(3a,7a-dihydro-1H-pyrazolo[3,4-b]pyrazine-3-carbonyl)-5-fluorophenyl)propane-1-sulfonamide,
N-(2-chloro-3-(7,7a-dihydro-4aH-pyrrolo[2,3-c]pyridazine-5-carbonyl)-5-fluorophenyl)propane-1-sulfonamide,
N-(2-chloro-4,5-difluoro-3-(quinoline-6-carbonyl)phenyl)propane-1-sulfonamide,
N-(2-chloro-4,5-difluoro-3-(3-methylquinoline-6-carbonyl)phenyl)propane-1-sulfonamide,
N-(2-chloro-3-(3-cyanoquinoline-6-carbonyl)-4,5-difluorophenyl)propane-1-sulfonamide,
N-(2-chloro-4,5-difluoro-3-(3-methoxyquinoline-6-carbonyl)phenyl)propane-1-sulfonamide,
N-(2-chloro-3-(3-(4-chlorophenyl)quinoline-6-carbonyl)-4,5-difluorophenyl)propane-1-sulfonamide,
N-(2-chloro-4,5-difluoro-3-(3-(pyridin-3-yl)quinoline-6-carbonyl)phenyl)propane-1-sulfonamide,
N-(2-chloro-4,5-difluoro-3-(3-morpholinoquinoline-6-carbonyl)phenyl)propane-1-sulfonamide,
N-(2-chloro-4,5-difluoro-3-(3-(piperazin-1-yl)quinoline-6-carbonyl)phenyl)propane-1-sulfonamide,
N-(2-chloro-4,5-difluoro-3-(3-(2-hydroxyethoxy)quinoline-6-carbonyl)phenyl)propane-1-sulfonamide,
N-(2-chloro-4,5-difluoro-3-(quinazoline-6-carbonyl)phenyl)propane-1-sulfonamide,
N-(2-chloro-4,5-difluoro-3-(1,7-naphthyridine-6-carbonyl)phenyl)propane-1-sulfonamide,
N-(2-chloro-4,5-difluoro-3-(pyrido[3,4-b]pyrazine-7-carbonyl)phenyl)propane-1-sulfonamide, N-(2-chloro-4,5-difluoro-3-(1,5-naphthyridine-2-carbonyl)phenyl)propane-1-sulfonamide,
N-(3-(benzo[d]oxazole-6-carbonyl)-2-chloro-4,5-difluorophenyl)propane-1-sulfonamide,
N-(3-(benzo[d]oxazole-5-carbonyl)-2-chloro-4,5-difluorophenyl)propane-1-sulfonamide,
N-(2-chloro-4,5-difluoro-3-(oxazolo[5,4-b]pyridine-5-carbonyl)phenyl)propane-1-sulfonamide,
N-(3-(benzo[d]thiazole-6-carbonyl)-2-chloro-4,5-difluorophenyl)propane-1-sulfonamide,
N-(2-chloro-3-(3a,7a-dihydro-1H-pyrazolo[3,4-b]pyridine-3-carbonyl)-4,5-difluorophenyl)propane-1-sulfonamide,
N-(2-chloro-3-(7,7a-dihydro-4aH-pyrrolo[2,3-d]pyrimidine-5-carbonyl)-4,5-difluorophenyl)propane-1-sulfonamide,
N-(2-chloro-3-(5,7a-dihydro-4aH-pyrrolo[2,3-b]pyrazine-7-carbonyl)-4,5-difluorophenyl)propane-1-sulfonamide,
N-(2-chloro-3-(3a,7a-dihydro-1H-pyrazolo[3,4-b]pyrazine-3-carbonyl)-4,5-difluorophenyl)propane-1-sulfonamide,
N-(2-chloro-3-(7,7a-dihydro-4aH-pyrrolo[2,3-c]pyridazine-5-carbonyl)-4,5-difluorophenyl)propane-1-sulfonamide,
N-(3-fluoro-5-(quinoline-6-carbonyl)phenyl)propane-1-sulfonamide,
N-(3-fluoro-5-(3-methylquinoline-6-carbonyl)phenyl)propane-1-sulfonamide,
N-(3-(3-cyanoquinoline-6-carbonyl)-5-fluorophenyl)propane-1-sulfonamide,
N-(3-fluoro-5-(3-methoxyquinoline-6-carbonyl)phenyl)propane-1-sulfonamide,
N-(3-(3-(4-chlorophenyl)quinoline-6-carbonyl)-5-fluorophenyl)propane-1-sulfonamide,
N-(3-fluoro-5-(3-(pyridin-3-yl)quinoline-6-carbonyl)phenyl)propane-1-sulfonamide,
N-(3-fluoro-5-(3-morpholinoquinoline-6-carbonyl)phenyl)propane-1-sulfonamide,
N-(3-fluoro-5-(3-(piperazin-1-yl)quinoline-6-carbonyl)phenyl)propane-1-sulfonamide,
N-(3-fluoro-5-(3-(2-hydroxyethoxy)quinoline-6-carbonyl)phenyl)propane-1-sulfonamide,
N-(3-fluoro-5-(quinazoline-6-carbonyl)phenyl)propane-1-sulfonamide,
N-(3-fluoro-5-(1,7-naphthyridine-6-carbonyl)phenyl)propane-1-sulfonamide,
N-(3-fluoro-5-(pyrido[3,4-b]pyrazine-7-carbonyl)phenyl)propane-1-sulfonamide,
N-(3-fluoro-5-(1,5-naphthyridine-2-carbonyl)phenyl)propane-1-sulfonamide,
N-(3-(benzo[d]oxazole-6-carbonyl)-5-fluorophenyl)propane-1-sulfonamide,
N-(3-(benzo[d]oxazole-5-carbonyl)-5-fluorophenyl)propane-1-sulfonamide,
N-(3-fluoro-5-(oxazolo[5,4-b]pyridine-5-carbonyl)phenyl)propane-1-sulfonamide,
N-(3-(benzo[d]thiazole-6-carbonyl)-5-fluorophenyl)propane-1-sulfonamide,
N-(3-(3a,7a-dihydro-1H-pyrazolo[3,4-b]pyridine-3-carbonyl)-5-fluorophenyl)propane-1-sulfonamide,
N-(3-(7,7a-dihydro-4aH-pyrrolo[2,3-d]pyrimidine-5-carbonyl)-5-fluorophenyl)propane-1-sulfonamide,
N-(3-(5,7a-dihydro-4aH-pyrrolo[2,3-b]pyrazine-7-carbonyl)-5-fluorophenyl)propane-1-sulfonamide,
N-(3-(3a,7a-dihydro-1H-pyrazolo[3,4-b]pyrazine-3-carbonyl)-5-fluorophenyl)propane-1-sulfonamide,
N-(3-(7,7a-dihydro-4aH-pyrrolo[2,3-c]pyridazine-5-carbonyl)-5-fluorophenyl)propane-1-sulfonamide,
N-(3-fluoro-5-(3-((2-hydroxyethyl)amino)quinoline-6-carbonyl)phenyl)propane-1-sulfonamide,
N-(3-fluoro-5-(3-(pyrrolidin-1-yl)quinoline-6-carbonyl)phenyl)propane-1-sulfonamide,
N-(3-(3-(1H-imidazol-1-yl)quinoline-6-carbonyl)-5-fluorophenyl)propane-1-sulfonamide,
N-(3-(3-(1H-pyrazol-4-yl)quinoline-6-carbonyl)-5-fluorophenyl)propane-1-sulfonamide,
N-(2,5-difluoro-3-(quinoline-6-carbonyl)phenyl)propane-1-sulfonamide,
N-(2,5-difluoro-3-(3-methylquinoline-6-carbonyl)phenyl)propane-1-sulfonamide,
N-(3-(3-cyanoquinoline-6-carbonyl)-2,5-difluorophenyl)propane-1-sulfonamide,
N-(2,5-difluoro-3-(3-methoxyquinoline-6-carbonyl)phenyl)propane-1-sulfonamide,
N-(3-(3-(4-chlorophenyl)quinoline-6-carbonyl)-2,5-difluorophenyl)propane-1-sulfonamide,
N-(2,5-difluoro-3-(3-(pyridin-3-yl)quinoline-6-carbonyl)phenyl)propane-1-sulfonamide,
N-(2,5-difluoro-3-(3-morpholinoquinoline-6-carbonyl)phenyl)propane-1-sulfonamide,
N-(2,5-difluoro-3-(3-(piperazin-1-yl)quinoline-6-carbonyl)phenyl)propane-1-sulfonamide,
N-(2,5-difluoro-3-(3-(2-hydroxyethoxy)quinoline-6-carbonyl)phenyl)propane-1-sulfonamide, N-(2,5-difluoro-3-(quinazoline-6-carbonyl)phenyl)propane-1-sulfonamide,
N-(2,5-difluoro-3-(1,7-naphthyridine-6-carbonyl)phenyl)propane-1-sulfonamide,
N-(2,5-difluoro-3-(pyrido[3,4-b]pyrazine-7-carbonyl)phenyl)propane-1-sulfonamide,
N-(2,5-difluoro-3-(1,5-naphthyridine-2-carbonyl)phenyl)propane-1-sulfonamide,
N-(3-(benzo[d]oxazole-6-carbonyl)-2,5-difluorophenyl)propane-1-sulfonamide,
N-(3-(benzo[d]oxazole-5-carbonyl)-2,5-difluorophenyl)propane-1-sulfonamide,
N-(2,5-difluoro-3-(oxazolo[5,4-b]pyridine-5-carbonyl)phenyl)propane-1-sulfonamide,
N-(3-(benzo[d]thiazole-6-carbonyl)-2,5-difluorophenyl)propane-1-sulfonamide,
N-(3-(3a,7a-dihydro-1H-pyrazolo[3,4-b]pyridine-3-carbonyl)-2,5-difluorophenyl)propane-1-sulfonamide,
N-(3-(7,7a-dihydro-4aH-pyrrolo[2,3-d]pyrimidine-5-carbonyl)-2,5-difluorophenyl)propane-1-sulfonamide,
N-(3-(5,7a-dihydro-4aH-pyrrolo[2,3-b]pyrazine-7-carbonyl)-2,5-difluorophenyl)propane-1-sulfonamide,
N-(3-(3a,7a-dihydro-1H-pyrazolo[3,4-b]pyrazine-3-carbonyl)-2,5-difluorophenyl)propane-1-sulfonamide,
N-(3-(7,7a-dihydro-4aH-pyrrolo[2,3-c]pyridazine-5-carbonyl)-2,5-difluorophenyl)propane-1-sulfonamide,
N-(2,5-difluoro-3-((2-hydroxyethyl)amino)quinoline-6-carbonyl)phenyl)propane-1-sulfonamide,
N-(2,5-difluoro-3-(pyrrolidin-1-yl)quinoline-6-carbonyl)phenyl)propane-1-sulfonamide,
N-(3-(3-(1H-imidazol-1-yl)quinoline-6-carbonyl)-2,5-difluorophenyl)propane-1-sulfonamide,
N-(3-(3-(1H-pyrazol-4-yl)quinoline-6-carbonyl)-2,5-difluorophenyl)propane-1-sulfonamide,
N-(3,4-difluoro-5-(quinoline-6-carbonyl)phenyl)propane-1-sulfonamide,
N-(3,4-difluoro-5-(3-methylquinoline-6-carbonyl)phenyl)propane-1-sulfonamide,
N-(3-(3-cyanoquinoline-6-carbonyl)-4,5-difluorophenyl)propane-1-sulfonamide,
N-(3,4-difluoro-5-(3-methoxyquinoline-6-carbonyl)phenyl)propane-1-sulfonamide,
N-(3-(3-(4-chlorophenyl)quinoline-6-carbonyl)-4,5-difluorophenyl)propane-1-sulfonamide,
N-(3,4-difluoro-5-(3-(pyridin-3-yl)quinoline-6-carbonyl)phenyl)propane-1-sulfonamide,
N-(3,4-difluoro-5-(3-morpholinoquinoline-6-carbonyl)phenyl)propane-1-sulfonamide,
N-(3,4-difluoro-5-(3-(piperazin-1-yl)quinoline-6-carbonyl)phenyl)propane-1-sulfonamide,
N-(3,4-difluoro-5-(3-(2-hydroxyethoxy)quinoline-6-carbonyl)phenyl)propane-1-sulfonamide,
N-(3,4-difluoro-5-(quinazoline-6-carbonyl)phenyl)propane-1-sulfonamide,
N-(3,4-difluoro-5-(1,7-naphthyridine-6-carbonyl)phenyl)propane-1-sulfonamide,
N-(3,4-difluoro-5-(pyrido[3,4-b]pyrazine-7-carbonyl)phenyl)propane-1-sulfonamide,
N-(3,4-difluoro-5-(1,5-naphthyridine-2-carbonyl)phenyl)propane-1-sulfonamide,
N-(3-(benzo[d]oxazole-6-carbonyl)-4,5-difluorophenyl)propane-1-sulfonamide,
N-(3-(benzo[d]oxazole-5-carbonyl)-4,5-difluorophenyl)propane-1-sulfonamide,
N-(3,4-difluoro-5-(oxazolo[5,4-b]pyridine-5-carbonyl)phenyl)propane-1-sulfonamide,
N-(3-(benzo[d]thiazole-6-carbonyl)-4,5-difluorophenyl)propane-1-sulfonamide,
N-(3-(3a,7a-dihydro-1H-pyrazolo[3,4-b]pyridine-3-carbonyl)-4,5-difluorophenyl)propane-1-sulfonamide,
N-(3-(7,7a-dihydro-4aH-pyrrolo[2,3-d]pyrimidine-5-carbonyl)-4,5-difluorophenyl)propane-1-sulfonamide,
N-(3-(5,7a-dihydro-4aH-pyrrolo[2,3-b]pyrazine-7-carbonyl)-4,5-difluorophenyl)propane-1-sulfonamide,
N-(3-(3a,7a-dihydro-1H-pyrazolo[3,4-b]pyrazine-3-carbonyl)-4,5-difluorophenyl)propane-1-sulfonamide,
N-(3-(7,7a-dihydro-4aH-pyrrolo[2,3-c]pyridazine-5-carbonyl)-4,5-difluorophenyl)propane-1-sulfonamide,
N-(3,4-difluoro-5-(3-((2-hydroxyethyl)amino)quinoline-6-carbonyl)phenyl)propane-1-sulfonamide,
N-(3,4-difluoro-5-(3-(pyrrolidin-1-yl)quinoline-6-carbonyl)phenyl)propane-1-sulfonamide,
N-(3-(3-(1H-imidazol-1-yl)quinoline-6-carbonyl)-4,5-difluorophenyl)propane-1-sulfonamide,
N-(3-(3-(1H-pyrazol-4-yl)quinoline-6-carbonyl)-4,5-difluorophenyl)propane-1-sulfonamide,
N-(2,4,5-trifluoro-3-(quinoline-6-carbonyl)phenyl)propane-1-sulfonamide,
N-(2,4,5-trifluoro-3-(3-methylquinoline-6-carbonyl)phenyl)propane-1-sulfonamide,
N-(3-(3-cyanoquinoline-6-carbonyl)-2,4,5-trifluorophenyl)propane-1-sulfonamide,
N-(2,4,5-trifluoro-3-(3-methoxyquinoline-6-carbonyl)phenyl)propane-1-sulfonamide,
N-(3-(3-(4-chlorophenyl)quinoline-6-carbonyl)-2,4,5-trifluorophenyl)propane-1-sulfonamide,
N-(2,4,5-trifluoro-3-(3-(pyridin-3-yl)quinoline-6-carbonyl)phenyl)propane-1-sulfonamide,
N-(2,4,5-trifluoro-3-(3-morpholinoquinoline-6-carbonyl)phenyl)propane-1-sulfonamide,
N-(2,4,5-trifluoro-3-(3-(piperazin-1-yl)quinoline-6-carbonyl)phenyl)propane-1-sulfonamide,
N-(2,4,5-trifluoro-3-(3-(2-hydroxyethoxy)quinoline-6-carbonyl)phenyl)propane-1-sulfonamide,
N-(2,4,5-trifluoro-3-(quinazoline-6-carbonyl)phenyl)propane-1-sulfonamide,
N-(2,4,5-trifluoro-3-(1,7-naphthyridine-6-carbonyl)phenyl)propane-1-sulfonamide,
N-(2,4,5-trifluoro-3-(pyrido[3,4-b]pyrazine-7-carbonyl)phenyl)propane-1-sulfonamide,
N-(2,4,5-trifluoro-3-(1,5-naphthyridine-2-carbonyl)phenyl)propane-1-sulfonamide,
N-(3-(benzo[d]oxazole-6-carbonyl)-2,4,5-trifluorophenyl)propane-1-sulfonamide,
N-(3-(benzo[d]oxazole-5-carbonyl)-2,4,5-trifluorophenyl)propane-1-sulfonamide,
N-(2,4,5-trifluoro-3-(oxazolo[5,4-b]pyridine-5-carbonyl)phenyl)propane-1-sulfonamide,
N-(3-(benzo[d]thiazole-6-carbonyl)-2,4,5-trifluorophenyl)propane-1-sulfonamide,
N-(3-(3a,7a-dihydro-1H-pyrazolo[3,4-b]pyridine-3-carbonyl)-2,4,5-trifluorophenyl)propane-1-sulfonamide,
N-(3-(7,7a-dihydro-4aH-pyrrolo[2,3-d]pyrimidine-5-carbonyl)-2,4,5-trifluorophenyl)propane-1-sulfonamide,
N-(3-(5,7a-dihydro-4aH-pyrrolo[2,3-b]pyrazine-7-carbonyl)-2,4,5-trifluorophenyl)propane-1-sulfonamide,
N-(3-(3a,7a-dihydro-1H-pyrazolo[3,4-b]pyrazine-3-carbonyl)-2,4,5-trifluorophenyl)propane-1-sulfonamide,
N-(3-(7,7a-dihydro-4aH-pyrrolo[2,3-c]pyridazine-5-carbonyl)-2,4,5-trifluorophenyl)propane-1-sulfonamide,
N-(2,4,5-trifluoro-3-(3-((2-hydroxyethyl)amino)quinoline-6-carbonyl)phenyl)propane-1-sulfonamide, N-(2,4,5-trifluoro-3-(3-(pyrrolidin-1-yl)quinoline-6-carbonyl)phenyl)propane-1-sulfonamide,
N-(3-(3-(1H-imidazol-1-yl)quinoline-6-carbonyl)-2,4,5-trifluorophenyl)propane-1-sulfonamide,
N-(3-(3-(1H-pyrazol-4-yl)quinoline-6-carbonyl)-2,4,5-trifluorophenyl)propane-1-sulfonamide,
1-(3-fluoro-5-(quinoline-6-carbonyl)phenyl)-3-(3-fluorophenyl)urea,
1-(3-fluoro-5-(3-methylquinoline-6-carbonyl)phenyl)-3-(3-fluorophenyl)urea,
1-(3-(3-cyanoquinoline-6-carbonyl)-5-fluorophenyl)-3-(3-fluorophenyl)urea,
1-(3-fluoro-5-(3-methoxyquinoline-6-carbonyl)phenyl)-3-(3-fluorophenyl)urea,
1-(3-fluoro-5-(3-morpholinoquinoline-6-carbonyl)phenyl)-3-(3-fluorophenyl)urea,
1-(3,4-difluorophenyl)-3-(3-fluoro-5-(3-morpholinoquinoline-6-carbonyl)phenyl)urea,
1-(3-fluoro-5-(3-morpholinoquinoline-6-carbonyl)phenyl)-3-(4-fluorophenyl)urea,
1-(4-chlorophenyl)-3-(3-fluoro-5-(3-morpholinoquinoline-6-carbonyl)phenyl)urea,
1-(3-chlorophenyl)-3-(3-fluoro-5-(3-morpholinoquinoline-6-carbonyl)phenyl)urea,
1-(4-chloro-3-(trifluoromethyl)phenyl)-3-(3-fluoro-5-(3-morpholinoquinoline-6-carbonyl)phenyl)urea,
1-(3-fluoro-5-(3-(pyrrolidin-1-yl)quinoline-6-carbonyl)phenyl)-3-(3-fluorophenyl)urea,
1-(3-fluoro-5-(3-(piperazin-1-yl)quinoline-6-carbonyl)phenyl)-3-(3-fluorophenyl)urea,
1-(3,4-difluorophenyl)-3-(3-fluoro-5-(3-(piperazin-1-yl)quinoline-6-carbonyl)phenyl)urea,
1-(3-fluoro-5-(3-(piperazin-1-yl)quinoline-6-carbonyl)phenyl)-3-(4-fluorophenyl)urea,
1-(4-chlorophenyl)-3-(3-fluoro-5-(3-(piperazin-1-yl)quinoline-6-carbonyl)phenyl)urea,
1-(3-fluoro-5-(3-(pyridin-3-yl)quinoline-6-carbonyl)phenyl)-3-(3-fluorophenyl)urea,
1-(3-fluoro-5-(3-(2-hydroxyethyl)amino)quinoline-6-carbonyl)phenyl)-3-(3-fluorophenyl)urea,
1-(3-fluoro-5-(3-(2-hydroxyethoxy)quinoline-6-carbonyl)phenyl)-3-(3-fluorophenyl)urea,
1-(3-(3-(1H-pyrazol-4-yl)quinoline-6-carbonyl)-5-fluorophenyl)-3-(3-fluorophenyl)urea,
1-(3-(3-(1H-imidazol-1-yl)quinoline-6-carbonyl)-5-fluorophenyl)-3-(3-fluorophenyl)urea,
1-(3-fluoro-5-(quinazoline-6-carbonyl)phenyl)-3-(3-fluorophenyl)urea,
1-(3-fluoro-5-(quinazoline-6-carbonyl)phenyl)-3-(4-fluorophenyl)urea,
1-(3,4-difluorophenyl)-3-(3-fluoro-5-(quinazoline-6-carbonyl)phenyl)urea,
1-(3-fluoro-5-(1,7-naphthyridine-6-carbonyl)phenyl)-3-(3-fluorophenyl)urea,
1-(3,4-difluorophenyl)-3-(3-fluoro-5-(1,7-naphthyridine-6-carbonyl)phenyl)urea,
1-(3-fluoro-5-(3-morpholino-1,7-naphthyridine-6-carbonyl)phenyl)-3-(3-fluorophenyl)urea,
1-(3,4-difluorophenyl)-3-(3-fluoro-5-(3-morpholino-1,7-naphthyridine-6-carbonyl)phenyl)urea,
1-(3-fluoro-5-(pyrido[3,4-b]pyrazine-7-carbonyl)phenyl)-3-(3-fluorophenyl)urea,
1-(3-fluoro-5-(pyrido[3,4-b]pyrazine-7-carbonyl)phenyl)-3-(4-fluorophenyl)urea,
1-(3-fluoro-5-(2-morpholinopyrido[3,4-b]pyrazine-7-carbonyl)phenyl)-3-(4-fluorophenyl)urea,
1-(3-fluoro-5-(2-morpholinopyrido[3,4-b]pyrazine-7-carbonyl)phenyl)-3-(3-fluorophenyl)urea,
1-(3-fluoro-5-(1,5-naphthyridine-2-carbonyl)phenyl)-3-(3-fluorophenyl)urea,
1-(3-fluoro-5-(7-morpholino-1,5-naphthyridine-2-carbonyl)phenyl)-3-(3-fluorophenyl)urea,
1-(3-(benzo[d]oxazole-6-carbonyl)-5-fluorophenyl)-3-(3-fluorophenyl)urea,
1-(3-(benzo[d]oxazole-5-carbonyl)-5-fluorophenyl)-3-(3-fluorophenyl)urea,
1-(3-(benzo[d]thiazole-6-carbonyl)-5-fluorophenyl)-3-(3-fluorophenyl)urea,
1-(3-(3a,7a-dihydro-1H-pyrazolo[3,4-b]pyridine-3-carbonyl)-5-fluorophenyl)-3-(3-fluorophenyl)urea,
1-(3-(7,7a-dihydro-4aH-pyrrolo[2,3-d]pyrimidine-5-carbonyl)-5-fluorophenyl)-3-(3-fluorophenyl)urea,
1-(3-(5,7a-dihydro-4aH-pyrrolo[2,3-b]pyrazine-7-carbonyl)-5-fluorophenyl)-3-(3-fluorophenyl)urea,
1-(3-(3a,7a-dihydro-1H-pyrazolo[3,4-b]pyrazine-3-carbonyl)-5-fluorophenyl)-3-(3-fluorophenyl)urea,
1-(3-(7,7a-dihydro-4aH-pyrrolo[2,3-c]pyridazine-5-carbonyl)-5-fluorophenyl)-3-(3-fluorophenyl)urea,
1-(2,5-difluoro-3-(quinoline-6-carbonyl)phenyl)-3-(3-fluorophenyl)urea,
1-(2,5-difluoro-3-(3-methylquinoline-6-carbonyl)phenyl)-3-(3-fluorophenyl)urea,
1-(3-(3-cyanoquinoline-6-carbonyl)-2,5-difluorophenyl)-3-(3-fluorophenyl)urea,
1-(2,5-difluoro-3-(3-methoxyquinoline-6-carbonyl)phenyl)-3-(3-fluorophenyl)urea,
1-(2,5-difluoro-3-(3-morpholinoquinoline-6-carbonyl)phenyl)-3-(3-fluorophenyl)urea,
1-(2,5-difluoro-3-(3-morpholinoquinoline-6-carbonyl)phenyl)-3-(3,4-difluorophenyl)urea,
1-(2,5-difluoro-3-(3-morpholinoquinoline-6-carbonyl)phenyl)-3-(4-fluorophenyl)urea,
1-(4-chlorophenyl)-3-(2,5-difluoro-3-(3-morpholinoquinoline-6-carbonyl)phenyl)urea,
1-(3-chlorophenyl)-3-(2,5-difluoro-3-(3-morpholinoquinoline-6-carbonyl)phenyl)urea,
1-(4-chloro-3-(trifluoromethyl)phenyl)-3-(2,5-difluoro-3-(3-morpholinoquinoline-6-carbonyl)phenyl)urea,
1-(2,5-difluoro-3-(3-(pyrrolidin-1-yl)quinoline-6-carbonyl)phenyl)-3-(3-fluorophenyl)urea,
1-(2,5-difluoro-3-(3-(piperazin-1-yl)quinoline-6-carbonyl)phenyl)-3-(3-fluorophenyl)urea,
1-(2,5-difluoro-3-(3-(piperazin-1-yl)quinoline-6-carbonyl)phenyl)-3-(3,4-difluorophenyl)urea,
1-(2,5-difluoro-3-(3-(piperazin-1-yl)quinoline-6-carbonyl)phenyl)-3-(4-fluorophenyl)urea,
1-(4-chlorophenyl)-3-(2,5-difluoro-3-(3-(piperazin-1-yl)quinoline-6-carbonyl)phenyl)urea,
1-(2,5-difluoro-3-(3-(pyridin-3-yl)quino carbonyl)phenyl)-3-(3-fluorophenyl)urea,
1-(2,5-difluoro-3-(3-(2-hydroxyethyl)amino)quinoline-6-carbonyl)phenyl)-3-(3-fluorophenyl)urea,
1-(2,5-difluoro-3-(3-(2-hydroxyethoxy)quinoline-6-carbonyl)phenyl)-3-(3-fluorophenyl)urea,
1-(3-(3-(1H-pyrazol-4-yl)quinoline-6-carbonyl)-2,5-difluorophenyl)-3-(3-fluorophenyl)urea,
1-(3-(3-(1H-imidazol-1-yl)quinoline-6-carbonyl)-2,5-difluorophenyl)-3-(3-fluorophenyl)urea,
1-(2,5-difluoro-3-(quinazoline-6-carbonyl)phenyl)-3-(3-fluorophenyl)urea,
1-(2,5-difluoro-3-(quinazoline-6-carbonyl)phenyl)-3-(4-fluorophenyl)urea, 1-(2,5-difluoro-3-(quinazoline-6-carbonyl)phenyl)-3-(3,4-difluorophenyl)urea,
1-(2,5-difluoro-3-(1,7-naphthyridine-6-carbonyl)phenyl)-3-(3-fluorophenyl)urea,
1-(2,5-difluoro-3-(1,7-naphthyridine-6-carbonyl)phenyl)-3-(3,4-difluorophenyl)urea,
1-(2,5-difluoro-3-(3-morpholino-1,7-naphthyridine-6-carbonyl)phenyl)-3-(3-fluorophenyl)urea,
1-(2,5-difluoro-3-(3-morpholino-1,7-naphthyridine-6-carbonyl)phenyl)-3-(3,4-difluorophenyl)urea,
1-(2,5-difluoro-3-(pyrido[3,4-b]pyrazine-7-carbonyl)phenyl)-3-(3-fluorophenyl)urea,
1-(2,5-difluoro-3-(pyrido[3,4-b]pyrazine-7-carbonyl)phenyl)-3-(4-fluorophenyl)urea,
1-(2,5-difluoro-3-(2-morpholinopyrido[3,4-b]pyrazine-7-carbonyl)phenyl)-3-(4-fluorophenyl)urea,
1-(2,5-difluoro-3-(2-morpholinopyrido[3,4-b]pyrazine-7-carbonyl)phenyl)-3-(3-fluorophenyl)urea,
1-(2,5-difluoro-3-(1,5-naphthyridine-2-carbonyl)phenyl)-3-(3-fluorophenyl)urea,
1-(2,5-difluoro-3-(7-morpholino-1,5-naphthyridine-2-carbonyl)phenyl)-3-(3-fluorophenyl)urea,
1-(3-(benzo[d]oxazole-6-carbonyl)-2,5-difluorophenyl)-3-(3-fluorophenyl)urea,
1-(3-(benzo[d]oxazole-5-carbonyl)-2,5-difluorophenyl)-3-(3-fluorophenyl)urea,
1-(3-(benzo[d]thiazole-6-carbonyl)-2,5-difluorophenyl)-3-(3-fluorophenyl)urea,
1-(3-(3a,7a-dihydro-1H-pyrazolo[3,4-b]pyridine-3-carbonyl)-2,5-difluorophenyl)-3-(3-fluorophenyl)urea,
1-(3-(7,7a-dihydro-4aH-pyrrolo[2,3-d]pyrimidine-5-carbonyl)-2,5-difluorophenyl)-3-(3-fluorophenyl)urea,
1-(3-(5,7a-dihydro-4aH-pyrrolo[2,3-b]pyrazine-7-carbonyl)-2,5-difluorophenyl)-3-(3-fluorophenyl)urea,
1-(3-(3a,7a-dihydro-1H-pyrazolo[3,4-b]pyrazine-3-carbonyl)-2,5-difluorophenyl)-3-(3-fluorophenyl)urea,
1-(3-(7,7a-dihydro-4aH-pyrrolo[2,3-c]pyridazine-5-carbonyl)-2,5-difluorophenyl)-3-(3-fluorophenyl)urea,
1-(3,4-difluoro-5-(quinoline-6-carbonyl)phenyl)-3-(3-fluorophenyl)urea,
1-(3-chlorophenyl)-3-(3,4-difluoro-5-(quinoline-6-carbonyl)phenyl)urea,
1-(4-chloro-3-fluorophenyl)-3-(3,4-difluoro-5-(quinoline-6-carbonyl)phenyl)urea,
1-(3-chloro-4-fluorophenyl)-3-(3,4-difluoro-5-(quinoline-6-carbonyl)phenyl)urea,
1-(4-chlorophenyl)-3-(3,4-difluoro-5-(quinoline-6-carbonyl)phenyl)urea,
1-(3,4-difluoro-5-(quinoline-6-carbonyl)phenyl)-3-(4-fluorophenyl)urea,
1-(3,4-difluoro-5-(quinoline-6-carbonyl)phenyl)-3-(3,4-difluorophenyl)urea,
1-(4-chloro-3-(trifluoromethyl)phenyl)-3-(3,4-difluoro-5-(quinoline-6-carbonyl)phenyl)urea,
1-(3,4-difluoro-5-(3-methylquinoline-6-carbonyl)phenyl)-3-(3-fluorophenyl)urea,
1-(3-(3-cyanoquinoline-6-carbonyl)-4,5-difluorophenyl)-3-(3-fluorophenyl)urea,
1-(3,4-difluoro-5-(3-methoxyquinoline-6-carbonyl)phenyl)-3-(3-fluorophenyl)urea,
1-(3,4-difluoro-5-(3-morpholinoquinoline-6-carbonyl)phenyl)-3-(3-fluorophenyl)urea,
1-(3,4-difluoro-5-(3-morpholinoquinoline-6-carbonyl)phenyl)-3-(3,4-difluorophenyl)urea,
1-(3,4-difluoro-5-(3-morpholinoquinoline-6-carbonyl)phenyl)-3-(4-fluorophenyl)urea,
1-(4-chlorophenyl)-3-(3,4-difluoro-5-(3-morpholinoquinoline-6-carbonyl)phenyl)urea,
1-(3-chlorophenyl)-3-(3,4-difluoro-5-(3-morpholinoquinoline-6-carbonyl)phenyl)urea,
1-(4-chloro-3-(trifluoromethyl)phenyl)-3-(3,4-difluoro-5-(3-morpholinoquinoline-6-carbonyl)phenyl)urea,
1-(3,4-difluoro-5-(3-(pyrrolidin-1-yl)quinoline-6-carbonyl)phenyl)-3-(3-fluorophenyl)urea,
1-(3,4-difluoro-5-(3-(piperazin-1-yl)quinoline-6-carbonyl)phenyl)-3-(3-fluorophenyl)urea,
1-(3,4-difluoro-5-(3-(piperazin-1-yl)quinoline-6-carbonyl)phenyl)-3-(3,4-difluorophenyl)urea,
1-(3,4-difluoro-5-(3-(piperazin-1-yl)quinoline-6-carbonyl)phenyl)-3-(4-fluorophenyl)urea,
1-(4-chlorophenyl)-3-(3,4-difluoro-5-(3-(piperazin-1-yl)quinoline-6-carbonyl)phenyl)urea,
1-(3,4-difluoro-5-(3-(pyridin-3-yl)quinoline-6-carbonyl)phenyl)-3-(3-fluorophenyl)urea,
1-(3,4-difluoro-5-(3-((2-hydroxyethyl)amino)quinoline-6-carbonyl)phenyl)-3-(3-fluorophenyl)urea,
1-(3,4-difluoro-5-(3-(2-hydroxyethoxy)quinoline-6-carbonyl)phenyl)-3-(3-fluorophenyl)urea,
1-(3-(3-(1H-pyrazol-4-yl)quinoline-6-carbonyl)-4,5-difluorophenyl)-3-(3-fluorophenyl)urea,
1-(3-(3-(1H-imidazol-1-yl)quinoline-6-carbonyl)-4,5-difluorophenyl)-3-(3-fluorophenyl)urea,
1-(3,4-difluoro-5-(quinazoline-6-carbonyl)phenyl)-3-(3-fluorophenyl)urea,
1-(3,4-difluoro-5-(quinazoline-6-carbonyl)phenyl)-3-(4-fluorophenyl)urea,
1-(4-chlorophenyl)-3-(3,4-difluoro-5-(quinazoline-6-carbonyl)phenyl)urea,
1-(3,4-difluoro-5-(quinazoline-6-carbonyl)phenyl)-3-(3,4-difluorophenyl)urea,
1-(4-chloro-3-fluorophenyl)-3-(3,4-difluoro-5-(quinazoline-6-carbonyl)phenyl)urea,
1-(4-chloro-3-(trifluoromethyl)phenyl)-3-(3,4-difluoro-5-(quinazoline-6-carbonyl)phenyl)urea,
1-(3-chloro-4-fluorophenyl)-3-(3,4-difluoro-5-(quinazoline-6-carbonyl)phenyl)urea,
1-(3,4-difluoro-5-(1,7-naphthyridine-6-carbonyl)phenyl)-3-(3-fluorophenyl)urea,
1-(3,4-difluoro-5-(1,7-naphthyridine-6-carbonyl)phenyl)-3-(3,4-difluorophenyl)urea,
1-(3,4-difluoro-5-(3-morpholino-1,7-naphthyridine-6-carbonyl)phenyl)-3-(3-fluorophenyl)urea,
1-(3,4-difluoro-5-(3-morpholino-1,7-naphthyridine-6-carbonyl)phenyl)-3-(3,4-difluorophenyl)urea,
1-(3,4-difluoro-5-(pyrido[3,4-b]pyrazine-7-carbonyl)phenyl)-3-(3-fluorophenyl)urea,
1-(3,4-difluoro-5-(pyrido[3,4-b]pyrazine-7-carbonyl)phenyl)-3-(4-fluorophenyl)urea,
1-(3,4-difluoro-5-(2-morpholinopyrido[3,4-b]pyrazine-7-carbonyl)phenyl)-3-(4-fluorophenyl)urea,
1-(3,4-difluoro-5-(2-morpholinopyrido[3,4-b]pyrazine-7-carbonyl)phenyl)-3-(3-fluorophenyl)urea,
1-(3,4-difluoro-5-(1,5-naphthyridine-2-carbonyl)phenyl)-3-(3-fluorophenyl)urea,
1-(3,4-difluoro-5-(7-morpholino-1,5-naphthyridine-2-carbonyl)phenyl)-3-(3-fluorophenyl)urea,
1-(3-(benzo[d]oxazole-6-carbonyl)-4,5-difluorophenyl)-3-(3-fluorophenyl)urea,
1-(3-(benzo[d]oxazole-5-carbonyl)-4,5-difluorophenyl)-3-(3-fluorophenyl)urea,
1-(3-(benzo[d]thiazole-6-carbonyl)-4,5-difluorophenyl)-3-(3-fluorophenyl)urea, 1-(3-(3a,7a-dihydro-1H-pyrazolo[3,4-b]pyridine-3-carbonyl)-4,5-difluorophenyl)-3-(3-fluorophenyl)urea,
1-(3-(7,7a-dihydro-4aH-pyrrolo[2,3-d]pyrimidine-5-carbonyl)-4,5-difluorophenyl)-3-(3-fluorophenyl)urea,
1-(3-(5,7a-dihydro-4aH-pyrrolo[2,3-b]pyrazine-7-carbonyl)-4,5-difluorophenyl)-3-(3-fluorophenyl)urea,
1-(3-(3a,7a-dihydro-1H-pyrazolo[3,4-b]pyrazine-3-carbonyl)-4,5-difluorophenyl)-3-(3-fluorophenyl)urea,
1-(3-(7,7a-dihydro-4aH-pyrrolo[2,3-c]pyridazine-5-carbonyl)-4,5-difluorophenyl)-3-(3-fluorophenyl)urea,
1-(3-fluorophenyl)-3-(2,4,5-trifluoro-3-(quinoline-6-carbonyl)phenyl)urea,
1-(3-fluorophenyl)-3-(2,4,5-trifluoro-3-(3-methylquinoline-6-carbonyl)phenyl)urea,
1-(3-(3-cyanoquinoline-6-carbonyl)-2,4,5-trifluorophenyl)-3-(3-fluorophenyl)urea,
1-(3-fluorophenyl)-3-(2,4,5-trifluoro-3-(3-methoxyquinoline-6-carbonyl)phenyl)urea,
1-(3-fluorophenyl)-3-(2,4,5-trifluoro-3-(3-morpholinoquinoline-6-carbonyl)phenyl)urea,
1-(3,4-difluorophenyl)-3-(2,4,5-trifluoro-3-(3-morpholinoquinoline-6-carbonyl)phenyl)urea,
1-(4-fluorophenyl)-3-(2,4,5-trifluoro-3-(3-morpholinoquinoline-6-carbonyl)phenyl)urea,
1-(4-chlorophenyl)-3-(2,4,5-trifluoro-3-(3-morpholinoquinoline-6-carbonyl)phenyl)urea,
1-(3-chlorophenyl)-3-(2,4,5-trifluoro-3-(3-morpholinoquinoline-6-carbonyl)phenyl)urea,
1-(4-chloro-3-(trifluoromethyl)phenyl)-3-(2,4,5-trifluoro-3-(3-morpholinoquinoline-6-carbonyl)phenyl)urea,
1-(3-fluorophenyl)-3-(2,4,5-trifluoro-3-(3-(pyrrolidin-1-yl)quinoline-6-carbonyl)phenyl)urea,
1-(3-fluorophenyl)-3-(2,4,5-trifluoro-3-(3-(piperazin-1-yl)quinoline-6-carbonyl)phenyl)urea,
1-(3,4-difluorophenyl)-3-(2,4,5-trifluoro-3-(3-(piperazin-1-yl)quinoline-6-carbonyl)phenyl)urea,
1-(4-fluorophenyl)-3-(2,4,5-trifluoro-3-(3-(piperazin-1-yl)quinoline-6-carbonyl)phenyl)urea,
1-(4-chlorophenyl)-3-(2,4,5-trifluoro-3-(3-(piperazin-1-yl)quinoline-6-carbonyl)phenyl)urea,
1-(3-fluorophenyl)-3-(2,4,5-trifluoro-3-(3-(pyridin-3-yl)quinoline-6-carbonyl)phenyl)urea,
1-(3-fluorophenyl)-3-(2,4,5-trifluoro-3-(3-((2-hydroxyethyl)amino)quinoline-6-carbonyl)phenyl)urea,
1-(3-fluorophenyl)-3-(2,4,5-trifluoro-3-(3-(2-hydroxyethoxy)quinoline-6-carbonyl)phenyl)urea,
1-(3-(3-(1H-pyrazol-4-yl)quinoline-6-carbonyl)-2,4,5-trifluorophenyl)-3-(3-fluorophenyl)urea,
1-(3-(3-(1H-imidazol-1-yl)quinoline-6-carbonyl)-2,4,5-trifluorophenyl)-3-(3-fluorophenyl)urea,
1-(3-fluorophenyl)-3-(2,4,5-trifluoro-3-(quinazoline-6-carbonyl)phenyl)urea,
1-(4-fluorophenyl)-3-(2,4,5-trifluoro-3-(quinazoline-6-carbonyl)phenyl)urea,
1-(3,4-difluorophenyl)-3-(2,4,5-trifluoro-3-(quinazoline-6-carbonyl)phenyl)urea,
1-(3-fluorophenyl)-3-(2,4,5-trifluoro-3-(1,7-naphthyridine-6-carbonyl)phenyl)urea,
1-(3,4-difluorophenyl)-3-(2,4,5-trifluoro-3-(1,7-naphthyridine-6-carbonyl)phenyl)urea,
1-(3-fluorophenyl)-3-(2,4,5-trifluoro-3-(3-morpholino-1,7-naphthyridine-6-carbonyl)phenyl)urea,
1-(3,4-difluorophenyl)-3-(2,4,5-trifluoro-3-(3-morpholino-1,7-naphthyridine-6-carbonyl)phenyl)urea,
1-(3-fluorophenyl)-3-(2,4,5-trifluoro-3-(pyrido[3,4-b]pyrazine-7-carbonyl)phenyl)urea,
1-(4-fluorophenyl)-3-(2,4,5-trifluoro-3-(pyrido[3,4-b]pyrazine-7-carbonyl)phenyl)urea,
1-(4-fluorophenyl)-3-(2,4,5-trifluoro-3-(2-morpholinopyrido[3,4-b]pyrazine-7-carbonyl)phenyl)urea,
1-(3-fluorophenyl)-3-(2,4,5-trifluoro-3-(2-morpholinopyrido[3,4-b]pyrazine-7-carbonyl)phenyl)urea,
1-(3-fluorophenyl)-3-(2,4,5-trifluoro-3-(1,5-naphthyridine-2-carbonyl)phenyl)urea,
1-(3-fluorophenyl)-3-(2,4,5-trifluoro-3-(7-morpholino-1,5-naphthyridine-2-carbonyl)phenyl)urea,
1-(3-(benzo[d]oxazole-6-carbonyl)-2,4,5-trifluorophenyl)-3-(3-fluorophenyl)urea,
1-(3-(benzo[d]oxazole-5-carbonyl)-2,4,5-trifluorophenyl)-3-(3-fluorophenyl)urea,
1-(3-(benzo[d]thiazole-6-carbonyl)-2,4,5-trifluorophenyl)-3-(3-fluorophenyl)urea,
1-(3-(3a,7a-dihydro-1H-pyrazolo[3,4-b]pyridine-3-carbonyl)-2,4,5-trifluorophenyl)-3-(3-fluorophenyl)urea,
1-(3-(7,7a-dihydro-4aH-pyrrolo[2,3-d]pyrimidine-5-carbonyl)-2,4,5-trifluorophenyl)-3-(3-fluorophenyl)urea,
1-(3-(5,7a-dihydro-4aH-pyrrolo[2,3-b]pyrazine-7-carbonyl)-2,4,5-trifluorophenyl)-3-(3-fluorophenyl)urea,
1-(3-(3a,7a-dihydro-1H-pyrazolo[3,4-b]pyrazine-3-carbonyl)-2,4,5-trifluorophenyl)-3-(3-fluorophenyl)urea,
1-(3-(7,7a-dihydro-4aH-pyrrolo[2,3-c]pyridazine-5-carbonyl)-2,4,5-trifluorophenyl)-3-(3-fluorophenyl)urea,
1-(4-fluorophenyl)-3-(2,4,5-trifluoro-3-(quinoline-6-carbonyl)phenyl)urea,
1-(3,4-difluorophenyl)-3-(2,4,5-trifluoro-3-(quinoline-6-carbonyl)phenyl)urea,
1-(3,5-difluorophenyl)-3-(2,4,5-trifluoro-3-(quinoline-6-carbonyl)phenyl)urea,
4-fluoro-N-(2,4,5-trifluoro-3-(quinoline-6-carbonyl)phenyl)benzamide,
3,5-difluoro-N-(2,4,5-trifluoro-3-(quinoline-6-carbonyl)phenyl)benzamide,
3,4-difluoro-N-(2,4,5-trifluoro-3-(quinoline-6-carbonyl)phenyl)benzamide,
3-fluoro-N-(3-fluoro-5-(quinoline-6-carbonyl)phenyl)benzamide,
3,4-difluoro-N-(3-fluoro-5-(quinoline-6-carbonyl)phenyl)benzamide,
4-fluoro-N-(3-fluoro-5-(quinoline-6-carbonyl)phenyl)benzamide,
3-chloro-N-(3-fluoro-5-(quinoline-6-carbonyl)phenyl)benzamide,
4-chloro-3-fluoro-N-(3-fluoro-5-(quinoline-6-carbonyl)phenyl)benzamide,
4-chloro-N-(3-fluoro-5-(quinoline-6-carbonyl)phenyl)-3-(trifluoromethyl)benzamide,
4-chloro-N-(3-fluoro-5-(quinoline-6-carbonyl)phenyl)benzamide,
3-fluoro-N-(3-fluoro-5-(3-methylquinoline-6-carbonyl)phenyl)benzamide,
N-(3-(3-cyanoquinoline-6-carbonyl)-5-fluorophenyl)-3-fluorobenzamide,
3-fluoro-N-(3-fluoro-5-(3-methoxyquinoline-6-carbonyl)phenyl)benzamide,
3-fluoro-N-(3-fluoro-5-(3-morpholinoquinoline-6-carbonyl)phenyl)benzamide,
3,4-difluoro-N-(3-fluoro-5-(3-morpholinoquinoline-6-carbonyl)phenyl)benzamide,
4-fluoro-N-(3-fluoro-5-(3-morpholinoquinoline-6-carbonyl)phenyl)benzamide,
4-chloro-N-(3-fluoro-5-(3-morpholinoquinoline-6-carbonyl)phenyl)benzamide, 3-chloro-N-(3-fluoro-5-(3-morpholinoquinoline-6-carbonyl)phenyl)benzamide,
4-chloro-N-(3-fluoro-5-(3-morpholinoquinoline-6-carbonyl)phenyl)-3-(trifluoromethyl)benzamide,
3-fluoro-N-(3-fluoro-5-(3-(pyrrolidin-1-yl)quinoline-6-carbonyl)phenyl)benzamide,
3-fluoro-N-(3-fluoro-5-(3-(piperazin-1-yl)quinoline-6-carbonyl)phenyl)benzamide,
3,4-difluoro-N-(3-fluoro-5-(3-(piperazin-1-yl)quinoline-6-carbonyl)phenyl)benzamide,
4-fluoro-N-(3-fluoro-5-(3-(piperazin-1-yl)quinoline-6-carbonyl)phenyl)benzamide,
4-chloro-N-(3-fluoro-5-(3-(piperazin-1-yl)quinoline-6-carbonyl)phenyl)benzamide,
3-fluoro-N-(3-fluoro-5-(3-(pyridin-3-yl)quinoline-6-carbonyl)phenyl)benzamide,
3-fluoro-N-(3-fluoro-5-(3-(2-hydroxyethyl)amino)quinoline-6-carbonyl)phenyl)benzamide,
3-fluoro-N-(3-fluoro-5-(3-(2-hydroxyethoxy)quinoline-6-carbonyl)phenyl)benzamide,
N-(3-(3-(1H-pyrazol-4-yl)quinoline-6-carbonyl)-5-fluorophenyl)-3-fluorobenzamide,
N-(3-(3-(1H-imidazol-1-yl)quinoline-6-carbonyl)-5-fluorophenyl)-3-fluorobenzamide,
3-fluoro-N-(3-fluoro-5-(quinazoline-6-carbonyl)phenyl)benzamide,
4-fluoro-N-(3-fluoro-5-(quinazoline-6-carbonyl)phenyl)benzamide,
3,4-difluoro-N-(3-fluoro-5-(quinazoline-6-carbonyl)phenyl)benzamide,
3-fluoro-N-(3-fluoro-5-(1,7-naphthyridine-6-carbonyl)phenyl)benzamide,
3,4-difluoro-N-(3-fluoro-5-(1,7-naphthyridine-6-carbonyl)phenyl)benzamide,
3-fluoro-N-(3-fluoro-5-(3-morpholino-1,7-naphthyridine-6-carbonyl)phenyl)benzamide,
3,4-difluoro-N-(3-fluoro-5-(3-morpholino-1,7-naphthyridine-6-carbonyl)phenyl)benzamide,
3-fluoro-N-(3-fluoro-5-(pyrido[3,4-b]pyrazine-7-carbonyl)phenyl)benzamide,
4-fluoro-N-(3-fluoro-5-(pyrido[3,4-b]pyrazine-7-carbonyl)phenyl)benzamide,
4-fluoro-N-(3-fluoro-5-(2-morpholinopyrido[3,4-b]pyrazine-7-carbonyl)phenyl)benzamide,
3-fluoro-N-(3-fluoro-5-(2-morpholinopyrido[3,4-b]pyrazine-7-carbonyl)phenyl)benzamide,
3-fluoro-N-(3-fluoro-5-(1,5-naphthyridine-2-carbonyl)phenyl)benzamide,
3-fluoro-N-(3-fluoro-5-(7-morpholino-1,5-naphthyridine-2-carbonyl)phenyl)benzamide,
N-(3-(benzo[d]oxazole-6-carbonyl)-5-fluorophenyl)-3-fluorobenzamide,
N-(3-(benzo[d]oxazole-5-carbonyl)-5-fluorophenyl)-3-fluorobenzamide,
N-(3-(benzo[d]thiazole-6-carbonyl)-5-fluorophenyl)-3-fluorobenzamide,
N-(3-(3a,7a-dihydro-1H-pyrazolo[3,4-b]pyridine-3-carbonyl)-5-fluorophenyl)-3-fluorobenzamide,
N-(3-(7,7a-dihydro-4aH-pyrrolo[2,3-d]pyrimidine-5-carbonyl)-5-fluorophenyl)-3-fluorobenzamide,
N-(3-(5,7a-dihydro-4aH-pyrrolo[2,3-b]pyrazine-7-carbonyl)-5-fluorophenyl)-3-fluorobenzamide,
N-(3-(3a,7a-dihydro-1H-pyrazolo[3,4-b]pyrazine-3-carbonyl)-5-fluorophenyl)-3-fluorobenzamide,
N-(3-(7,7a-dihydro-4aH-pyrrolo[2,3-c]pyridazine-5-carbonyl)-5-fluorophenyl)-3-fluorobenzamide,
N-(2,5-difluoro-3-(quinoline-6-carbonyl)phenyl)-3-fluorobenzamide,
N-(2,5-difluoro-3-(3-methylquinoline-6-carbonyl)phenyl)-3-fluorobenzamide,
N-(3-(3-cyanoquinoline-6-carbonyl)-2,5-difluorophenyl)-3-fluorobenzamide,
N-(2,5-difluoro-3-(3-methoxyquinoline-6-carbonyl)phenyl)-3-fluorobenzamide,
N-(2,5-difluoro-3-(3-morpholinoquinoline-6-carbonyl)phenyl)-3-fluorobenzamide,
N-(2,5-difluoro-3-(3-morpholinoquinoline-6-carbonyl)phenyl)-3,4-difluorobenzamide,
N-(2,5-difluoro-3-(3-morpholinoquinoline-6-carbonyl)phenyl)-4-fluorobenzamide,
4-chloro-N-(2,5-difluoro-3-(3-morpholinoquinoline-6-carbonyl)phenyl)benzamide,
3-chloro-N-(2,5-difluoro-3-(3-morpholinoquinoline-6-carbonyl)phenyl)benzamide,
4-chloro-N-(2,5-difluoro-3-(3-morpholinoquinoline-6-carbonyl)phenyl)-3-(trifluoromethyl)benzamide,
N-(2,5-difluoro-3-(3-(pyrrolidin-1-yl)quinoline-6-carbonyl)phenyl)-3-fluorobenzamide,
N-(2,5-difluoro-3-(3-(piperazin-1-yl)quinoline-6-carbonyl)phenyl)-3-fluorobenzamide,
N-(2,5-difluoro-3-(3-(piperazin-1-yl)quinoline-6-carbonyl)phenyl)-3,4-difluorobenzamide,
N-(2,5-difluoro-3-(3-(piperazin-1-yl)quinoline-6-carbonyl)phenyl)-4-fluorobenzamide,
4-chloro-N-(2,5-difluoro-3-(3-(piperazin-1-yl)quinoline-6-carbonyl)phenyl)benzamide,
N-(2,5-difluoro-3-(3-(pyridin-3-yl)quinoline-6-carbonyl)phenyl)-3-fluorobenzamide,
N-(2,5-difluoro-3-(3-((2-hydroxyethyl)amino)quinoline-6-carbonyl)phenyl)-3-fluorobenzamide,
N-(2,5-difluoro-3-(3-(2-hydroxyethoxy)quinoline-6-carbonyl)phenyl)-3-fluorobenzamide,
N-(3-(3-(1H-pyrazol-4-yl)quinoline-6-carbonyl)-2,5-difluorophenyl)-3-fluorobenzamide,
N-(3-(3-(1H-imidazol-1-yl)quinoline-6-carbonyl)-2,5-difluorophenyl)-3-fluorobenzamide,
N-(2,5-difluoro-3-(quinazoline-6-carbonyl)phenyl)-3-fluorobenzamide,
N-(2,5-difluoro-3-(quinazoline-6-carbonyl)phenyl)-4-fluorobenzamide,
N-(2,5-difluoro-3-(quinazoline-6-carbonyl)phenyl)-3,4-difluorobenzamide,
N-(2,5-difluoro-3-(1,7-naphthyridine-6-carbonyl)phenyl)-3-fluorobenzamide,
N-(2,5-difluoro-3-(1,7-naphthyridine-6-carbonyl)phenyl)-3,4-difluorobenzamide,
N-(2,5-difluoro-3-(3-morpholino-1,7-naphthyridine-6-carbonyl)phenyl)-3-fluorobenzamide,
N-(2,5-difluoro-3-(3-morpholino-1,7-naphthyridine-6-carbonyl)phenyl)-3,4-difluorobenzamide,
N-(2,5-difluoro-3-(pyrido[3,4-b]pyrazine-7-carbonyl)phenyl)-3-fluorobenzamide,
N-(2,5-difluoro-3-(pyrido[3,4-b]pyrazine-7-carbonyl)phenyl)-4-fluorobenzamide,
N-(2,5-difluoro-3-(2-morpholinopyrido[3,4-b]pyrazine-7-carbonyl)phenyl)-4-fluorobenzamide,
N-(2,5-difluoro-3-(2-morpholinopyrido[3,4-b]pyrazine-7-carbonyl)phenyl)-3-fluorobenzamide,
N-(2,5-difluoro-3-(1,5-naphthyridine-2-carbonyl)phenyl)-3-fluorobenzamide,
N-(2,5-difluoro-3-(7-morpholino-1,5-naphthyridine-2-carbonyl)phenyl)-3-fluorobenzamide, N-(3-(benzo[d]oxazole-6-carbonyl)-2,5-difluorophenyl)-3-fluorobenzamide,
N-(3-(benzo[d]oxazole-5-carbonyl)-2,5-difluorophenyl)-3-fluorobenzamide,
N-(3-(benzo[d]thiazole-6-carbonyl)-2,5-difluorophenyl)-3-fluorobenzamide,
N-(3-(3a,7a-dihydro-1H-pyrazolo[3,4-b]pyridine-3-carbonyl)-2,5-difluorophenyl)-3-fluorobenzamide,
N-(3-(7,7a-dihydro-4aH-pyrrolo[2,3-d]pyrimidine-5-carbonyl)-2,5-difluorophenyl)-3-fluorobenzamide,
N-(3-(5,7a-dihydro-4aH-pyrrolo[2,3-b]pyrazine-7-carbonyl)-2,5-difluorophenyl)-3-fluorobenzamide,
N-(3-(3a,7a-dihydro-1H-pyrazolo[3,4-b]pyrazine-3-carbonyl)-2,5-difluorophenyl)-3-fluorobenzamide,
N-(3-(7,7a-dihydro-4aH-pyrrolo[2,3-c]pyridazine-5-carbonyl)-2,5-difluorophenyl)-3-fluorobenzamide,
N-(3,4-difluoro-5-(quinoline-6-carbonyl)phenyl)-3-fluorobenzamide,
N-(3,4-difluoro-5-(quinoline-6-carbonyl)phenyl)-3,4-difluorobenzamide,
N-(3,4-difluoro-5-(quinoline-6-carbonyl)phenyl)-4-fluorobenzamide,
3-chloro-N-(3,4-difluoro-5-(quinoline-6-carbonyl)phenyl)benzamide,
4-chloro-N-(3,4-difluoro-5-(quinoline-6-carbonyl)phenyl)-3-fluorobenzamide,
4-chloro-N-(3,4-difluoro-5-(quinoline-6-carbonyl)phenyl)-3-(trifluoromethyl)benzamide,
4-chloro-N-(3,4-difluoro-5-(quinoline-6-carbonyl)phenyl)benzamide,
N-(3,4-difluoro-5-(3-methylquinoline-6-carbonyl)phenyl)-3-fluorobenzamide,
N-(3-(3-cyanoquinoline-6-carbonyl)-4,5-difluorophenyl)-3-fluorobenzamide,
N-(3,4-difluoro-5-(3-methoxyquinoline-6-carbonyl)phenyl)-3-fluorobenzamide,
N-(3,4-difluoro-5-(3-morpholino quinoline-6-carbonyl)phenyl)-3-fluorobenzamide,
N-(3,4-difluoro-5-(3-morpholino quinoline-6-carbonyl)phenyl)-3,4-difluorobenzamide,
N-(3,4-difluoro-5-(3-morpholino quinoline-6-carbonyl)phenyl)-4-fluorobenzamide,
4-chloro-N-(3,4-difluoro-5-(3-morpholinoquinoline-6-carbonyl)phenyl)benzamide,
3-chloro-N-(3,4-difluoro-5-(3-morpholinoquinoline-6-carbonyl)phenyl)benzamide,
4-chloro-N-(3,4-difluoro-5-(3-morpholinoquinoline-6-carbonyl)phenyl)-3-(trifluoromethyl)benzamide,
N-(3,4-difluoro-5-(3-(pyrrolidin-1-yl)quinoline-6-carbonyl)phenyl)-3-fluorobenzamide,
N-(3,4-difluoro-5-(3-(piperazin-1-yl)quinoline-6-carbonyl)phenyl)-3-fluorobenzamide,
N-(3,4-difluoro-5-(3-(piperazin-1-yl)quinoline-6-carbonyl)phenyl)-3,4-difluorobenzamide,
N-(3,4-difluoro-5-(3-(piperazin-1-yl)quinoline-6-carbonyl)phenyl)-4-fluorobenzamide,
4-chloro-N-(3,4-difluoro-5-(3-(piperazin-1-yl)quinoline-6-carbonyl)phenyl)benzamide,
N-(3,4-difluoro-5-(3-(pyridin-3-yl)quinoline-6-carbonyl)phenyl)-3-fluorobenzamide,
N-(3,4-difluoro-5-(3-((2-hydroxyethyl)amino)quinoline-6-carbonyl)phenyl)-3-fluorobenzamide,
N-(3,4-difluoro-5-(3-(2-hydroxyethoxy)quinoline-6-carbonyl)phenyl)-3-fluorobenzamide,
N-(3-(3-(1H-pyrazol-4-yl)quinoline-6-carbonyl)-4,5-difluorophenyl)-3-fluorobenzamide,
N-(3-(3-(1H-imidazol-1-yl)quinoline-6-carbonyl)-4,5-difluorophenyl)-3-fluorobenzamide,
N-(3,4-difluoro-5-(quinazoline-6-carbonyl)phenyl)-3-fluorobenzamide,
N-(3,4-difluoro-5-(quinazoline-6-carbonyl)phenyl)-4-fluorobenzamide,
N-(3,4-difluoro-5-(quinazoline-6-carbonyl)phenyl)-3,4-difluorobenzamide,
N-(3,4-difluoro-5-(1,7-naphthyridine-6-carbonyl)phenyl)-3-fluorobenzamide,
N-(3,4-difluoro-5-(1,7-naphthyridine-6-carbonyl)phenyl)-3,4-difluorobenzamide,
N-(3,4-difluoro-5-(3-morpholino-1,7-naphthyridine-6-carbonyl)phenyl)-3-fluorobenzamide,
N-(3,4-difluoro-5-(3-morpholino-1,7-naphthyridine-6-carbonyl)phenyl)-3,4-difluorobenzamide,
N-(3,4-difluoro-5-(pyrido[3,4-b]pyrazine-7-carbonyl)phenyl)-3-fluorobenzamide,
N-(3,4-difluoro-5-(pyrido[3,4-b]pyrazine-7-carbonyl)phenyl)-4-fluorobenzamide,
N-(3,4-difluoro-5-(2-morpholinopyrido[3,4-b]pyrazine-7-carbonyl)phenyl)-4-fluorobenzamide,
N-(3,4-difluoro-5-(2-morpholinopyrido[3,4-b]pyrazine-7-carbonyl)phenyl)-3-fluorobenzamide,
N-(3,4-difluoro-5-(1,5-naphthyridine-2-carbonyl)phenyl)-3-fluorobenzamide,
N-(3,4-difluoro-5-(7-morpholino-1,5-naphthyridine-2-carbonyl)phenyl)-3-fluorobenzamide,
N-(3-(benzo[d]oxazole-6-carbonyl)-4,5-difluorophenyl)-3-fluorobenzamide,
N-(3-(benzo[d]oxazole-5-carbonyl)-4,5-difluorophenyl)-3-fluorobenzamide,
N-(3-(benzo[d]thiazole-6-carbonyl)-4,5-difluorophenyl)-3-fluorobenzamide,
N-(3-(3a,7a-dihydro-1H-pyrazolo[3,4-b]pyridine-3-carbonyl)-4,5-difluorophenyl)-3-fluorobenzamide,
N-(3-(7,7a-dihydro-4aH-pyrrolo[2,3-d]pyrimidine-5-carbonyl)-4,5-difluorophenyl)-3-fluorobenzamide,
N-(3-(5,7a-dihydro-4aH-pyrrolo[2,3-b]pyrazine-7-carbonyl)-4,5-difluorophenyl)-3-fluorobenzamide,
N-(3-(3a,7a-dihydro-1H-pyrazolo[3,4-b]pyrazine-3-carbonyl)-4,5-difluorophenyl)-3-fluorobenzamide,
N-(3-(7,7a-dihydro-4aH-pyrrolo[2,3-c]pyridazine-5-carbonyl)-4,5-difluorophenyl)-3-fluorobenzamide,
3-fluoro-N-(2,4,5-trifluoro-3-(quinoline-6-carbonyl)phenyl)benzamide,
3-fluoro-N-(2,4,5-trifluoro-3-(3-methylquinoline-6-carbonyl)phenyl)benzamide,
N-(3-(3-cyanoquinoline-6-carbonyl)-2,4,5-trifluorophenyl)-3-fluorobenzamide,
3-fluoro-N-(2,4,5-trifluoro-3-(3-methoxyquinoline-6-carbonyl)phenyl)benzamide,
3-fluoro-N-(2,4,5-trifluoro-3-(3-morpholinoquinoline-6-carbonyl)phenyl)benzamide,
3,4-difluoro-N-(2,4,5-trifluoro-3-(3-morpholinoquinoline-6-carbonyl)phenyl)benzamide,
4-fluoro-N-(2,4,5-trifluoro-3-(3-morpholinoquinoline-6-carbonyl)phenyl)benzamide,
4-chloro-N-(2,4,5-trifluoro-3-(3-morpholinoquinoline-6-carbonyl)phenyl)benzamide,
3-chloro-N-(2,4,5-trifluoro-3-(3-morpholinoquinoline-6-carbonyl)phenyl)benzamide,
4-chloro-N-(2,4,5-trifluoro-3-(3-morpholinoquinoline-6-carbonyl)phenyl)-3-(trifluoromethyl)benzamide,
3-fluoro-N-(2,4,5-trifluoro-3-(3-(pyrrolidin-1-yl)quinoline-6-carbonyl)phenyl)benzamide, 3-fluoro-N-(2,4,5-trifluoro-3-(3-(piperazin-1-yl)quinoline-6-carbonyl)phenyl)benzamide,
3,4-difluoro-N-(2,4,5-trifluoro-3-(3-(piperazin-1-yl)quinoline-6-carbonyl)phenyl)benzamide,
4-fluoro-N-(2,4,5-trifluoro-3-(3-(piperazin-1-yl)quinoline-6-carbonyl)phenyl)benzamide,
4-chloro-N-(2,4,5-trifluoro-3-(3-(piperazin-1-yl)quinoline-6-carbonyl)phenyl)benzamide,
3-fluoro-N-(2,4,5-trifluoro-3-(3-(pyridin-3-yl)quinoline-6-carbonyl)phenyl)benzamide,
3-fluoro-N-(2,4,5-trifluoro-3-(3-((2-hydroxyethyl)amino)quinoline-6-carbonyl)phenyl)benzamide,
3-fluoro-N-(2,4,5-trifluoro-3-(3-(2-hydroxyethoxy)quinoline-6-carbonyl)phenyl)benzamide,
N-(3-(3-(1H-pyrazol-4-yl)quinoline-6-carbonyl)-2,4,5-trifluorophenyl)-3-fluorobenzamide,
N-(3-(3-(1H-imidazol-1-yl)quinoline-6-carbonyl)-2,4,5-trifluorophenyl)-3-fluorobenzamide,
3-fluoro-N-(2,4,5-trifluoro-3-(quinazoline-6-carbonyl)phenyl)benzamide,
4-fluoro-N-(2,4,5-trifluoro-3-(quinazoline-6-carbonyl)phenyl)benzamide,
3,4-difluoro-N-(2,4,5-trifluoro-3-(quinazoline-6-carbonyl)phenyl)benzamide,
3-fluoro-N-(2,4,5-trifluoro-3-(1,7-naphthyridine-6-carbonyl)phenyl)benzamide,
3,4-difluoro-N-(2,4,5-trifluoro-3-(1,7-naphthyridine-6-carbonyl)phenyl)benzamide,
3-fluoro-N-(2,4,5-trifluoro-3-(3-morpholino-1,7-naphthyridine-6-carbonyl)phenyl)benzamide,
3,4-difluoro-N-(2,4,5-trifluoro-3-(3-morpholino-1,7-naphthyridine-6-carbonyl)phenyl)benzamide,
3-fluoro-N-(2,4,5-trifluoro-3-(pyrido[3,4-b]pyrazine-7-carbonyl)phenyl)benzamide,
4-fluoro-N-(2,4,5-trifluoro-3-(pyrido[3,4-b]pyrazine-7-carbonyl)phenyl)benzamide,
4-fluoro-N-(2,4,5-trifluoro-3-(2-morpholinopyrido[3,4-b]pyrazine-7-carbonyl)phenyl)benzamide,
3-fluoro-N-(2,4,5-trifluoro-3-(2-morpholinopyrido[3,4-b]pyrazine-7-carbonyl)phenyl)benzamide,
3-fluoro-N-(2,4,5-trifluoro-3-(1,5-naphthyridine-2-carbonyl)phenyl)benzamide,
3-fluoro-N-(2,4,5-trifluoro-3-(7-morpholino-1,5-naphthyridine-2-carbonyl)phenyl)benzamide,
N-(3-(benzo[d]oxazole-6-carbonyl)-2,4,5-trifluorophenyl)-3-fluorobenzamide,
N-(3-(benzo[d]oxazole-5-carbonyl)-2,4,5-trifluorophenyl)-3-fluorobenzamide,
N-(3-(benzo[d]thiazole-6-carbonyl)-2,4,5-trifluorophenyl)-3-fluorobenzamide,
N-(3-(3a,7a-dihydro-1H-pyrazolo[3,4-b]pyridine-3-carbonyl)-2,4,5-trifluorophenyl)-3-fluorobenzamide,
N-(3-(7,7a-dihydro-4aH-pyrrolo[2,3-d]pyrimidine-5-carbonyl)-2,4,5-trifluorophenyl)-3-fluorobenzamide,
N-(3-(5,7a-dihydro-4aH-pyrrolo[2,3-b]pyrazine-7-carbonyl)-2,4,5-trifluorophenyl)-3-fluorobenzamide,
N-(3-(3a,7a-dihydro-1H-pyrazolo[3,4-b]pyrazine-3-carbonyl)-2,4,5-trifluorophenyl)-3-fluorobenzamide, and
N-(3-(7,7a-dihydro-4aH-pyrrolo[2,3-c]pyridazine-5-carbonyl)-2,4,5-trifluorophenyl)-3-fluorobenzamide,
and pharmaceutically acceptable salts thereof.

In yet another aspect, the present disclosure provides a compound chosen from the compounds set forth in Table 1 below and pharmaceutically acceptable salts thereof.

TABLE 1

Illustrative Compounds of the Present Invention

| Compound No. | Chemical Name |
|---|---|
| C001 | N-(2,4,5-trifluoro-3-(quinoline-6-carbonyl)phenyl)propane-1-sulfonamide |
| C002 | 1-(3-fluorophenyl)-3-(2,4,5-trifluoro-3-(quinoline-6-carbonyl)phenyl)urea |
| C003 | 1-(4-fluorophenyl)-3-(2,4,5-trifluoro-3-(quinoline-6-carbonyl)phenyl)urea |
| C004 | 1-(3,4-difluorophenyl)-3-(2,4,5-trifluoro-3-(quinoline-6-carbonyl)phenyl)urea |
| C005 | 1-(3,5-difluorophenyl)-3-(2,4,5-trifluoro-3-(quinoline-6-carbonyl)phenyl)urea |
| C006 | 3-fluoro-N-(2,4,5-trifluoro-3-(quinoline-6-carbonyl)phenyl)benzamide |
| C007 | 4-fluoro-N-(2,4,5-trifluoro-3-(quinoline-6-carbonyl)phenyl)benzamide |
| C008 | 3,5-difluoro-N-(2,4,5-trifluoro-3-(quinoline-6-carbonyl)phenyl)benzamide |
| C009 | 3,4-difluoro-N-(2,4,5-trifluoro-3-(quinoline-6-carbonyl)phenyl)benzamide |
| C010 | N-(2,4,5-trifluoro-3-(quinazoline-6-carbonyl)phenyl)propane-1-sulfonamide |

In some embodiments, a compound of Formula I binds to a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I binds to a kinase selected from the group consisting of A-Raf, B-Raf, B-Raf V600E mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret, and any mutated versions thereof. In some embodiments, the compound of Formula I binds to a kinase selected from the group consisting of A-Raf, B-Raf, B-Raf V600E mutant, B-Raf V600E/T5291 mutant, c-Raf-1, or KDR. For example, the compound of Formula I binds to a kinase which is B-Raf or B-Raf V600E mutant. In some embodiments, a compound of Formula I binds to a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof, with a Kd which is lower than 50 µM, 25 µM, 10 µM, 5 µM, or 1 µM as measured in an in vitro assay. For example, the compound of Formula I binds to a kinase selected from the group consisting of A-Raf, B-Raf, B-Raf V600E mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret, and any mutated versions thereof with a Kd which is lower than 50 µM, 25 µM, 10 µM, 5 µM, or 1 µM as measured in an in vitro assay. In some embodiments, the compound of Formula I binds to a kinase selected from the group consisting of A-Raf, B-Raf, B-Raf V600E mutant, B-Raf V600E/T5291 mutant, c-Raf-1, or KDR with a Kd which is lower than 50 nM, 25 µM, 10 µM, 5 µM, or 1 µM as measured in an in vitro assay. For example, the compound of Formula I binds to a kinase which is B-Raf or B-Raf V600E mutant with a Kd which is lower than 50 µM, 25 µM, 10 µM, 5 µM, or 104 as measured in an in vitro assay.

In some embodiments, a compound of Formula I inhibits a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I inhibits a kinase selected from the group consisting of A-Raf, B-Raf, B-Raf V600E mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret, and any mutated versions thereof. In some embodiments, the compound of Formula I inhibits a kinase selected from the group consisting of A-Raf, B-Raf, B-Raf V600E mutant, B-Raf V600E/T5291 mutant, c-Raf-1, or KDR. For example, the compound of Formula I inhibits a kinase which is B-Raf or B-Raf V600E mutant. In some embodiments, a compound of Formula I inhibits a kinase including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof with an $IC_{50}$ in an in vitro assay of 10 µM, 5 µM, 2 µM, 1 µM, 500 nM, 200 nM, 100 nM or less as ascertained in an in vitro kinase assay. For example, the compound of Formula I inhibits a kinase selected from the group consisting of A-Raf, B-Raf, B-Raf V600E mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret, and any mutated versions thereof with an $IC_{50}$ in an in vitro assay of 10 µM, 5 µM, 2 µM, 1 µM, 500 nM, 200 nM, 100 nM or less as ascertained in an in vitro kinase assay. In some embodiments, the compound of Formula I inhibits a kinase selected from the group consisting of A-Raf, B-Raf, B-Raf V600E mutant, B-Raf V600E/T5291 mutant, c-Raf-1, and KDR with an $IC_{50}$ in an in vitro assay of 10 µM, 5 µM, 2 µM, 1 µM, 500 nM, 200 nM, 100 nM or less as ascertained in an in vitro kinase assay. For example, the compound of Formula I inhibits a kinase which is B-Raf or B-Raf V600E mutant with an $IC_{50}$ in an in vitro assay of 10 µM, 5 µM, 2 µM, 1 µM, 500 nM, 200 nM, 100 nM or less as ascertained in an in vitro kinase assay.

In some embodiments, the compound of Formula I inhibits the activity of one or more kinases selected from the group consisting of A-Raf, B-Raf, B-Raf V600E mutant, B-Raf V600E/T5291 mutant, c-Raf-1, and KDR with an $IC_{50}$ in an in vitro assay of 1 µM, 500 nM, 200 nM, 100 nM, 50 nM, 25 nM or less as ascertained in an in vitro kinase assay.

In some embodiments, the compound of Formula I selectively inhibits the activity of one or more kinases selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I selectively inhibits the activity of one or more kinases selected from the group consisting of A-Raf, B-Raf, B-Raf V600E mutant, B-Raf V600E/T5291 mutant, c-Raf-1, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret. In some embodiments, the compound of Formula I selectively inhibits the activity of one or more kinases selected from the group consisting of A-Raf, B-Raf, B-Raf V600E mutant, B-Raf V600E/T5291 mutant, c-Raf-1, and KDR.

In some embodiments, the compound of Formula I selectively inhibits the activity of B-Raf, B-Raf V600E mutant or KDR relative to one or more kinases selected from the group consisting of ABL1, AKT1 (PKB alpha), AURKB (Aurora B), BLK, BTK, CDK1/cyclin B, CHEK1 (CHK1), CSF1R (FMS), CSNK1G2 (CK1 gamma 2), EGFR (ErbB1), FGFR1, FGR, FLT3, FRAP1 (mTOR), FYN, IGF1R, IKBKB (IKK beta), INSR, KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES1. In some embodiments, the compound of Formula I selectively inhibits the activity of one or more kinases selected from the group consisting of A-Raf, B-Raf, B-Raf V600E mutant, B-Raf V600E/T5291 mutant, c-Raf-1, and KDR with an $IC_{50}$ which is $\frac{1}{2}$, $\frac{1}{3}^{rd}$, $\frac{1}{4}^{th}$, $\frac{1}{5}^{th}$, $\frac{1}{7}^{th}$, $\frac{1}{10}^{th}$, $\frac{1}{15}^{th}$, $\frac{1}{20}^{th}$, $\frac{1}{25}^{th}$, $\frac{1}{30}^{th}$, $\frac{1}{40}^{th}$, $\frac{1}{50}^{th}$, $\frac{1}{100}^{th}$, $\frac{1}{150}^{th}$, $\frac{1}{200}^{th}$, $\frac{1}{300}^{th}$, $\frac{1}{400}^{th}$, $\frac{1}{500}^{th}$, $\frac{1}{1000}^{th}$, $\frac{1}{2000}^{th}$ or less than the $IC_{50}$ for a kinase selected from the group consisting of ABL1, AKT1 (PKB alpha), AURKB (Aurora B), BLK, BTK, CDK1/cyclin B, CHEK1 (CHK1), CSF1R (FMS), CSNK1G2 (CK1 gamma 2), EGFR (ErbB1), FGFR1, FGR, FLT3, FRAP1 (mTOR), FYN, IGF1R, IKBKB (IKK beta), INSR, KIT, LCK, LYN A, MAP2K1 (MEK1), MAP4K5 (KHS1), MAPK1 (ERK2), MAPK14 (p38 alpha), MAPKAPK2, MET (cMet), PDG- FRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES1.

In some embodiments, one or more compounds of Formula I are capable of inhibiting cellular proliferation. For example, In some embodiments, one or more compounds of Formula I inhibit proliferation of tumor cells or tumor cell lines. For example, such cell lines express a kinase which is B-raf or B-raf V600E mutant. In some embodiments, the compounds of Formula I inhibit A375 or A549 cell proliferation in vitro or in an in vivo model such as a xenograft mouse model. In some embodiments, in vitro cultured A375 or A549 cell proliferation may be inhibited with an $IC_{50}$ of less than 100 µM, 75 µM, 50 µM, 25 µM, 15 µM, 10 µM, 5 µM, 3 µM, 2 µM, 1 µM or less by one or more compounds of Formula I, such as the compounds listed in Table 1.

B. Methods of Making

Compounds disclosed herein may be prepared by the routes described below.

Materials used herein are either commercially available or prepared by synthetic methods generally known in the art. These schemes are not limited to the compounds listed or by any particular substituents, which are employed for illustrative purposes. Although various steps of are described and depicted in Schemes A-C, the steps in some cases may be performed in a different order than the order shown in Schemes A-C. Various modifications to these synthetic reaction schemes may be made and will be suggested to one skilled in the art having referred to the disclosure contained in this application. Numbering does not necessarily correspond to that of claims or other tables.

In Scheme A, compounds of Formula I are synthesized by activating the carboxyl group in A-1 to provide A-2 with a leaving group attached to the carbonyl. Examples of leaving groups include, but are not limited to, dimethylhydroxylamino (e.g. Weinreb amide), halogen, alkane- or arylsulfonyloxy, or acyloxy, and the like. In a further embodiment, A-2 is a Weinreb amide. In a separate reaction vessel, aryl A-3 is subjected to a metallation reaction to form metallated aryl A-4. Suitable reagents for carrying out the metallation reaction include, but are not limited to, n-BuLi, sec-BuLi, t-BuLi, t-BuOK, or i-PrMgCl lithium chloride complex, and the like. Suitable solvents include, but are not limited to, tetrahydrofuran, diethyl ether, petane, 1,4-dioxane, methyl t-butyl ether, and a mixture thereof. Typically without isolation, metallated aryl A-4 is reacted with compound A-2 to give diaryl ketone A-5. The reaction is generally carried out at a low temperature, for example, −20 to −100° C. After removing the protecting group in A-5, the anilino nitrogen is derivatized to give target compound Formula I. Examples of protecting group include, but are not limited to —C(═O)Ot-Bu and —C(═O)t-Bu. The deprotection can be carried out with strong acids, such as HCl, HBr, trifluoroacetic acid, and $H_2SO_4$, or strong bases, such as NaOH, KOH, or CsOH.

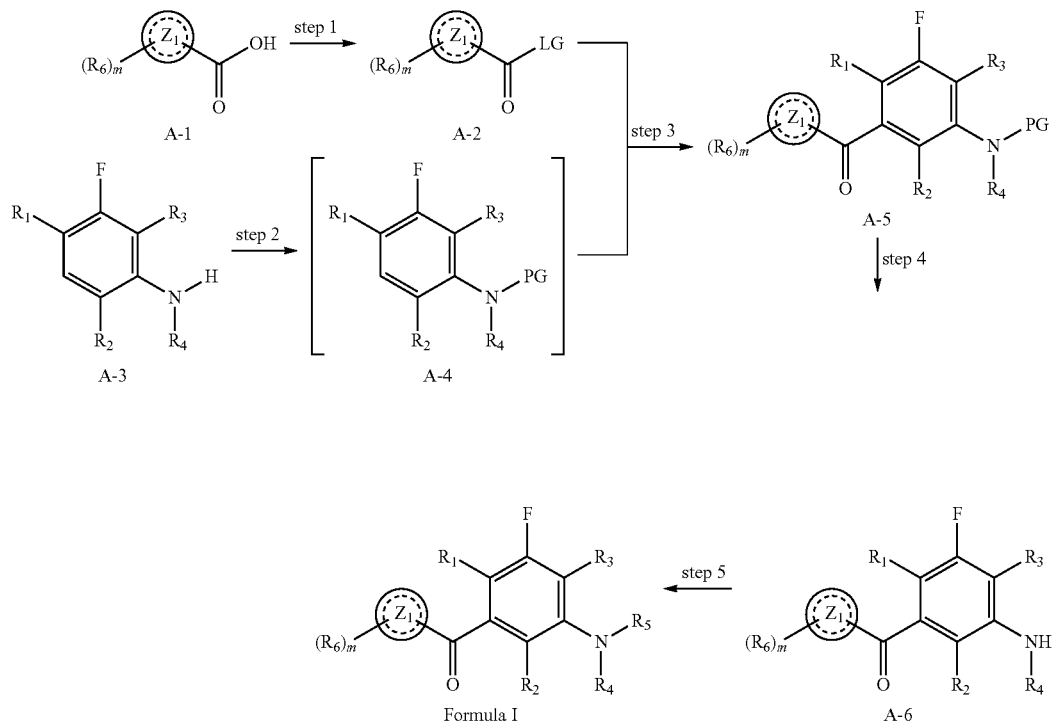

Scheme A

LG = Leaving Group
PG = Protecting Group

Scheme B

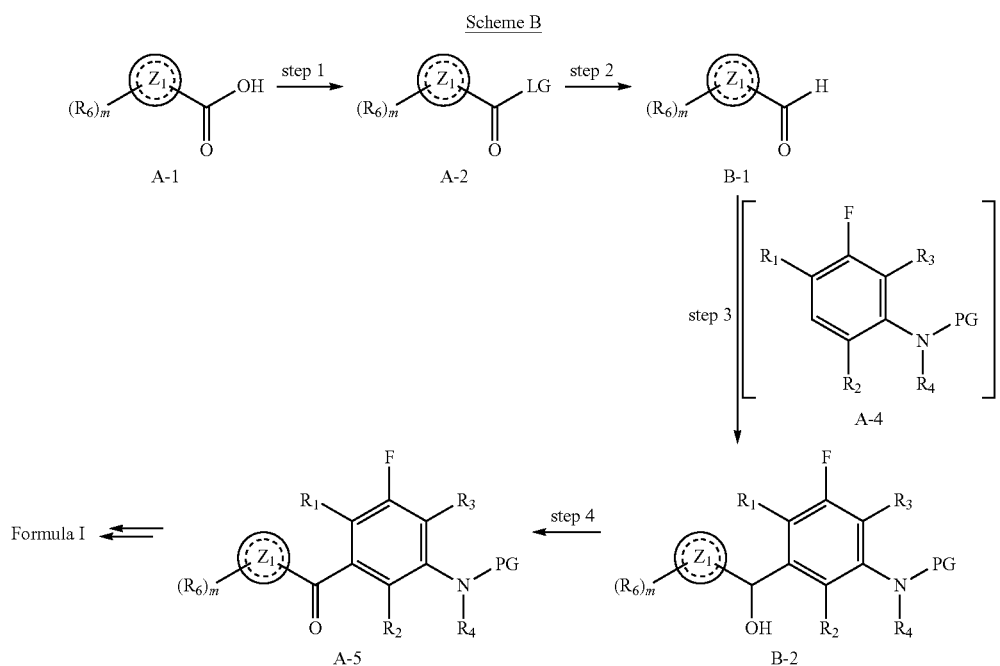

In Scheme B, A-2 is reduced to aldehyde B-1. Following similar procedures as described in Scheme A, B-1 is converted to alcohol B-2, which is then oxidized to ketone A-5.

C. Pharmaceutical Compositions and Formulations

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences,* Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Provided herein are pharmaceutical compositions comprising a compound of Formula I, and a pharmaceutically acceptable diluent(s), excipient(s), or carrier(s). In certain embodiments, the compounds described are administered as pharmaceutical compositions in which compounds of Formula I, are mixed with other active ingredients, as in combination therapy. Encompassed herein are all combinations of actives set forth in the combination therapies section below and throughout this disclosure. In specific embodiments, the pharmaceutical compositions include one or more compounds of Formula I.

A pharmaceutical composition, as used herein, refers to a mixture of a compound of Formula I, with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Formula I, provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of Formula I, is formulated in an aqueous solution. In specific embodiments, the aqueous solution is selected from, by way of example only, a physiologically compatible buffer, such as Hank's solution, Ringer's solution, or physiological saline buffer. In other embodiments, one or more compound of Formula I, is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including compounds of Formula I, are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of a compound of Formula I is formulated in a form suitable for parenteral injection as sterile suspension, solution or emulsion in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Formula I are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Formula I are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Formula I, is accomplished by means of iontophoretic patches and the like. In certain embodiments, transdermal patches provide controlled delivery of the compounds of Formula I. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Formula I, are formulated for administration by inhalation. Various forms suitable for administration by inhalation include, but are not limited to, aerosols, mists or powders. Pharmaceutical compositions of Formula I, are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of Formula I, are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of Formula I, are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Formula I, described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising at least one compound of Formula I, illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Formula I. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

D. Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

E. Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products Include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

F. Methods of Use

The chemical entities described herein are useful in the treatment, or in the preparation of a medicament for the treatment of various disorders. For example, compounds of Formula I are useful as inhibitors of protein kinases. In some embodiments, the chemical entities described herein are inhibitors of one or more kinases. For example, compounds of Formula I are inhibitors of A-Raf, B-Raf, C-Raf, KDR and of mutants of such kinases, including the B-Raf V600E mutant. Thus, without wishing to be bound by any particular theory, the compounds of Formula I are particularly useful for treating or lessening the severity of a disease, condition, or disorder where activation of one or more kinases, such as Raf kinases, which is implicated in the disease, condition, or disorder. When activation of Raf kinases is implicated in a particular disease, condition, or disorder, the disease, condition, or disorder may also be referred to as "Raf-mediated disease" or disease symptom. Accordingly, in another aspect, the present invention provides a method for treating or lessening the severity of a disease, condition, or disorder where activation or one or more of Raf kinases is implicated in the disease state.

In some embodiments, the chemical entities described herein are inhibitors of KDR. Inhibition of KDR leads to inhibition of VEGF-mediated angiogenesis. Accordingly, in another aspect, the present invention provides a method for treating or lessening the severity of a disease, condition, or disorder where diseases are characterized by abnormal angiogenesis.

The inhibition of kinases may be assayed in vitro, in vivo or in a cell line. In vitro assays include assays that determine inhibition of either the phosphorylation activity or ATPase activity of activated kinase. Alternate in vitro assays quantitate the ability of the inhibitor to bind to kinase Inhibitor binding may be measured by radiolabelling the inhibitor prior to binding, isolating the inhibitor, complex and determining the amount of radiolabel bound. Alternatively, inhibitor binding may be determined by running a competition experiment where new inhibitors are incubated with kinase bound to known radioligands. At 1 micro-molar concentration, one or more compounds of the present invention exhibits at least about 50%, 60%, 70, 80%, 90% or even higher inhibition of kinases including B-Raf, B-Raf V600E mutant and KDR.

The chemical entities described herein may be prepared in substantially pure form, typically by standard chromatographic methods, prior to formulation in a pharmaceutically acceptable form.

The chemical entities described herein may be used in treating a variety of cancers. Cancers that can be prevented and/or treated by the chemical entities, compositions, and methods described herein include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the chemical entities described herein are used for the treatment of cancers of the
i. digestive system including, without limitation, the esophagus, stomach, small intestine, colon (including colorectal), liver & intrahepatic bile duct, gallbladder & other biliary, pancreas, and other digestive organs;
ii. respiratory system, including without limitation, larynx, lung & bronchus, and other respiratory organs;
iii. skin;
iv. thyroid;
v. breast;
vi. genital system, including without limitation, uterine cervix, ovary, and prostate;
vii. urinary system, including without limitation, urinary bladder and kidney and renal pelvis; and
viii. oral cavity & pharynx, including without limitation, tongue, mouth, pharynx, and other oral cavity.

In some embodiments, the chemical entities described herein are used for the treatment of colon cancer, liver cancer, lung cancer, melanoma, thyroid cancer, breast cancer, ovarian cancer, and oral cancer.

The chemical entities described herein may also be used in conjunction with other well known therapeutic agents that are selected for their particular usefulness against the condition that is being treated. For example, the chemical entities described herein may be useful in combination with at least one additional anti-cancer and/or cytotoxic agents. Further, the chemical entities described herein may also be useful in combination with other inhibitors of parts of the signaling pathway that links cell surface growth factor receptors to nuclear signals initiating cellular proliferation.

Such known anti-cancer and/or cytotoxic agents that may be used in combination with the chemical entities described herein include:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolomide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3methylenedioxyanilino)-7-[2-(4-methylpiperazin-1-yl)ethoxy]-5-tetrahydropyran-4yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS- 354825; J. Med. Chem., 2004, 47, 66586661) and bosutinib (SK1-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (RI15777) and lonafarnib (SCH66336)), inhibitors of cell signalling through MEK and/or AKT kinases, c-kit inhibitors, abl kinase inhibitors, P13 kinase inhibitors, Plt3 kinase inhibitors, CSF-IR kinase inhibitors, IGF receptor (insulin like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4•{4-fluoro-2-methylindol-5-yloxy)-6-methoxy-7-(3pyrrolidin-1-ylpropoxy) quinazoline (AZD2171; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin));

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy; and (x) immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

In certain embodiments, the at least one chemical entity is administered in combination with one or more agents chosen from paclitaxel, bortezomib, dacarbazine, gemcitabine, trastuzumab, bevacizumab, capecitabine, docetaxel, erlotinib, aromatase inhibitors, such as AROMASIN™ (exemestane), and estrogen receptor inhibitors, such as FASLODEX™ (fulvestrant).

When a chemical entity described herein is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one chemical entity is administered to a mammal undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the chemical entity, such as including, e.g., from about 1 mg to about 1000 mg. The quantity of the at least one chemical entity in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one chemical entity used and the judgment of the attending clinician taking into consideration factors such as health, weight, and age. In combinational applications in which the at least one chemical entity described herein is not the sole active ingredient, it may be possible to administer lesser amounts of the at least one chemical entity and still have therapeutic or prophylactic effect.

In some embodiments, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one chemical entity. Thereafter, the dosage is increased by small amounts until the optimum effect under the circumstances is reached. For convenience, the total daily dosage may be divided and administered in portions during the day if desired.

The amount and frequency of administration of the at least one chemical entities described herein, and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one chemical entities described herein need not be administered in the same pharmaceutical composition as a chemotherapeutic agent, and may, because of different physical and chemical characteristics, be administered by a different route. For example, the chemical entities/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemical entity (and where appropriate, chemotherapeutic agent and/or radiation) will depend upon the diagnosis of the attending physicians and their judgment of the condition of the subject and the appropriate treatment protocol.

The chemical entities described herein (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the chemical entity/composition.

In combinational applications and uses, the chemical entity/composition and the chemotherapeutic agent and/or radiation need not be administered simultaneously or essentially simultaneously, and the initial order of administration of the chemical entity/composition, and the chemotherapeutic agent and/or radiation, may not be important. Thus, the at least one chemical entity described herein may be administered first followed by the administration of the chemotherapeutic agent and/or radiation; or the chemotherapeutic agent and/or radiation may be administered first followed by the administration of the at least one chemical entity described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one chemical entity described herein followed, where determined advantageous, by the administration of the chemotherapeutic agent and/or radiation, and so on until the treatment protocol is complete.

Thus, in accordance with experience and knowledge, the practicing physician can modify each protocol for the administration of a chemical entity/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The following examples serve to more fully describe the manner of using the invention. These examples are presented for illustrative purposes and should not serve to limit the true scope of the invention.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Example 1: Preparation of N-(2,4,5-trifluoro-3-(quinoline-6-carbonyl)phenyl)propane-1-sulfonamide

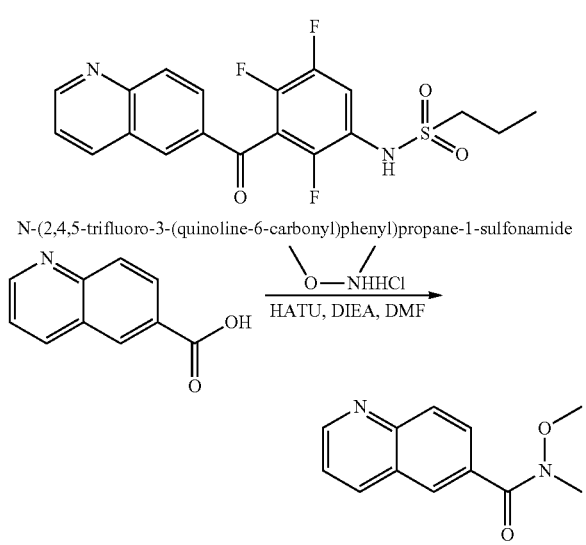

A mixture of quinoline-6-carboxylic acid (2.0 g, 11.6 mmol, 1.0 eq), N,O-dimethylhydroxylamine hydrochloride (1.34 g, 13.9 mmol, 1.2 eq), HATU (5.27 g, 13.9 mmol, 1.2 eq) and DIEA (8 mL, 46.2 mmol, 4.0 eq) in DMF (30 mL) was stirred at r.t. overnight. The mixture was concentrated and purified via flash column chromatography (PE/EA=2:1, v/v) to afford N-methoxy-N-methylquinoline-6-carboxamide (1.95 g, 78.1% yield).

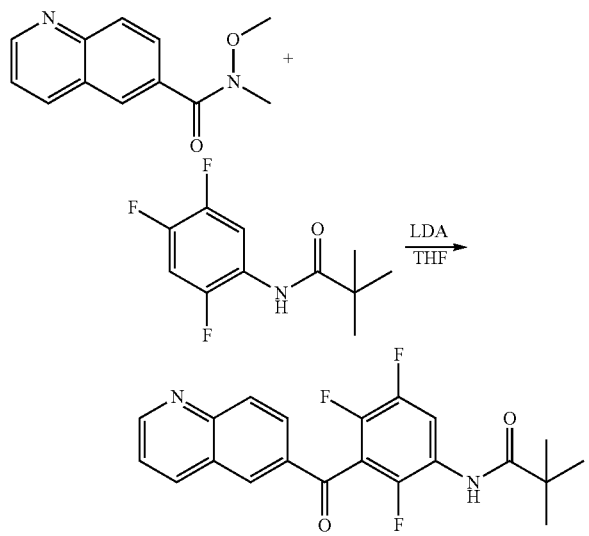

To a solution of N-(2,4,5-trifluorophenyl)pivalamide (2.54 g, 11 mmol, 1.1 eq.) in THF (80 mL) cooled at −78° C. was added LDA (22 mL, 2.2 mmol, 2.2 eq.) dropwise. The mixture was stirred at −78° C. for 30 min, then a solution of N-methoxy-N-methylquinoline-6-carboxamide (2.15 g, 10 mmol, 10 eq.) in THF (20 mL) was added dropwise. The mixture was stirred at −78° C. for 1 h, then quenched by the addition of aqueous NH$_4$Cl solution. The mixture was extracted with EA (50 mL×3). The combined organic layers were dried over Na$_2$SO$_4$, filtered, and concentrated. The resulting residue was purified via flash column chromatography (PE/EA=4/1, v/v) to afford N-(2,4,5-trifluoro-3-(quinoline-6-carbonyl)phenyl)pivalamide (1.33 g, 34% yield).

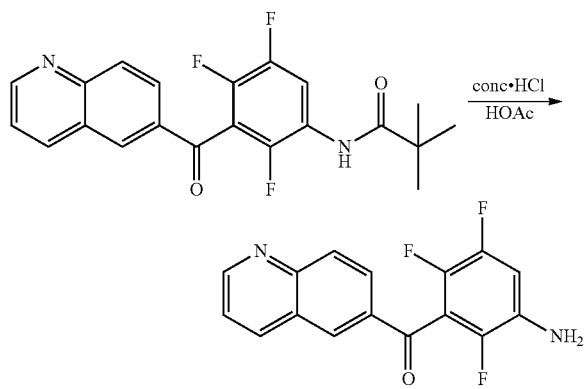

To a solution of N-(2,4,5-trifluoro-3-(quinoline-6-carbonyl)phenyl)pivalamide (1.33 g, 3.4 mmol) in HOAc (10 mL) was added conc.HCl (5 mL). The resulting mixture was stirred at 110° C. for 5 h, and cooled to r.t., basified to pH 10, and extracted with EA (20 mL×3). The combined organic layers were dried over Na$_2$SO$_4$, filtered and concentrated to afford (3-amino-2,5,6-trifluorophenyl)(quinolin-6-yl)methanone (700 mg, 68% yield).

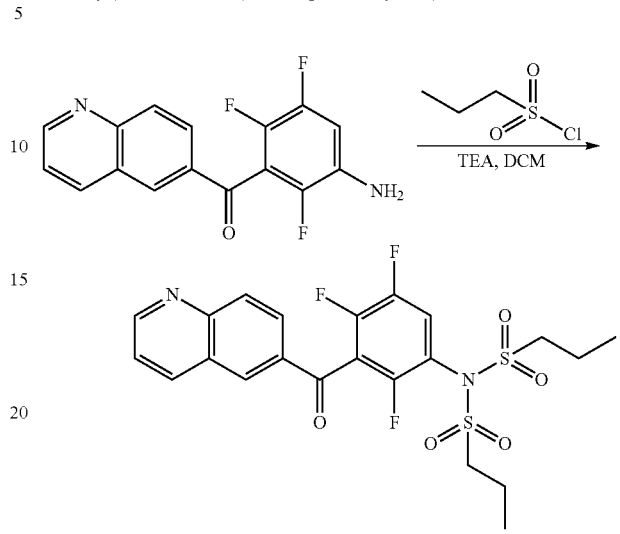

To a solution of (3-amino-2,5,6-trifluorophenyl)(quinolin-6-yl)methanone (50 mg, 0.17 mmol, 1 eq.) in DCM (30 mL) was added TEA (83 mg, 0.83 mmol, 5 eq.), followed by propane-1-sulfonyl chloride (70 mg, 0.49 mmol, 3 eq.). The resulting mixture was stirred at r.t. for 1 h, washed with water, and extracted with DCM (20 mL×3). The combined organic layers were dried over Na$_2$SO$_4$, filtered, and concentrated. The resulting residue was purified via flash column chromatography (PE/EA=2/1, v/v) to afford N-(propylsulfonyl)-N-(2,4,5-trifluoro-3-(quinoline-6-carbonyl)phenyl)propane-1-sulfonamide (86 mg, 100% yield).

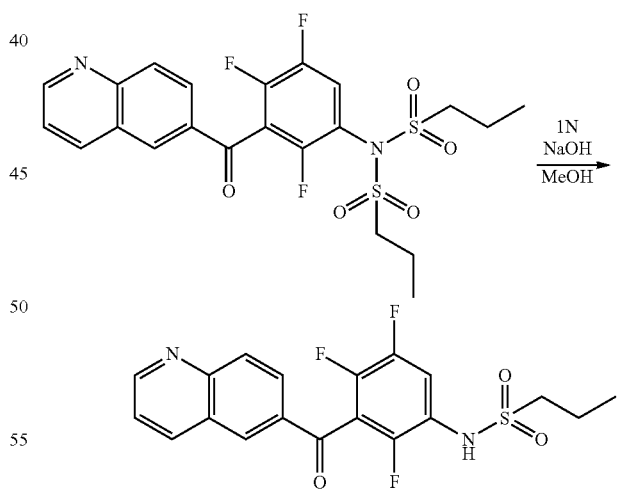

To a solution of N-(propylsulfonyl)-N-(2,4,5-trifluoro-3-(quinoline-6-carbonyl)phenyl)propane-1-sulfonamide (86 mg, 0.17 mmol, 1 eq.) in MeOH (5 mL) was added 1N NaOH (0.17 mL, 0.17 mmol, 1 eq.). The mixture was stirred at r.t. for 1 h, and concentrated. The resulting residue was purified via flash column chromatography (PE/EA=2/1, v/v) to afford N-(2,4,5-trifluoro-3-(quinoline-6-carbonyl)phenyl)propane-1-sulfonamide (64.5 mg, 95.5% yield). LRMS (M+H$^+$) m/z calculated 409.1, found 409.0. $^1$H NMR (CDCl₃, 300 MHz) δ 9.08-9.10 (dd, 1H), 8.25-8.31 (m, 4H), 7.68-7.77 (m, 1H), 7.52-7.57 (q, 1H), 6.64 (s, 1H), 3.14-3.19 (q, 2H), 1.88-1.96 (m, 2H), 1.07-1.12 (t, 3H).

Example 2: Preparation of 1-(3-fluorophenyl)-3-(2,4,5-trifluoro-3-(quinoline-6-carbonyl)phenyl)urea

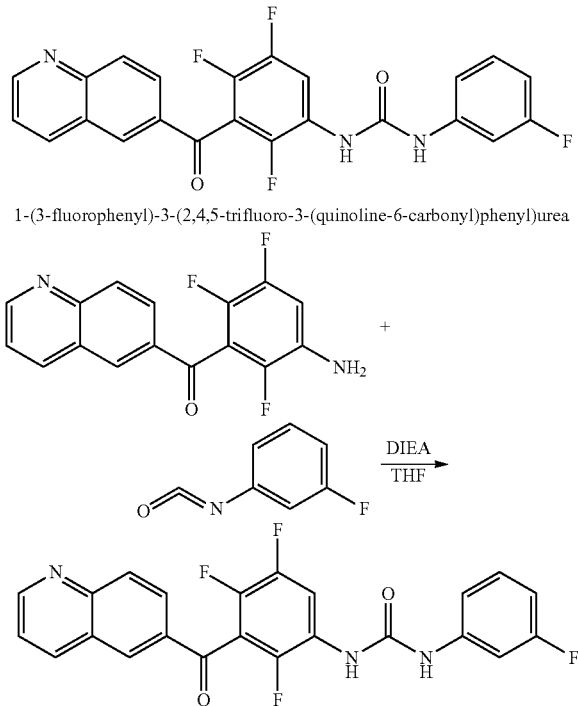

1-(3-fluorophenyl)-3-(2,4,5-trifluoro-3-(quinoline-6-carbonyl)phenyl)urea

To a solution of (3-amino-2,5,6-trifluorophenyl)(quinolin-6-yl)methanone (80 mg, 0.27 mmol, 1.0 eq.) in DCM (5 mL) were added TEA (0.2 mL, 1.35 mmol, 5.0 eq.) and 1-fluoro-3-isocyanatobenzene (70 mg, 0.54 mmol, 2 eq.). The mixture was stirred at rt for 1 h, and concentrated. The resulting residue was purified via flash column chromatography (PE/EA=2/1, v/v) to afford 1-(3-fluorophenyl)-3-(2,4,5-trifluoro-3-(quinoline-6-carbonyl)phenyl)urea (80 mg, 69% yield). LRMS (M+H⁺) m/z calculated 440.1, found 440.1. ¹H NMR (DMSO-d₆, 400 MHz) δ 9.35 (s, 1H), 9.09-9.10 (m, 1H), 8.96 (s, 1H), 8.67 (s, 1H), 8.63 (d, 1H), 8.41-8.48 (m, 1H), 8.28 (dd, 1H), 8.21 (d, 1H), 7.66-7.70 (m, 1H), 7.48-7.53 (m, 1H), 7.31-7.37 (m, 1H), 7.13 (dd, 1H), 6.82-6.87 (m, 1H).

Example 3: Preparation of 1-(4-fluorophenyl)-3-(2,4,5-trifluoro-3-(quinoline-6-carbonyl)phenyl)urea

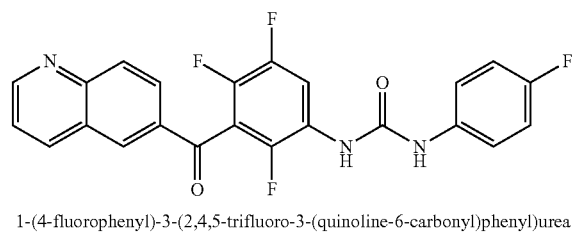 [SMILES: O=C(Nc1ccc(F)cc1)Nc1cc(F)c(F)c(C(=O)c2ccc3ncccc3c2)c1F]

1-(4-fluorophenyl)-3-(2,4,5-trifluoro-3-(quinoline-6-carbonyl)phenyl)urea 1-(4-Fluorophenyl)-3-(2,4,5-trifluoro-3-(quinoline-6-carbonyl)phenyl)urea (22.9 mg) was prepared as described for 1-(3-fluorophenyl)-3-(2,4,5-trifluoro-3-(quinoline-6-carbonyl)phenyl)urea. LRMS (M+H⁺) m/z calculated 440.1, found 440.0. ¹H NMR (DMSO-d₆, 400 MHz) δ 9.15 (s, 1H), 9.08-9.10 (m, 1H), 8.88 (s, 1H), 8.67 (s, 1H), 8.63 (d, 1H), 8.41-8.49 (m, 1H), 8.29 (dd, 1H), 8.21 (d, 1H), 7.66-7.70 (m, 1H), 7.45-7.49 (m, 2H), 7.13-7.18 (m, 2H).

Example 4: Preparation of 1-(3,4-difluorophenyl)-3-(2,4,5-trifluoro-3-(quinoline-6-carbonyl)phenyl)urea

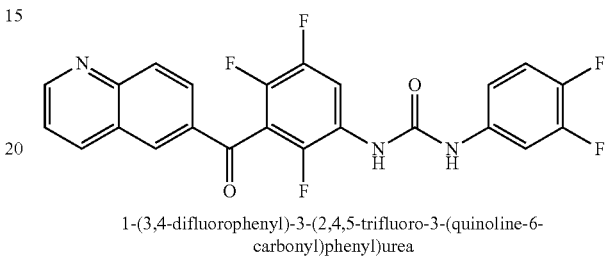

1-(3,4-difluorophenyl)-3-(2,4,5-trifluoro-3-(quinoline-6-carbonyl)phenyl)urea 1-(3,4-Difluorophenyl)-3-(2,4,5-trifluoro-3-(quinoline-6-carbonyl)phenyl)urea (26.1 mg) was prepared as described for 1-(3-fluorophenyl)-3-(2,4,5-trifluoro-3-(quinoline-6-carbonyl) phenyl)urea. LRMS (M+H⁺) m/z calculated 458.1, found 458.1. ¹H NMR (DMSO-d₆, 400 MHz) δ 9.37 (s, 1H), 9.09-9.11 (m, 1H), 8.98 (s, 1H), 8.68 (s, 1H), 8.63 (d, 1H), 8.39-8.47 (m, 1H), 8.29 (dd, 1H), 8.21 (d, 1H), 7.66-7.71 (m, 2H), 7.34-7.41 (m, 1H), 7.12-7.15 (m, 1H).

Example 5: Preparation of 1-(3,5-difluorophenyl)-3-(2,4,5-trifluoro-3-(quinoline-6-carbonyl)phenyl)urea

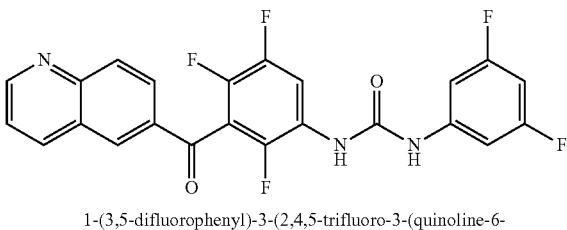

1-(3,5-difluorophenyl)-3-(2,4,5-trifluoro-3-(quinoline-6-carbonyl)phenyl)urea 1-(3,5-Difluorophenyl)-3-(2,4,5-trifluoro-3-(quinoline-6-carbonyl)phenyl)urea (80.6 mg) was prepared as described for 1-(3-fluorophenyl)-3-(2,4,5-trifluoro-3-(quinoline-6-carbonyl) phenyl)urea. LRMS (M+H⁺) m/z calculated 458.1, found 458.0. ¹H NMR (DMSO-d₆, 400 MHz) δ 9.55 (s, 1H), 9.09-9.11 (m, 1H), 9.06 (s, 1H), 8.68 (s, 1H), 8.63 (d, 1H), 8.38-8.46 (m, 1H), 8.29 (dd, 1H), 8.21 (d, 1H), 7.67-7.70 (m, 1H), 7.21 (d, 2H), 6.83-6.88 (m, 1H).

Example 6: Preparation of 3-fluoro-N-(2,4,5-trifluoro-3-(quinoline-6-carbonyl)phenyl)benzamide

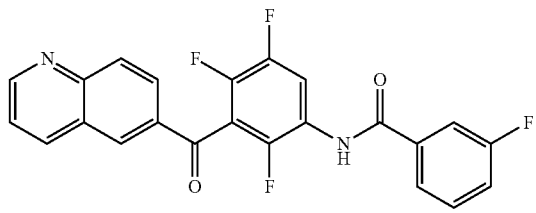

3-fluoro-N-(2,4,5-trifluoro-3-(quinoline-6-carbonyl)phenyl)benzamide

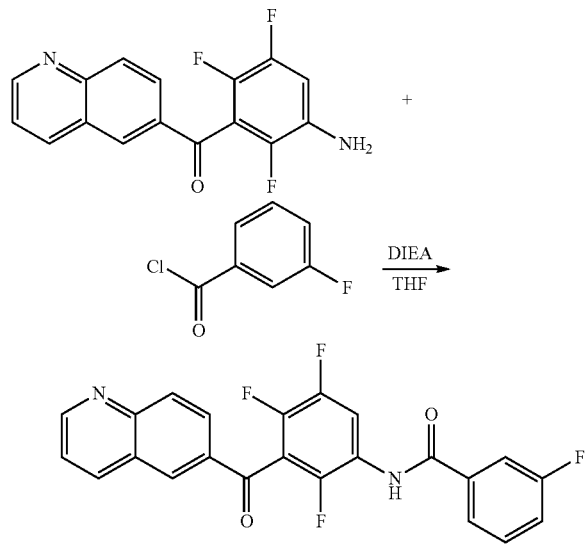

To a solution of (3-amino-2,5,6-trifluorophenyl)(quinolin-6-yl)methanone (50 mg, 0.17 mmol, 1.0 eq.) in THF (5 mL) were added DIEA (438 mg, 3.4 mmol, 20 eq.) and 3-fluorobenzoyl chloride (262 mg, 1.7 mmol, 10 eq.). The mixture was stirred at r.t. for 1 h, and concentrated. The resulting residue was purified via flash column chromatography (PE/EA=2/1, v/v) to afford 3-fluoro-N-(2,4,5-trifluoro-3-(quinoline-6-carbonyl)phenyl)benzamide (51 mg, 72.6% yield) LRMS (M+H$^+$) m/z calculated 425.1, found 425.0. $^1$H NMR (CDCl$_3$, 400 MHz) δ 9.06 (dd, 1H), 8.61-8.68 (m, 1H), 8.23-8.30 (m, 4H), 8.03 (s, 1H), 7.97-7.99 (m, 2H), 7.60-7.63 (m, 2H), 7.49-7.54 (m, 2H), 7.28-7.33 (m, 1H).

Example 7: Preparation of 4-fluoro-N-(2,4,5-trifluoro-3-(quinoline-6-carbonyl)phenyl)benzamide

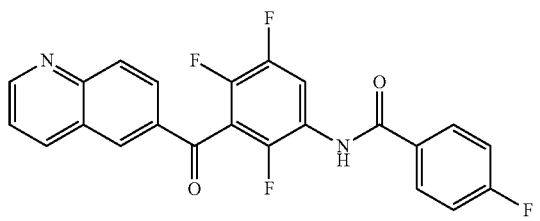

4-fluoro-N-(2,4,5-trifluoro-3-(quinoline-6-carbonyl)phenyl)benzamide

4-Fluoro-N-(2,4,5-trifluoro-3-(quinoline-6-carbonyl)phenyl)benzamide (29.9 mg) was prepared as described for 3-fluoro-N-(2,4,5-trifluoro-3-(quinoline-6-carbonyl) phenyl)benzamide. LRMS (M+H$^+$) m/z calculated 425.1, found 425.1. $^1$H NMR (CDCl3, 400 MHz) δ 9.06 (d, 1H), 8.61-8.68 (m, 1H), 8.23-8.30 (m, 4H), 7.99 (s, 1H), 7.89-7.92 (m, 2H), 7.51-7.54 (m, 1H), 7.18-7.26 (m, 2H).

Example 8: Preparation of 3,5-difluoro-N-(2,4,5-trifluoro-3-(quinoline-6-carbonyl)phenyl)benzamide

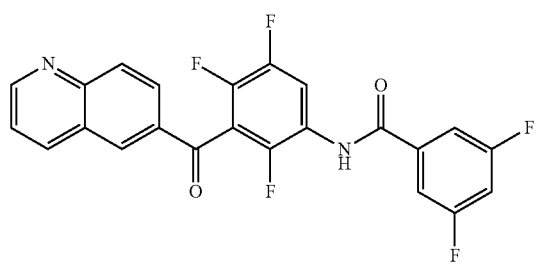

3,5-difluoro-N-(2,4,5-trifluoro-3-(quinoline-6-carbonyl)phenyl)benzamide 3,5-Difluoro-N-(2,4,5-trifluoro-3-(quinoline-6-carbonyl)phenyl)benzamide (55.4 mg) was prepared as described for 3-fluoro-N-(2,4,5-trifluoro-3-(quinoline-6-carbonyl) phenyl) benzamide. LRMS (M+H$^+$) m/z calculated 443.1, found 443.0. $^1$H NMR (CDCl3, 400 MHz) δ 9.06 (dd, 1H), 8.55-8.61 (m, 1H), 8.22-8.29 (m, 4H), 8.06 (s, 1H), 7.51-7.54 (m, 1H), 7.38-7.43 (m, 2H), 7.02-7.07 (m, 1H).

Example 9: Preparation of 3,4-difluoro-N-(2,4,5-trifluoro-3-(quinoline-6-carbonyl)phenyl)benzamide

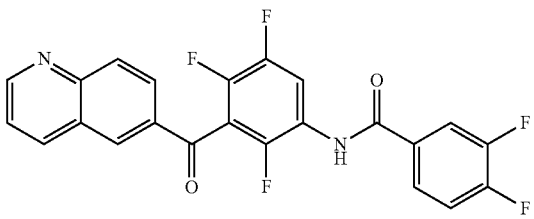

3,4-difluoro-N-(2,4,5-trifluoro-3-(quinoline-6-carbonyl)phenyl)benzamide 3,4-Difluoro-N-(2,4,5-trifluoro-3-(quinoline-6-carbonyl) phenyl)benzamide (55.4 mg) was prepared as described for 3-fluoro-N-(2,4,5-trifluoro-3-(quinoline-6-carbonyl) phenyl)benzamide. LRMS (M+H$^+$) m/z calculated 443.1, found 443.0. $^1$H NMR (CDCl3, 400 MHz) δ 8.99 (s, 1H), 8.52 (d, 1H), 8.20 (d, 4H), 7.95 (s, 1H), 7.70 (s, 1H), 7.55 (s, 1H), 7.45 (s, 1H), 7.19-7.24 (m, 1H).

Example 10: Preparation of N-(2,4,5-trifluoro-3-(quinazoline-6-carbonyl)phenyl) propane-1-sulfonamide

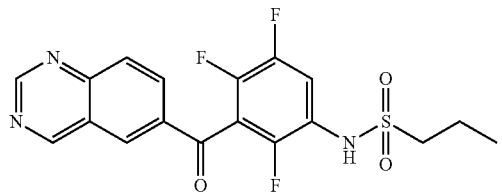

N-(2,4,5-trifluoro-3-(quinazoline-6-carbonyl)phenyl)propane-1-sulfonamide

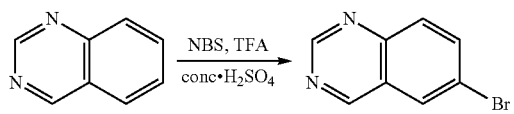

To a solution of quinazoline (13 g, 0.1 mol, 1.0 eq.) in TFA (50 mL) was added conc. H₂SO₄ (17 mL) slowly, followed by NBS (24 g, 0.135 mol, 1.35 eq.). The resulting mixture was stirred at r.t. for 12 h, then basified by the addition of Na₂CO₃ solution, extracted with DCM (200 mL*3). The combined organic layers were dried and purified via flash column chromatography (EA/PE=1/1, v/v) to afford 6-bromoquinazoline (11.6 g, 55.5% yield).

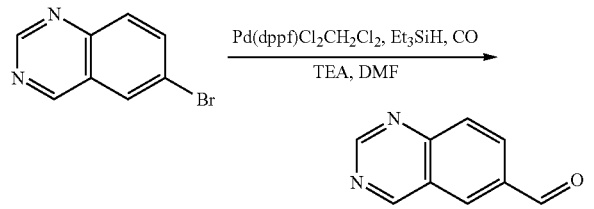

To a solution of 6-bromoquinazoline (11.6 g, 55 mmol, 1.0 eq.) in DMF (100 mL) was added TEA (38 mL, 0.28 mol, 5.0 eq.), Et₃SiH (35 mL, 0.22 mol, 4.0 eq) and Pd(dppf)Cl₂·CH₂Cl₂ (2.25 g, 2.76 mmol, 0.05 eq.). The resulting mixture was stirred in an autoclave under CO (1 MPa) at 90° C. for 12 h, then cooled and concentrated. The resulting residue was purified via flash column chromatography (EA/PE=1/1, v/v) to afford quinazoline-6-carbaldehyde (42.25 g, 25.8% yield).

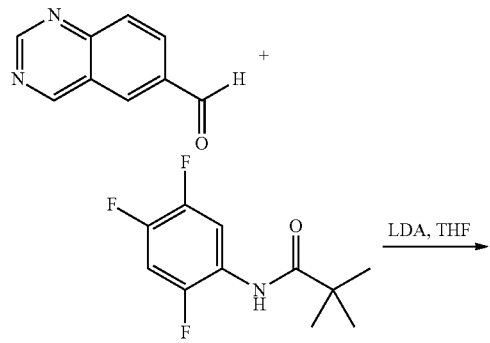

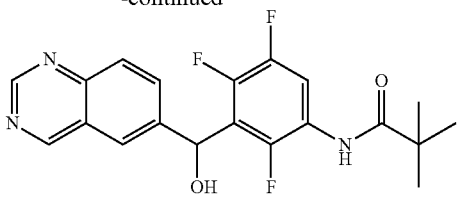

To a solution of N-(2,4,5-trifluorophenyl)pivalamide (2.54 g, 11 mmol, 1.1 eq.) in THF (80 mL) cooled at −78° C. was added LDA (22 mL, 22 mmol, 2.2 eq.) dropwise. The resulting mixture was stirred at −78° C. for 1 h, then was added a solution of quinazoline-6-carbaldehyde (1.58 g, 10 mol, 1.0 eq.) in THF (20 mL) dropwise. The resulting mixture was stirred at −78° C. for 1 h, then quenched by the addition of NH₄Cl solution. The mixture was extracted with EA (50 mL*3) and the combined organic layers were dried over Na₂SO₄ and concentrated. The residue was purified by flash column chromatography (MeOH/DCM=1/50, v/v) to afford N-(2,4,5-trifluoro-3-(hydroxy(quinazolin-6-yl)methyl)phenyl)pivalamide (715 mg, 18.4% yield).

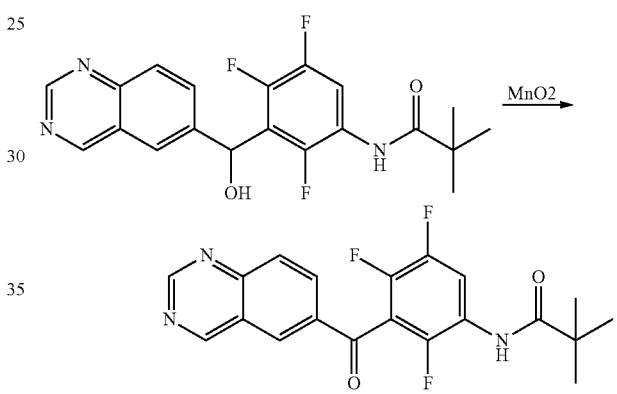

To a solution of N-(2,4,5-trifluoro-3-(hydroxy(quinazolin-6-yl) methyl) phenyl) pivalamide (715 mg, 1.94 mmol, 1.0 eq.) in DCM (20 mL) was added MnO₂ (800 mg, 9.2 mmol, 5.0 eq.). The resulting mixture was stirred at 50° C. overnight, then cooled and filtered. The filtrate was concentrated and the residue was purified by flash column chromatography (PE/EA=4/1, v/v) to afford N-(2,4,5-trifluoro-3-(quinazoline-6-carbonyl) phenyl) pivalamide (695 mg, 98% yield).

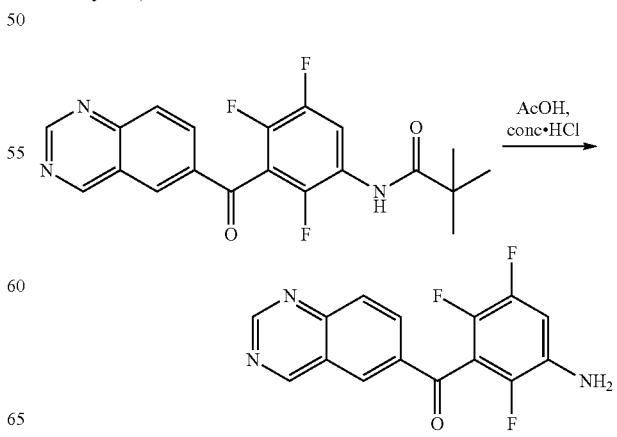

To a solution of N-(2,4,5-trifluoro-3-(quinazoline-6-carbonyl) phenyl) pivalamide (700 mg, 1.8 mmol, 1.0 eq.) in HOAc (5 mL) was added conc. HCl (5 mL). The mixture was stirred at 110° C. for 4 h, then poured onto ice. The mixture was adjusted to pH=10 by the addition of 1N NaOH aqueous solution, extracted with DCM (20 mL*3). The combined organic layers were dried over Na$_2$SO$_4$ and concentrated. The residue was purified by flash column chromatography (PE/EA=1/1, v/v) to afford ((3-amino-2,5,6-trifluorophenyl)(quinazolin-6-yl)methanone as yellow solid (60 mg, 11% yield).

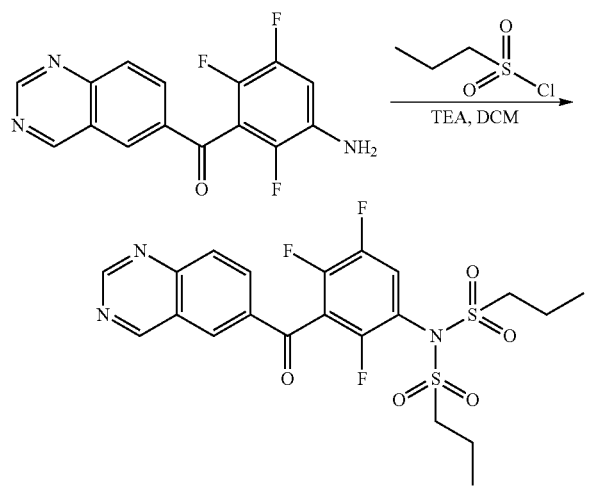

To a solution of ((3-amino-2,5,6-trifluorophenyl)(quinazolin-6-yl)methanone (60 mg, 0.2 mmol, 1 eq.) in DCM (10 mL) was added TEA (404 mg, 4 mmol, 20 eq.), followed by propane-1-sulfonyl chloride (285 mg, 2 mmol, 10 eq.). After the resulting mixture was stirred at r.t. for 1 h, then washed with water and extracted with DCM (20 mL*3). The combined organic layers were dried over Na$_2$SO$_4$, filtered and concentrated. The residue was purified via flash column chromatography (PE/EA=1/1, v/v) to afford N-(propylsulfonyl)-N-(2,4,5-trifluoro-3-(quinazoline-6-carbonyl)phenyl)propane-1-sulfonamide (35 mg, 34% yield).

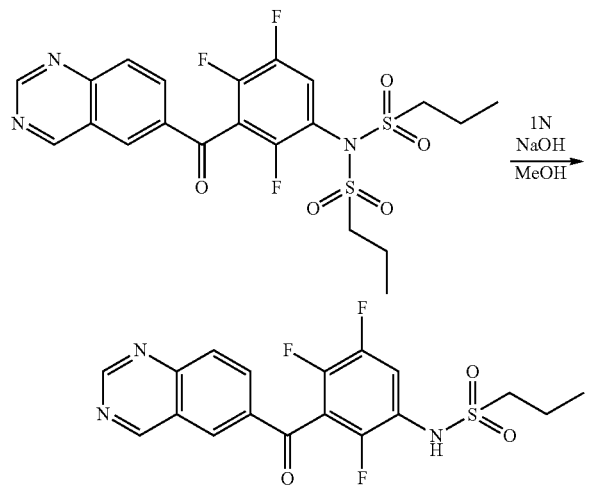

To a solution of N-(propylsulfonyl)-N-(2,4,5-trifluoro-3-(quinazoline-6-carbonyl)phenyl)propane-1-sulfonamide (35 mg, 0.07 mmol, 1 eq.) in MeOH (5 mL) was added 1N NaOH aqueous solution (0.07 mL, 0.07 mmol, 1 eq.). The resulting mixture was stirred at r.t. for 1 h, then concentrated. The residue was purified via flash column chromatography (PE/EA=1/3, v/v) to afford N-(2,4,5-trifluoro-3-(quinazoline-6-carbonyl)phenyl)propane-1-sulfonamide (12.2 mg, 44% yield). LRMS (M−H$^+$) m/z calculated 408.1, found 407.8. $^1$H NMR (CDCl$_3$, 400 MHz) δ 9.53 (s, 1H), 9.47 (s, 1H), 8.46 (dd, 1H), 8.37 (s, 1H), 8.21 (d, 1H), 7.70-7.77 (m, 1H), 6.61 (d, 1H), 3.15-3.18 (m, 2H), 1.89-1.94 (m, 2H), 1.09 (t, 3H).

Example 11: Inhibitory Activity Against BRAF and BRAF V600E

Inhibitory activities of compounds against BRAF or BRAF V600E were measured by Invitrogen using Z'-LYTE® Method as briefly described in the following.

4× Test compounds are dissolved in 1% DMSO. Kinase reaction mixture consists of 0.09-0.34 ng B-Raf (or 0.002-0.006 ng BRAF V600E), 1× inactive MAP2K1 (MEK1)/inactive MAPK1 (ERK2), and 2 μM Ser/Thr 03 in 50 mM HEPES pH 7.5, 0.01% BRIJ-35, 10 mM MgCl2, 1 mM EGTA. ATP solutions are diluted to a 4×ATP working concentration in Kinase Buffer (50 mM HEPES pH 7.5, 0.01% BRIJ-35, 10 mM MgCl2, 1 mM EGTA).

Reaction starts by 30-second shaking of mixture consisting of 2.5 μL 4× test compound, 2.5 μL 2× kinase reaction mixture and 2.5 μL 4×ATP Solution on Bar-coded Corning, low volume NBS, black 384-well plate (Corning Cat. #3676). Then the mixture is incubated for 60-minute at room temperature for the kinase reaction, followed by addition of 5 μL of a 1:1024 dilution of development reagent A and 30-second plate shake. The mixture is then incubated for another 60-minute at room temperature for development reaction. Finally fluorescence is read by plate reader. Table 2 shows % inhibition at 1 μM of several compounds of the invention using Z'-LYTE® method. The scale utilized in Table 2 is as follows: +++ more than 89% inhibition; ++ between 70% and 89% inhibition; and + less than 70% inhibition.

TABLE 2

Biological activity of several illustrative compounds against BRAF and BRAF V600E

| Compound No. | BRAF | BRAF V600E |
|---|---|---|
| C001 | ++ | +++ |
| C002 |  | + |
| C003 | + | + |
| C004 |  | + |
| C005 |  | + |
| C006 | + | ++ |
| C007 |  | + |
| C008 | + | + |
| C009 |  | + |
| C010 | +++ | +++ |

Example 12. Inhibition of Cancer Cell Growth by Compounds Using MTT or MTS Assay A375 (human melanoma cell, BRAF V600E Mutant), A549 (adenocarcinomic human alveolar basal epithelial cell) and Colo-205 (human colon carcinoma cell) were purchased from ATCC (American Type Culture Collection, Manassas, Va.). All cell lines were maintained in RPMI 1640

(Hyclone) or DMEM (Hyclone) supplemented with 10% fetal bovine serum (FBS, Hyclone), glutamine (2 mM, Hyclone), and antibiotics (penicillin 100 U/mL and streptomycin 50 μg/mL) at 37° C. in a humidified atmosphere of 5% $CO_2$ in air.

To test $IC_{50}$ of inhibition of individual compounds against each cell line, A375, A549 and Colo-205 cells were first plated in 96-well plates at densities of 2000-4000 cells/well. Cells were then incubated to allow cells to adhere and grow for 24 h. Cells were then treated with a series of concentrations of compounds for 72 h. The highest concentration of compounds was 20 μM. Cells were then removed from the incubator and medium was removed by inverting and tapping the plates. 100 μL of MTT (0.5 mg/ml) or 10 μL or MTS was added to each well followed by an incubated at 37° C. for 4 h. Then MTT was removed and 200 μL of DMSO was added to each well, followed by reading the ODs at 570 nm after a 5 second shaking cycle in a 96-well spectrophotometer. For MTS method, MTS was not removed, and the incubated solutions were directly put in a 96-well spectrophotometer for the reading of the ODs at 492 nm.

$IC_{50}$ was calculated by plotting the concentration of compound vs the percentage of inhibition in treated wells using GraphPad Prism 5. Table 3 shows $IC_{50}$ values of several compounds of the invention by MTT (A375 and A549 cells) or MTS (Colo-205 cells) assays. The scale utilized in Table 3 is as follows: +++ less than 1 μM; ++ between 1 μM and 5 μM; and + greater than 5 μM.

TABLE 3

$IC_{50}$ of several illustrative compounds in cancer cells

| Compound No. | A375 | A549 | Colo-205 |
|---|---|---|---|
| C001 | +++ | + | ++ |
| C002 | + | ++ | + |
| C003 | + | + | + |
| C004 | + | ++ | + |
| C005 | ++ | ++ | + |
| C006 | + | + | + |
| C007 | + | + | + |
| C008 | + | + | + |
| C009 | + | + | + |
| C010 | +++ | + | +++ |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A method of treating a cancer in a subject in need thereof, comprising administering to the subject a therapeutically effective amount of a compound of Formula I:

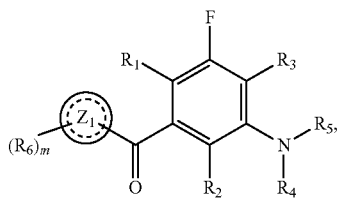

Formula I or a pharmaceutically acceptable salt thereof, wherein $Z_1$ is optionally substituted heteroaryl;

$R_1$, $R_2$, and $R_3$ are independently hydrogen, cyano, halo, hydroxy, azido, nitro, carboxy, sulfinyl, sulfanyl, sulfonyl, optionally substituted alkoxy, optionally substituted aryloxy, optionally substituted heteroaryloxy, optionally substituted heterocycloalkyloxy, optionally substituted alkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, or optionally substituted carbamimidoyl;

$R_4$ is hydrogen, optionally substituted alkyl, optionally substituted cycloalkyl, optionally substituted heterocycloalkyl, optionally substituted aryl, or optionally substituted heteroaryl;

$R_5$ is hydroxy, formyl, optionally substituted alkoxy, optionally substituted alkyl, optionally substituted cycloalkyl, optionally substituted heterocycloalkyl, optionally substituted aryl, optionally substituted heteroaryl, —$COR_7$, —$CO_2R_7$, —$CONR_7R_8$, —$C(NR_9)NR_7R_8$, or —$C(NCN)NR_7R_8$, where $R_7$ is optionally substituted alkyl, optionally substituted cycloalkyl, optionally substituted heterocycloalkyl, optionally substituted aryl, or optionally substituted heteroaryl; and $R_8$ and $R_9$ are independently hydrogen, optionally substituted alkyl, optionally substituted cycloalkyl, optionally substituted heterocycloalkyl, optionally substituted aryl, or optionally substituted heteroaryl; or $R_7$ and $R_8$ may be joined together with any intervening atoms to form an optionally substituted heterocycloalkyl ring; or $R_4$ and $R_5$ may be joined together with any intervening atoms to form an optionally substituted heterocycloalkyl ring;

for each occurrence, $R_6$ is independently hydrogen, cyano, halo, hydroxy, carboxy, azido, nitro, sulfonyl, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, or optionally substituted carbaminodoyl; and m is 0, 1, 2, 3, 4, 5 or 6;

provided that $Z_1$ is not quinoxalin-6-yl, wherein the cancer is skin cancer, lung cancer or colon cancer.

2. The method of claim 1, wherein the cancer is a cancer mediated by Raf.

3. The method of claim 1, wherein $R_1$, $R_2$, and $R_3$ are independently hydrogen, cyano, halo, optionally substituted alkoxy, optionally substituted alkyl, optionally substituted acyl, optionally substituted alkoxycarbonyl, optionally substituted aminocarbonyl, or optionally substituted aminosulfonyl.

4. The method of claim 3, wherein $R_1$, $R_2$, and $R_3$ are independently hydrogen, cyano, or halo.

5. The method of claim 1, wherein $R_1$ and $R_2$ are independently a halogen.

6. The method of claim 5, wherein $R_1$ and $R_2$ are fluoro.

7. The method of claim 1, wherein $R_4$ is selected from the group consisting of hydrogen, optionally substituted lower alkyl, optionally substituted aryl, and optionally substituted heteroaryl.

8. The method of claim 7, wherein $R_4$ is hydrogen.

9. The method of claim 1, wherein $R_5$ is $-COR_7$, $-CO_2R_7$, $-CONR_7R_8$, $-C(NR_9)NR_7R_8$, or $-C(NCN)NR_7R_8$, and wherein $R_7$ is optionally substituted alkyl, optionally substituted cycloalkyl, optionally substituted heterocycloalkyl, optionally substituted aryl, or optionally substituted heteroaryl; and $R_8$ and $R_9$ are independently hydrogen, optionally substituted alkyl, optionally substituted cycloalkyl, optionally substituted heterocycloalkyl, optionally substituted aryl, or optionally substituted heteroaryl.

10. The method of claim 9, wherein $R_7$ is optionally substituted alkyl, optionally substituted aryl, or optionally substituted heteroaryl; and $R_8$ and $R_9$ are independently hydrogen or optionally substituted alkyl.

11. The method of claim 1, wherein $R_5$ is $COR_7$.

12. The method of claim 11, wherein $R_7$ is optionally substituted aryl.

13. The method of claim 1, wherein $R_7$ and $R_8$ are joined together with any intervening atoms to form an optionally substituted 4- to 8-membered heterocycloalkyl ring.

14. The method of claim 1, wherein $R_4$ and $R_5$ are joined together with any intervening atoms to form an optionally substituted 4- to 8-membered heterocycloalkyl ring.

15. The method of claim 1, wherein $Z_1$ is an optionally substituted bicyclic heteroaryl.

16. The method of claim 1, wherein $Z_1$ is 1,5-naphthyridin-2-yl, 1,7-naphthyridin-6-yl, 1H-pyrazolo[3,4-b]pyrazin-3-yl, 1H-pyrazolo[3,4-b]pyridin-3-yl, 5H-pyrrolo[2,3-b]pyrazin-7-yl, 7H-pyrrolo[2,3-c]pyridazin-5-yl, 7H-pyrrolo[2,3-d]pyrimidin-5-yl, benzo[d]oxazol-5-yl, benzo[d]oxazol-6-yl, benzo[d]thiazol-6-yl, oxazolo[5,4-b]pyridin-5-yl, pyrido[3,4-b]pyrazin-7-yl, quinazolin-6-yl, or quinolin-6-yl.

17. The method of claim 1, wherein $Z_1$ is an optionally substituted quinolinyl.

18. The method of claim 1, wherein $Z_1$ is an optionally substituted quinazolinyl.

19. The method of claim 1, wherein, for each occurrence, $R_6$ is independently hydrogen, cyano, halo, hydroxy, carboxy, optionally substituted alkoxy, optionally substituted aryloxy, optionally substituted alkoxycarbonyl, optionally substituted alkyl, optionally substituted aryl, optionally substituted heteroaryl, optionally substituted amino, optionally substituted acyl, optionally substituted aminocarbonyl, or optionally substituted aminosulfonyl.

20. The method of claim 1, wherein, for each occurrence, $R_6$ is independently hydrogen, cyano, optionally substituted alkoxy, optionally substituted aryloxy, optionally substituted amino, optionally substituted alkyl, optionally substituted heterocycloalkyl, optionally substituted aryl, or optionally substituted heteroaryl.

21. The method of claim 1, wherein m is 0, 1, 2 or 3.

22. The method of claim 1, wherein the compound is selected from the group consisting of:
- 1-(3-fluoro-5-(quinoline-6-carbonyl)phenyl)-3-(3-fluorophenyl)urea,
- 1-(3-fluoro-5-(3-methylquinoline-6-carbonyl)phenyl)-3-(3-fluorophenyl)urea,
- 1-(3-(3-cyanoquinoline-6-carbonyl)-5-fluorophenyl)-3-(3-fluorophenyl)urea,
- 1-(3-fluoro-5-(3-methoxyquinoline-6-carbonyl)phenyl)-3-(3-fluorophenyl)urea,
- 1-(3-fluoro-5-(3-morpholinoquinoline-6-carbonyl)phenyl)-3-(3-fluorophenyl)urea,
- 1-(3,4-difluorophenyl)-3-(3-fluoro-5-(3-morpholinoquinoline-6-carbonyl)phenyl)urea,
- 1-(3-fluoro-5-(3-morpholinoquinoline-6-carbonyl)phenyl)-3-(4-fluorophenyl)urea,
- 1-(4-chlorophenyl)-3-(3-fluoro-5-(3-morpholinoquinoline-6-carbonyl)phenyl)urea,
- 1-(3-chlorophenyl)-3-(3-fluoro-5-(3-morpholinoquinoline-6-carbonyl)phenyl)urea,
- 1-(4-chloro-3-(trifluoromethyl)phenyl)-3-(3-fluoro-5-(3-morpholinoquinoline-6-carbonyl)phenyl)urea,
- 1-(3-fluoro-5-(3-(pyrrolidin-1-yl)quinoline-6-carbonyl)phenyl)-3-(3-fluorophenyl)urea,
- 1-(3-fluoro-5-(3-(piperazin-1-yl)quinoline-6-carbonyl)phenyl)-3-(3-fluorophenyl)urea,
- 1-(3,4-difluorophenyl)-3-(3-fluoro-5-(3-(piperazin-1-yl)quinoline-6-carbonyl)phenyl)urea,
- 1-(3-fluoro-5-(3-(piperazin-1-yl)quinoline-6-carbonyl)phenyl)-3-(4-fluorophenyl)urea,
- 1-(4-chlorophenyl)-3-(3-fluoro-5-(3-(piperazin-1-yl)quinoline-6-carbonyl)phenyl)urea,
- 1-(3-fluoro-5-(3-(pyridin-3-yl)quinoline-6-carbonyl)phenyl)-3-(3-fluorophenyl)urea,
- 1-(3-fluoro-5-(3-((2-hydroxyethyl)amino)quinoline-6-carbonyl)phenyl)-3-(3-fluorophenyl)urea,
- 1-(3-fluoro-5-(3-(2-hydroxyethoxy)quinoline-6-carbonyl)phenyl)-3-(3-fluorophenyl)urea,
- 1-(3-(3-(1H-pyrazol-4-yl)quinoline-6-carbonyl)-5-fluorophenyl)-3-(3-fluorophenyl)urea,
- 1-(3-(3-(1H-imidazol-1-yl)quinoline-6-carbonyl)-5-fluorophenyl)-3-(3-fluorophenyl)urea,
- 1-(3-fluoro-5-(quinazoline-6-carbonyl)phenyl)-3-(3-fluorophenyl)urea,
- 1-(3-fluoro-5-(quinazoline-6-carbonyl)phenyl)-3-(4-fluorophenyl)urea,
- 1-(3,4-difluorophenyl)-3-(3-fluoro-5-(quinazoline-6-carbonyl)phenyl)urea,
- 1-(3-fluoro-5-(1,7-naphthyridine-6-carbonyl)phenyl)-3-(3-fluorophenyl)urea,
- 1-(3,4-difluorophenyl)-3-(3-fluoro-5-(1,7-naphthyridine-6-carbonyl)phenyl)urea,
- 1-(3-fluoro-5-(3-morpholino-1,7-naphthyridine-6-carbonyl)phenyl)-3-(3-fluorophenyl)urea,
- 1-(3,4-difluorophenyl)-3-(3-fluoro-5-(3-morpholino-1,7-naphthyridine-6-carbonyl)phenyl)urea,
- 1-(3-fluoro-5-(pyrido[3,4-b]pyrazine-7-carbonyl)phenyl)-3-(3-fluorophenyl)urea,
- 1-(3-fluoro-5-(pyrido[3,4-b]pyrazine-7-carbonyl)phenyl)-3-(4-fluorophenyl)urea,
- 1-(3-fluoro-5-(2-morpholinopyrido[3,4-b]pyrazine-7-carbonyl)phenyl)-3-(4-fluorophenyl)urea, 1-(3-fluoro-5-(2-morpholinopyrido[3,4-b]pyrazine-7-carbonyl)phenyl)-3-(3-fluorophenyl)urea,
1-(3-fluoro-5-(1,5-naphthyridine-2-carbonyl)phenyl)-3-(3-fluorophenyl)urea,
1-(3-fluoro-5-(7-morpholino-1,5-naphthyridine-2-carbonyl)phenyl)-3-(3-fluorophenyl)urea,
1-(3-(benzo[d]oxazole-6-carbonyl)-5-fluorophenyl)-3-(3-fluorophenyl)urea,
1-(3-(benzo[d]oxazole-5-carbonyl)-5-fluorophenyl)-3-(3-fluorophenyl)urea,
1-(3-(benzo[d]thiazole-6-carbonyl)-5-fluorophenyl)-3-(3-fluorophenyl)urea,
1-(3-(3a,7a-dihydro-1H-pyrazolo[3,4-b]pyridine-3-carbonyl)-5-fluorophenyl)-3-(3-fluorophenyl)urea,
1-(3-(7,7a-dihydro-4aH-pyrrolo[2,3-d]pyrimidine-5-carbonyl)-5-fluorophenyl)-3-(3-fluorophenyl)urea,
1-(3-(5,7a-dihydro-4aH-pyrrolo[2,3-b]pyrazine-7-carbonyl)-5-fluorophenyl)-3-(3-fluorophenyl)urea,
1-(3-(3a,7a-dihydro-1H-pyrazolo[3,4-b]pyrazine-3-carbonyl)-5-fluorophenyl)-3-(3-fluorophenyl)urea,
1-(3-(7,7a-dihydro-4aH-pyrrolo[2,3-c]pyridazine-5-carbonyl)-5-fluorophenyl)-3-(3-fluorophenyl)urea,
1-(2,5-difluoro-3-(quinoline-6-carbonyl)phenyl)-3-(3-fluorophenyl)urea,
1-(2,5-difluoro-3-(3-methylquinoline-6-carbonyl)phenyl)-3-(3-fluorophenyl)urea,
1-(3-(3-cyanoquinoline-6-carbonyl)-2,5-difluorophenyl)-3-(3-fluorophenyl)urea,
1-(2,5-difluoro-3-(3-methoxyquinoline-6-carbonyl)phenyl)-3-(3-fluorophenyl)urea,
1-(2,5-difluoro-3-(3-morpholinoquinoline-6-carbonyl)phenyl)-3-(3-fluorophenyl)urea,
1-(2,5-difluoro-3-(3-morpholinoquinoline-6-carbonyl)phenyl)-3-(3,4-difluorophenyl)urea,
1-(2,5-difluoro-3-(3-morpholinoquinoline-6-carbonyl)phenyl)-3-(4-fluorophenyl)urea,
1-(4-chlorophenyl)-3-(2,5-difluoro-3-(3-morpholinoquinoline-6-carbonyl)phenyl)urea,
1-(3-chlorophenyl)-3-(2,5-difluoro-3-(3-morpholinoquinoline-6-carbonyl)phenyl)urea,
1-(4-chloro-3-(trifluoromethyl)phenyl)-3-(2,5-difluoro-3-(3-morpholinoquinoline-6-carbonyl)phenyl)urea,
1-(2,5-difluoro-3-(3-(pyrrolidin-1-yl)quinoline-6-carbonyl)phenyl)-3-(3-fluorophenyl)urea,
1-(2,5-difluoro-3-(3-(piperazin-1-yl)quinoline-6-carbonyl)phenyl)-3-(3-fluorophenyl)urea,
1-(2,5-difluoro-3-(3-(piperazin-1-yl)quinoline-6-carbonyl)phenyl)-3-(3,4-difluorophenyl)urea,
1-(2,5-difluoro-3-(3-(piperazin-1-yl)quinoline-6-carbonyl)phenyl)-3-(4-fluorophenyl)urea,
1-(4-chlorophenyl)-3-(2,5-difluoro-3-(3-(piperazin-1-yl)quinoline-6-carbonyl)phenyl)urea,
1-(2,5-difluoro-3-(3-(pyridin-3-yl)quinoline-6-carbonyl)phenyl)-3-(3-fluorophenyl)urea,
1-(2,5-difluoro-3-(3-((2-hydroxyethyl)amino)quinoline-6-carbonyl)phenyl)-3-(3-fluorophenyl)urea,
1-(2,5-difluoro-3-(3-(2-hydroxyethoxy)quinoline-6-carbonyl)phenyl)-3-(3-fluorophenyl)urea,
1-(3-(3-(1H-pyrazol-4-yl)quinoline-6-carbonyl)-2,5-difluorophenyl)-3-(3-fluorophenyl)urea,
1-(3-(3-(1H-imidazol-1-yl)quinoline-6-carbonyl)-2,5-difluorophenyl)-3-(3-fluorophenyl)urea,
1-(2,5-difluoro-3-(quinazoline-6-carbonyl)phenyl)-3-(3-fluorophenyl)urea,
1-(2,5-difluoro-3-(quinazoline-6-carbonyl)phenyl)-3-(4-fluorophenyl)urea,
1-(2,5-difluoro-3-(quinazoline-6-carbonyl)phenyl)-3-(3,4-difluorophenyl)urea,
1-(2,5-difluoro-3-(1,7-naphthyridine-6-carbonyl)phenyl)-3-(3-fluorophenyl)urea,
1-(2,5-difluoro-3-(1,7-naphthyridine-6-carbonyl)phenyl)-3-(3,4-difluorophenyl)urea,
1-(2,5-difluoro-3-(3-morpholino-1,7-naphthyridine-6-carbonyl)phenyl)-3-(3-fluorophenyl)urea,
1-(2,5-difluoro-3-(3-morpholino-1,7-naphthyridine-6-carbonyl)phenyl)-3-(3,4-difluorophenyl)urea,
1-(2,5-difluoro-3-(pyrido[3,4-b]pyrazine-7-carbonyl)phenyl)-3-(3-fluorophenyl)urea,
1-(2,5-difluoro-3-(pyrido[3,4-b]pyrazine-7-carbonyl)phenyl)-3-(4-fluorophenyl)urea,
1-(2,5-difluoro-3-(2-morpholinopyrido[3,4-b]pyrazine-7-carbonyl)phenyl)-3-(4-fluorophenyl)urea,
1-(2,5-difluoro-3-(2-morpholinopyrido[3,4-b]pyrazine-7-carbonyl)phenyl)-3-(3-fluorophenyl)urea,
1-(2,5-difluoro-3-(1,5-naphthyridine-2-carbonyl)phenyl)-3-(3-fluorophenyl)urea,
1-(2,5-difluoro-3-(7-morpholino-1,5-naphthyridine-2-carbonyl)phenyl)-3-(3-fluorophenyl)urea,
1-(3-(benzo[d]oxazole-6-carbonyl)-2,5-difluorophenyl)-3-(3-fluorophenyl)urea,
1-(3-(benzo[d]oxazole-5-carbonyl)-2,5-difluorophenyl)-3-(3-fluorophenyl)urea,
1-(3-(benzo[d]thiazole-6-carbonyl)-2,5-difluorophenyl)-3-(3-fluorophenyl)urea,
1-(3-(3a,7a-dihydro-1H-pyrazolo[3,4-b]pyridine-3-carbonyl)-2,5-difluorophenyl)-3-(3-fluorophenyl)urea,
1-(3-(7,7a-dihydro-4aH-pyrrolo[2,3-d]pyrimidine-5-carbonyl)-2,5-difluorophenyl)-3-(3-fluorophenyl)urea,
1-(3-(5,7a-dihydro-4aH-pyrrolo[2,3-b]pyrazine-7-carbonyl)-2,5-difluorophenyl)-3-(3-fluorophenyl)urea,
1-(3-(3a,7a-dihydro-1H-pyrazolo[3,4-b]pyrazine-3-carbonyl)-2,5-difluorophenyl)-3-(3-fluorophenyl)urea,
1-(3-(7,7a-dihydro-4aH-pyrrolo[2,3-c]pyridazine-5-carbonyl)-2,5-difluorophenyl)-3-(3-fluorophenyl)urea,
1-(3,4-difluoro-5-(quinoline-6-carbonyl)phenyl)-3-(3-fluorophenyl)urea,
1-(3-chlorophenyl)-3-(3,4-difluoro-5-(quinoline-6-carbonyl)phenyl)urea,
1-(4-chloro-3-fluorophenyl)-3-(3,4-difluoro-5-(quinoline-6-carbonyl)phenyl)urea,
1-(3-chloro-4-fluorophenyl)-3-(3,4-difluoro-5-(quinoline-6-carbonyl)phenyl)urea,
1-(4-chlorophenyl)-3-(3,4-difluoro-5-(quinoline-6-carbonyl)phenyl)urea,
1-(3,4-difluoro-5-(quinoline-6-carbonyl)phenyl)-3-(4-fluorophenyl)urea,
1-(3,4-difluoro-5-(quinoline-6-carbonyl)phenyl)-3-(3,4-difluorophenyl)urea,
1-(4-chloro-3-(trifluoromethyl)phenyl)-3-(3,4-difluoro-5-(quinoline-6-carbonyl)phenyl)urea,
1-(3,4-difluoro-5-(3-methylquinoline-6-carbonyl)phenyl)-3-(3-fluorophenyl)urea,
1-(3-(3-cyanoquinoline-6-carbonyl)-4,5-difluorophenyl)-3-(3-fluorophenyl)urea,
1-(3,4-difluoro-5-(3-methoxyquinoline-6-carbonyl)phenyl)-3-(3-fluorophenyl)urea,
1-(3,4-difluoro-5-(3-morpholinoquinoline-6-carbonyl)phenyl)-3-(3-fluorophenyl)urea,
1-(3,4-difluoro-5-(3-morpholinoquinoline-6-carbonyl)phenyl)-3-(3,4-difluorophenyl)urea,
1-(3,4-difluoro-5-(3-morpholinoquinoline-6-carbonyl)phenyl)-3-(4-fluorophenyl)urea, 1-(4-chlorophenyl)-3-(3,4-difluoro-5-(3-morpholinoquinoline-6-carbonyl)phenyl)urea,
1-(3-chlorophenyl)-3-(3,4-difluoro-5-(3-morpholinoquinoline-6-carbonyl)phenyl)urea,
1-(4-chloro-3-(trifluoromethyl)phenyl)-3-(3,4-difluoro-5-(3-morpholinoquinoline-6-carbonyl)phenyl)urea,
1-(3,4-difluoro-5-(3-(pyrrolidin-1-yl)quinoline-6-carbonyl)phenyl)-3-(3-fluorophenyl)urea,
1-(3,4-difluoro-5-(3-(piperazin-1-yl)quinoline-6-carbonyl)phenyl)-3-(3-fluorophenyl)urea,
1-(3,4-difluoro-5-(3-(piperazin-1-yl)quinoline-6-carbonyl)phenyl)-3-(3,4-difluorophenyl)urea,
1-(3,4-difluoro-5-(3-(piperazin-1-yl)quinoline-6-carbonyl)phenyl)-3-(4-fluorophenyl)urea,
1-(4-chlorophenyl)-3-(3,4-difluoro-5-(3-(piperazin-1-yl)quinoline-6-carbonyl)phenyl)urea,
1-(3,4-difluoro-5-(3-(pyridin-3-yl)quinoline-6-carbonyl)phenyl)-3-(3-fluorophenyl)urea,
1-(3,4-difluoro-5-(3-((2-hydroxyethyl)amino)quinoline-6-carbonyl)phenyl)-3-(3-fluorophenyl)urea,
1-(3,4-difluoro-5-(3-(2-hydroxyethoxy)quinoline-6-carbonyl)phenyl)-3-(3-fluorophenyl)urea,
1-(3-(3-(1H-pyrazol-4-yl)quinoline-6-carbonyl)-4,5-difluorophenyl)-3-(3-fluorophenyl)urea,
1-(3-(3-(1H-imidazol-1-yl)quinoline-6-carbonyl)-4,5-difluorophenyl)-3-(3-fluorophenyl)urea,
1-(3,4-difluoro-5-(quinazoline-6-carbonyl)phenyl)-3-(3-fluorophenyl)urea,
1-(3,4-difluoro-5-(quinazoline-6-carbonyl)phenyl)-3-(4-fluorophenyl)urea,
1-(4-chlorophenyl)-3-(3,4-difluoro-5-(quinazoline-6-carbonyl)phenyl)urea,
1-(3,4-difluoro-5-(quinazoline-6-carbonyl)phenyl)-3-(3,4-difluorophenyl)urea,
1-(4-chloro-3-fluorophenyl)-3-(3,4-difluoro-5-(quinazoline-6-carbonyl)phenyl)urea,
1-(4-chloro-3-(trifluoromethyl)phenyl)-3-(3,4-difluoro-5-(quinazoline-6-carbonyl)phenyl)urea,
1-(3-chloro-4-fluorophenyl)-3-(3,4-difluoro-5-(quinazoline-6-carbonyl)phenyl)urea,
1-(3,4-difluoro-5-(1,7-naphthyridine-6-carbonyl)phenyl)-3-(3-fluorophenyl)urea,
1-(3,4-difluoro-5-(1,7-naphthyridine-6-carbonyl)phenyl)-3-(3,4-difluorophenyl)urea,
1-(3,4-difluoro-5-(3-morpholino-1,7-naphthyridine-6-carbonyl)phenyl)-3-(3-fluorophenyl)urea,
1-(3,4-difluoro-5-(3-morpholino-1,7-naphthyridine-6-carbonyl)phenyl)-3-(3,4-difluorophenyl)urea,
1-(3,4-difluoro-5-(pyrido[3,4-b]pyrazine-7-carbonyl)phenyl)-3-(3-fluorophenyl)urea,
1-(3,4-difluoro-5-(pyrido[3,4-b]pyrazine-7-carbonyl)phenyl)-3-(4-fluorophenyl)urea,
1-(3,4-difluoro-5-(2-morpholinopyrido[3,4-b]pyrazine-7-carbonyl)phenyl)-3-(4-fluorophenyl)urea,
1-(3,4-difluoro-5-(2-morpholinopyrido[3,4-b]pyrazine-7-carbonyl)phenyl)-3-(3-fluorophenyl)urea,
1-(3,4-difluoro-5-(1,5-naphthyridine-2-carbonyl)phenyl)-3-(3-fluorophenyl)urea,
1-(3,4-difluoro-5-(7-morpholino-1,5-naphthyridine-2-carbonyl)phenyl)-3-(3-fluorophenyl)urea,
1-(3-(benzo[d]oxazole-6-carbonyl)-4,5-difluorophenyl)-3-(3-fluorophenyl)urea,
1-(3-(benzo[d]oxazole-5-carbonyl)-4,5-difluorophenyl)-3-(3-fluorophenyl)urea,
1-(3-(benzo[d]thiazole-6-carbonyl)-4,5-difluorophenyl)-3-(3-fluorophenyl)urea,
1-(3-(3a,7a-dihydro-1H-pyrazolo[3,4-b]pyridine-3-carbonyl)-4,5-difluorophenyl)-3-(3-fluorophenyl)urea,
1-(3-(7,7a-dihydro-4aH-pyrrolo[2,3-d]pyrimidine-5-carbonyl)-4,5-difluorophenyl)-3-(3-fluorophenyl)urea,
1-(3-(5,7a-dihydro-4aH-pyrrolo[2,3-b]pyrazine-7-carbonyl)-4,5-difluorophenyl)-3-(3-fluorophenyl)urea,
1-(3-(3a,7a-dihydro-1H-pyrazolo[3,4-b]pyrazine-3-carbonyl)-4,5-difluorophenyl)-3-(3-fluorophenyl)urea,
1-(3-(7,7a-dihydro-4aH-pyrrolo[2,3-c]pyridazine-5-carbonyl)-4,5-difluorophenyl)-3-(3-fluorophenyl)urea,
1-(3-fluorophenyl)-3-(2,4,5-trifluoro-3-(quinoline-6-carbonyl)phenyl)urea,
1-(3-fluorophenyl)-3-(2,4,5-trifluoro-3-(3-methylquinoline-6-carbonyl)phenyl)urea,
1-(3-(3-cyanoquinoline-6-carbonyl)-2,4,5-trifluorophenyl)-3-(3-fluorophenyl)urea,
1-(3-fluorophenyl)-3-(2,4,5-trifluoro-3-(3-methoxyquinoline-6-carbonyl)phenyl)urea,
1-(3-fluorophenyl)-3-(2,4,5-trifluoro-3-(3-morpholinoquinoline-6-carbonyl)phenyl)urea,
1-(3,4-difluorophenyl)-3-(2,4,5-trifluoro-3-(3-morpholinoquinoline-6-carbonyl)phenyl)urea,
1-(4-fluorophenyl)-3-(2,4,5-trifluoro-3-(3-morpholinoquinoline-6-carbonyl)phenyl)urea,
1-(4-chlorophenyl)-3-(2,4,5-trifluoro-3-(3-morpholinoquinoline-6-carbonyl)phenyl)urea,
1-(3-chlorophenyl)-3-(2,4,5-trifluoro-3-(3-morpholinoquinoline-6-carbonyl)phenyl)urea,
1-(4-chloro-3-(trifluoromethyl)phenyl)-3-(2,4,5-trifluoro-3-(3-morpholinoquinoline-6-carbonyl)phenyl)urea,
1-(3-fluorophenyl)-3-(2,4,5-trifluoro-3-(3-(pyrrolidin-1-yl)quinoline-6-carbonyl)phenyl)urea,
1-(3-fluorophenyl)-3-(2,4,5-trifluoro-3-(3-(piperazin-1-yl)quinoline-6-carbonyl)phenyl)urea,
1-(3,4-difluorophenyl)-3-(2,4,5-trifluoro-3-(3-(piperazin-1-yl)quinoline-6-carbonyl)phenyl)urea,
1-(4-fluorophenyl)-3-(2,4,5-trifluoro-3-(3-(piperazin-1-yl)quinoline-6-carbonyl)phenyl)urea,
1-(4-chlorophenyl)-3-(2,4,5-trifluoro-3-(3-(piperazin-1-yl)quinoline-6-carbonyl)phenyl)urea,
1-(3-fluorophenyl)-3-(2,4,5-trifluoro-3-(3-(pyridin-3-yl)quinoline-6-carbonyl)phenyl)urea,
1-(3-fluorophenyl)-3-(2,4,5-trifluoro-3-(3-((2-hydroxyethyl)amino)quinoline-6-carbonyl)phenyl)urea,
1-(3-fluorophenyl)-3-(2,4,5-trifluoro-3-(3-(2-hydroxyethoxy)quinoline-6-carbonyl)phenyl)urea,
1-(3-(3-(1H-pyrazol-4-yl)quinoline-6-carbonyl)-2,4,5-trifluorophenyl)-3-(3-fluorophenyl)urea,
1-(3-(3-(1H-imidazol-1-yl)quinoline-6-carbonyl)-2,4,5-trifluorophenyl)-3-(3-fluorophenyl)urea,
1-(3-fluorophenyl)-3-(2,4,5-trifluoro-3-(quinazoline-6-carbonyl)phenyl)urea,
1-(4-fluorophenyl)-3-(2,4,5-trifluoro-3-(quinazoline-6-carbonyl)phenyl)urea,
1-(3,4-difluorophenyl)-3-(2,4,5-trifluoro-3-(quinazoline-6-carbonyl)phenyl)urea,
1-(3-fluorophenyl)-3-(2,4,5-trifluoro-3-(1,7-naphthyridine-6-carbonyl)phenyl)urea,
1-(3,4-difluorophenyl)-3-(2,4,5-trifluoro-3-(1,7-naphthyridine-6-carbonyl)phenyl)urea,
1-(3-fluorophenyl)-3-(2,4,5-trifluoro-3-(3-morpholino-1,7-naphthyridine-6-carbonyl)phenyl)urea,
1-(3,4-difluorophenyl)-3-(2,4,5-trifluoro-3-(3-morpholino-1,7-naphthyridine-6-carbonyl)phenyl)urea,
1-(3-fluorophenyl)-3-(2,4,5-trifluoro-3-(pyrido[3,4-b]pyrazine-7-carbonyl)phenyl)urea, 1-(4-fluorophenyl)-3-(2,4,5-trifluoro-3-(pyrido[3,4-b]pyrazine-7-carbonyl)phenyl)urea,
1-(4-fluorophenyl)-3-(2,4,5-trifluoro-3-(2-morpholinopyrido[3,4-b]pyrazine-7-carbonyl)phenyl)urea,
1-(3-fluorophenyl)-3-(2,4,5-trifluoro-3-(2-morpholinopyrido[3,4-b]pyrazine-7-carbonyl)phenyl)urea,
1-(3-fluorophenyl)-3-(2,4,5-trifluoro-3-(1,5-naphthyridine-2-carbonyl)phenyl)urea,
1-(3-fluorophenyl)-3-(2,4,5-trifluoro-3-(7-morpholino-1,5-naphthyridine-2-carbonyl)phenyl)urea,
1-(3-(benzo[d]oxazole-6-carbonyl)-2,4,5-trifluorophenyl)-3-(3-fluorophenyl)urea,
1-(3-(benzo[d]oxazole-5-carbonyl)-2,4,5-trifluorophenyl)-3-(3-fluorophenyl)urea,
1-(3-(benzo[d]thiazole-6-carbonyl)-2,4,5-trifluorophenyl)-3-(3-fluorophenyl)urea,
1-(3-(3a,7a-dihydro-1H-pyrazolo[3,4-b]pyridine-3-carbonyl)-2,4,5-trifluorophenyl)-3-(3-fluorophenyl)urea,
1-(3-(7,7a-dihydro-4aH-pyrrolo[2,3-d]pyrimidine-5-carbonyl)-2,4,5-trifluorophenyl)-3-(3-fluorophenyl)urea,
1-(3-(5,7a-dihydro-4aH-pyrrolo[2,3-b]pyrazine-7-carbonyl)-2,4,5-trifluorophenyl)-3-(3-fluorophenyl)urea,
1-(3-(3a,7a-dihydro-1H-pyrazolo[3,4-b]pyrazine-3-carbonyl)-2,4,5-trifluorophenyl)-3-(3-fluorophenyl)urea,
1-(3-(7,7a-dihydro-4aH-pyrrolo[2,3-c]pyridazine-5-carbonyl)-2,4,5-trifluorophenyl)-3-(3-fluorophenyl)urea,
1-(4-fluorophenyl)-3-(2,4,5-trifluoro-3-(quinoline-6-carbonyl)phenyl)urea,
1-(3,4-difluorophenyl)-3-(2,4,5-trifluoro-3-(quinoline-6-carbonyl)phenyl)urea,
1-(3,5-difluorophenyl)-3-(2,4,5-trifluoro-3-(quinoline-6-carbonyl)phenyl)urea,
4-fluoro-N-(2,4,5-trifluoro-3-(quinoline-6-carbonyl)phenyl)benzamide,
3,5-difluoro-N-(2,4,5-trifluoro-3-(quinoline-6-carbonyl)phenyl)benzamide,
3,4-difluoro-N-(2,4,5-trifluoro-3-(quinoline-6-carbonyl)phenyl)benzamide,
3-fluoro-N-(3-fluoro-5-(quinoline-6-carbonyl)phenyl)benzamide,
3,4-difluoro-N-(3-fluoro-5-(quinoline-6-carbonyl)phenyl)benzamide,
4-fluoro-N-(3-fluoro-5-(quinoline-6-carbonyl)phenyl)benzamide,
3-chloro-N-(3-fluoro-5-(quinoline-6-carbonyl)phenyl)benzamide,
4-chloro-3-fluoro-N-(3-fluoro-5-(quinoline-6-carbonyl)phenyl)benzamide,
4-chloro-N-(3-fluoro-5-(quinoline-6-carbonyl)phenyl)-3-(trifluoromethyl)benzamide,
4-chloro-N-(3-fluoro-5-(quinoline-6-carbonyl)phenyl)benzamide,
3-fluoro-N-(3-fluoro-5-(3-methylquinoline-6-carbonyl)phenyl)benzamide,
N-(3-(3-cyanoquinoline-6-carbonyl)-5-fluorophenyl)-3-fluorobenzamide,
3-fluoro-N-(3-fluoro-5-(3-methoxyquinoline-6-carbonyl)phenyl)benzamide,
3-fluoro-N-(3-fluoro-5-(3-morpholinoquinoline-6-carbonyl)phenyl)benzamide,
3,4-difluoro-N-(3-fluoro-5-(3-morpholinoquinoline-6-carbonyl)phenyl)benzamide,
4-fluoro-N-(3-fluoro-5-(3-morpholinoquinoline-6-carbonyl)phenyl)benzamide,
4-chloro-N-(3-fluoro-5-(3-morpholinoquinoline-6-carbonyl)phenyl)benzamide,
3-chloro-N-(3-fluoro-5-(3-morpholinoquinoline-6-carbonyl)phenyl)benzamide,
4-chloro-N-(3-fluoro-5-(3-morpholinoquinoline-6-carbonyl)phenyl)-3-(trifluoromethyl)benzamide,
3-fluoro-N-(3-fluoro-5-(3-(pyrrolidin-1-yl)quinoline-6-carbonyl)phenyl)benzamide,
3-fluoro-N-(3-fluoro-5-(3-(piperazin-1-yl)quinoline-6-carbonyl)phenyl)benzamide,
3,4-difluoro-N-(3-fluoro-5-(3-(piperazin-1-yl)quinoline-6-carbonyl)phenyl)benzamide,
4-fluoro-N-(3-fluoro-5-(3-(piperazin-1-yl)quinoline-6-carbonyl)phenyl)benzamide,
4-chloro-N-(3-fluoro-5-(3-(piperazin-1-yl)quinoline-6-carbonyl)phenyl)benzamide,
3-fluoro-N-(3-fluoro-5-(3-(pyridin-3-yl)quinoline-6-carbonyl)phenyl)benzamide,
3-fluoro-N-(3-fluoro-5-(3-((2-hydroxyethyl)amino)quinoline-6-carbonyl)phenyl)benzamide,
3-fluoro-N-(3-fluoro-5-(3-(2-hydroxyethoxy)quinoline-6-carbonyl)phenyl)benzamide,
N-(3-(3-(1H-pyrazol-4-yl)quinoline-6-carbonyl)-5-fluorophenyl)-3-fluorobenzamide,
N-(3-(3-(1H-imidazol-1-yl)quinoline-6-carbonyl)-5-fluorophenyl)-3-fluorobenzamide,
3-fluoro-N-(3-fluoro-5-(quinazoline-6-carbonyl)phenyl)benzamide,
4-fluoro-N-(3-fluoro-5-(quinazoline-6-carbonyl)phenyl)benzamide,
3,4-difluoro-N-(3-fluoro-5-(quinazoline-6-carbonyl)phenyl)benzamide,
3-fluoro-N-(3-fluoro-5-(1,7-naphthyridine-6-carbonyl)phenyl)benzamide,
3,4-difluoro-N-(3-fluoro-5-(1,7-naphthyridine-6-carbonyl)phenyl)benzamide,
3-fluoro-N-(3-fluoro-5-(3-morpholino-1,7-naphthyridine-6-carbonyl)phenyl)benzamide,
3,4-difluoro-N-(3-fluoro-5-(3-morpholino-1,7-naphthyridine-6-carbonyl)phenyl)benzamide,
3-fluoro-N-(3-fluoro-5-(pyrido[3,4-b]pyrazine-7-carbonyl)phenyl)benzamide,
4-fluoro-N-(3-fluoro-5-(pyrido[3,4-b]pyrazine-7-carbonyl)phenyl)benzamide,
4-fluoro-N-(3-fluoro-5-(2-morpholinopyrido[3,4-b]pyrazine-7-carbonyl)phenyl)benzamide,
3-fluoro-N-(3-fluoro-5-(2-morpholinopyrido[3,4-b]pyrazine-7-carbonyl)phenyl)benzamide,
3-fluoro-N-(3-fluoro-5-(1,5-naphthyridine-2-carbonyl)phenyl)benzamide,
3-fluoro-N-(3-fluoro-5-(7-morpholino-1,5-naphthyridine-2-carbonyl)phenyl)benzamide,
N-(3-(benzo[d]oxazole-6-carbonyl)-5-fluorophenyl)-3-fluorobenzamide,
N-(3-(benzo[d]oxazole-5-carbonyl)-5-fluorophenyl)-3-fluorobenzamide,
N-(3-(benzo[d]thiazole-6-carbonyl)-5-fluorophenyl)-3-fluorobenzamide,
N-(3-(3a,7a-dihydro-1H-pyrazolo[3,4-b]pyridine-3-carbonyl)-5-fluorophenyl)-3-fluorobenzamide,
N-(3-(7,7a-dihydro-4aH-pyrrolo[2,3-d]pyrimidine-5-carbonyl)-5-fluorophenyl)-3-fluorobenzamide,
N-(3-(5,7a-dihydro-4aH-pyrrolo[2,3-b]pyrazine-7-carbonyl)-5-fluorophenyl)-3-fluorobenzamide,
N-(3-(3a,7a-dihydro-1H-pyrazolo[3,4-b]pyrazine-3-carbonyl)-5-fluorophenyl)-3-fluorobenzamide,
N-(3-(7,7a-dihydro-4aH-pyrrolo[2,3-c]pyridazine-5-carbonyl)-5-fluorophenyl)-3-fluorobenzamide, N-(2,5-difluoro-3-(quinoline-6-carbonyl)phenyl)-3-fluorobenzamide,
N-(2,5-difluoro-3-(3-methylquinoline-6-carbonyl)phenyl)-3-fluorobenzamide,
N-(3-(3-cyanoquinoline-6-carbonyl)-2,5-difluorophenyl)-3-fluorobenzamide,
N-(2,5-difluoro-3-(3-methoxyquinoline-6-carbonyl)phenyl)-3-fluorobenzamide,
N-(2,5-difluoro-3-(3-morpholinoquinoline-6-carbonyl)phenyl)-3-fluorobenzamide,
N-(2,5-difluoro-3-(3-morpholinoquinoline-6-carbonyl)phenyl)-3,4-difluorobenzamide,
N-(2,5-difluoro-3-(3-morpholinoquinoline-6-carbonyl)phenyl)-4-fluorobenzamide,
4-chloro-N-(2,5-difluoro-3-(3-morpholinoquinoline-6-carbonyl)phenyl)benzamide,
3-chloro-N-(2,5-difluoro-3-(3-morpholinoquinoline-6-carbonyl)phenyl)benzamide,
4-chloro-N-(2,5-difluoro-3-(3-morpholinoquinoline-6-carbonyl)phenyl)-3-(trifluoromethyl)benzamide,
N-(2,5-difluoro-3-(3-(pyrrolidin-1-yl)quinoline-6-carbonyl)phenyl)-3-fluorobenzamide,
N-(2,5-difluoro-3-(3-(piperazin-1-yl)quinoline-6-carbonyl)phenyl)-3-fluorobenzamide,
N-(2,5-difluoro-3-(3-(piperazin-1-yl)quinoline-6-carbonyl)phenyl)-3,4-difluorobenzamide,
N-(2,5-difluoro-3-(3-(piperazin-1-yl)quinoline-6-carbonyl)phenyl)-4-fluorobenzamide,
4-chloro-N-(2,5-difluoro-3-(3-(piperazin-1-yl)quinoline-6-carbonyl)phenyl)benzamide,
N-(2,5-difluoro-3-(3-(pyridin-3-yl)quinoline-6-carbonyl)phenyl)-3-fluorobenzamide,
N-(2,5-difluoro-3-(3-((2-hydroxyethyl)amino)quinoline-6-carbonyl)phenyl)-3-fluorobenzamide,
N-(2,5-difluoro-3-(3-(2-hydroxyethoxy)quinoline-6-carbonyl)phenyl)-3-fluorobenzamide,
N-(3-(3-(1H-pyrazol-4-yl)quinoline-6-carbonyl)-2,5-difluorophenyl)-3-fluorobenzamide,
N-(3-(3-(1H-imidazol-1-yl)quinoline-6-carbonyl)-2,5-difluorophenyl)-3-fluorobenzamide,
N-(2,5-difluoro-3-(quinazoline-6-carbonyl)phenyl)-3-fluorobenzamide,
N-(2,5-difluoro-3-(quinazoline-6-carbonyl)phenyl)-4-fluorobenzamide,
N-(2,5-difluoro-3-(quinazoline-6-carbonyl)phenyl)-3,4-difluorobenzamide,
N-(2,5-difluoro-3-(1,7-naphthyridine-6-carbonyl)phenyl)-3-fluorobenzamide,
N-(2,5-difluoro-3-(1,7-naphthyridine-6-carbonyl)phenyl)-3,4-difluorobenzamide,
N-(2,5-difluoro-3-(3-morpholino-1,7-naphthyridine-6-carbonyl)phenyl)-3-fluorobenzamide,
N-(2,5-difluoro-3-(3-morpholino-1,7-naphthyridine-6-carbonyl)phenyl)-3,4-difluorobenzamide,
N-(2,5-difluoro-3-(pyrido[3,4-b]pyrazine-7-carbonyl)phenyl)-3-fluorobenzamide,
N-(2,5-difluoro-3-(pyrido[3,4-b]pyrazine-7-carbonyl)phenyl)-4-fluorobenzamide,
N-(2,5-difluoro-3-(2-morpholinopyrido[3,4-b]pyrazine-7-carbonyl)phenyl)-4-fluorobenzamide,
N-(2,5-difluoro-3-(2-morpholinopyrido[3,4-b]pyrazine-7-carbonyl)phenyl)-3-fluorobenzamide,
N-(2,5-difluoro-3-(1,5-naphthyridine-2-carbonyl)phenyl)-3-fluorobenzamide,
N-(2,5-difluoro-3-(7-morpholino-1,5-naphthyridine-2-carbonyl)phenyl)-3-fluorobenzamide,
N-(3-(benzo[d]oxazole-6-carbonyl)-2,5-difluorophenyl)-3-fluorobenzamide,
N-(3-(benzo[d]oxazole-5-carbonyl)-2,5-difluorophenyl)-3-fluorobenzamide,
N-(3-(benzo[d]thiazole-6-carbonyl)-2,5-difluorophenyl)-3-fluorobenzamide,
N-(3-(3a,7a-dihydro-1H-pyrazolo[3,4-b]pyridine-3-carbonyl)-2,5-difluorophenyl)-3-fluorobenzamide,
N-(3-(7,7a-dihydro-4aH-pyrrolo[2,3-d]pyrimidine-5-carbonyl)-2,5-difluorophenyl)-3-fluorobenzamide,
N-(3-(5,7a-dihydro-4aH-pyrrolo[2,3-b]pyrazine-7-carbonyl)-2,5-difluorophenyl)-3-fluorobenzamide,
N-(3-(3a,7a-dihydro-1H-pyrazolo[3,4-b]pyrazine-3-carbonyl)-2,5-difluorophenyl)-3-fluorobenzamide,
N-(3-(7,7a-dihydro-4aH-pyrrolo[2,3-c]pyridazine-5-carbonyl)-2,5-difluorophenyl)-3-fluorobenzamide,
N-(3,4-difluoro-5-(quinoline-6-carbonyl)phenyl)-3-fluorobenzamide,
N-(3,4-difluoro-5-(quinoline-6-carbonyl)phenyl)-3,4-difluorobenzamide,
N-(3,4-difluoro-5-(quinoline-6-carbonyl)phenyl)-4-fluorobenzamide,
3-chloro-N-(3,4-difluoro-5-(quinoline-6-carbonyl)phenyl)benzamide,
4-chloro-N-(3,4-difluoro-5-(quinoline-6-carbonyl)phenyl)-3-fluorobenzamide,
4-chloro-N-(3,4-difluoro-5-(quinoline-6-carbonyl)phenyl)-3-(trifluoromethyl)benzamide,
4-chloro-N-(3,4-difluoro-5-(quinoline-6-carbonyl)phenyl)benzamide,
N-(3,4-difluoro-5-(3-methylquinoline-6-carbonyl)phenyl)-3-fluorobenzamide,
N-(3-(3-cyanoquinoline-6-carbonyl)-4,5-difluorophenyl)-3-fluorobenzamide,
N-(3,4-difluoro-5-(3-methoxyquinoline-6-carbonyl)phenyl)-3-fluorobenzamide,
N-(3,4-difluoro-5-(3-morpholinoquinoline-6-carbonyl)phenyl)-3-fluorobenzamide,
N-(3,4-difluoro-5-(3-morpholinoquinoline-6-carbonyl)phenyl)-3,4-difluorobenzamide,
N-(3,4-difluoro-5-(3-morpholinoquinoline-6-carbonyl)phenyl)-4-fluorobenzamide,
4-chloro-N-(3,4-difluoro-5-(3-morpholinoquinoline-6-carbonyl)phenyl)benzamide,
3-chloro-N-(3,4-difluoro-5-(3-morpholinoquinoline-6-carbonyl)phenyl)benzamide,
4-chloro-N-(3,4-difluoro-5-(3-morpholinoquinoline-6-carbonyl)phenyl)-3-(trifluoromethyl)benzamide,
N-(3,4-difluoro-5-(3-(pyrrolidin-1-yl)quinoline-6-carbonyl)phenyl)-3-fluorobenzamide,
N-(3,4-difluoro-5-(3-(piperazin-1-yl)quinoline-6-carbonyl)phenyl)-3-fluorobenzamide,
N-(3,4-difluoro-5-(3-(piperazin-1-yl)quinoline-6-carbonyl)phenyl)-3,4-difluorobenzamide,
N-(3,4-difluoro-5-(3-(piperazin-1-yl)quinoline-6-carbonyl)phenyl)-4-fluorobenzamide,
4-chloro-N-(3,4-difluoro-5-(3-(piperazin-1-yl)quinoline-6-carbonyl)phenyl)benzamide,
N-(3,4-difluoro-5-(3-(pyridin-3-yl)quinoline-6-carbonyl)phenyl)-3-fluorobenzamide,
N-(3,4-difluoro-5-(3-((2-hydroxyethyl)amino)quinoline-6-carbonyl)phenyl)-3-fluorobenzamide,
N-(3,4-difluoro-5-(3-(2-hydroxyethoxy)quinoline-6-carbonyl)phenyl)-3-fluorobenzamide,
N-(3-(3-(1H-pyrazol-4-yl)quinoline-6-carbonyl)-4,5-difluorophenyl)-3-fluorobenzamide, N-(3-(3-(1H-imidazol-1-yl)quinoline-6-carbonyl)-4,5-difluorophenyl)-3-fluorobenzamide,
N-(3,4-difluoro-5-(quinazoline-6-carbonyl)phenyl)-3-fluorobenzamide,
N-(3,4-difluoro-5-(quinazoline-6-carbonyl)phenyl)-4-fluorobenzamide,
N-(3,4-difluoro-5-(quinazoline-6-carbonyl)phenyl)-3,4-difluorobenzamide,
N-(3,4-difluoro-5-(1,7-naphthyridine-6-carbonyl)phenyl)-3-fluorobenzamide,
N-(3,4-difluoro-5-(1,7-naphthyridine-6-carbonyl)phenyl)-3,4-difluorobenzamide,
N-(3,4-difluoro-5-(3-morpholino-1,7-naphthyridine-6-carbonyl)phenyl)-3-fluorobenzamide,
N-(3,4-difluoro-5-(3-morpholino-1,7-naphthyridine-6-carbonyl)phenyl)-3,4-difluorobenzamide,
N-(3,4-difluoro-5-(pyrido[3,4-b]pyrazine-7-carbonyl)phenyl)-3-fluorobenzamide,
N-(3,4-difluoro-5-(pyrido[3,4-b]pyrazine-7-carbonyl)phenyl)-4-fluorobenzamide,
N-(3,4-difluoro-5-(2-morpholinopyrido[3,4-b]pyrazine-7-carbonyl)phenyl)-4-fluorobenzamide,
N-(3,4-difluoro-5-(2-morpholinopyrido[3,4-b]pyrazine-7-carbonyl)phenyl)-3-fluorobenzamide,
N-(3,4-difluoro-5-(1,5-naphthyridine-2-carbonyl)phenyl)-3-fluorobenzamide,
N-(3,4-difluoro-5-(7-morpholino-1,5-naphthyridine-2-carbonyl)phenyl)-3-fluorobenzamide,
N-(3-(benzo[d]oxazole-6-carbonyl)-4,5-difluorophenyl)-3-fluorobenzamide,
N-(3-(benzo[d]oxazole-5-carbonyl)-4,5-difluorophenyl)-3-fluorobenzamide,
N-(3-(benzo[d]thiazole-6-carbonyl)-4,5-difluorophenyl)-3-fluorobenzamide,
N-(3-(3a,7a-dihydro-1H-pyrazolo[3,4-b]pyridine-3-carbonyl)-4,5-difluorophenyl)-3-fluorobenzamide,
N-(3-(7,7a-dihydro-4aH-pyrrolo[2,3-d]pyrimidine-5-carbonyl)-4,5-difluorophenyl)-3-fluorobenzamide,
N-(3-(5,7a-dihydro-4aH-pyrrolo[2,3-b]pyrazine-7-carbonyl)-4,5-difluorophenyl)-3-fluorobenzamide,
N-(3-(3a,7a-dihydro-1H-pyrazolo[3,4-b]pyrazine-3-carbonyl)-4,5-difluorophenyl)-3-fluorobenzamide,
N-(3-(7,7a-dihydro-4aH-pyrrolo[2,3-c]pyridazine-5-carbonyl)-4,5-difluorophenyl)-3-fluorobenzamide,
3-fluoro-N-(2,4,5-trifluoro-3-(quinoline-6-carbonyl)phenyl)benzamide,
3-fluoro-N-(2,4,5-trifluoro-3-(3-methylquinoline-6-carbonyl)phenyl)benzamide,
N-(3-(3-cyanoquinoline-6-carbonyl)-2,4,5-trifluorophenyl)-3-fluorobenzamide,
3-fluoro-N-(2,4,5-trifluoro-3-(3-methoxyquinoline-6-carbonyl)phenyl)benzamide,
3-fluoro-N-(2,4,5-trifluoro-3-(3-morpholinoquinoline-6-carbonyl)phenyl)benzamide,
3,4-difluoro-N-(2,4,5-trifluoro-3-(3-morpholinoquinoline-6-carbonyl)phenyl)benzamide,
4-fluoro-N-(2,4,5-trifluoro-3-(3-morpholinoquinoline-6-carbonyl)phenyl)benzamide,
4-chloro-N-(2,4,5-trifluoro-3-(3-morpholinoquinoline-6-carbonyl)phenyl)benzamide,
3-chloro-N-(2,4,5-trifluoro-3-(3-morpholinoquinoline-6-carbonyl)phenyl)benzamide,
4-chloro-N-(2,4,5-trifluoro-3-(3-morpholinoquinoline-6-carbonyl)phenyl)-3-(trifluoromethyl)benzamide,
3-fluoro-N-(2,4,5-trifluoro-3-(3-(pyrrolidin-1-yl)quinoline-6-carbonyl)phenyl)benzamide,
3-fluoro-N-(2,4,5-trifluoro-3-(3-(piperazin-1-yl)quinoline-6-carbonyl)phenyl)benzamide,
3,4-difluoro-N-(2,4,5-trifluoro-3-(3-(piperazin-1-yl)quinoline-6-carbonyl)phenyl)benzamide,
4-fluoro-N-(2,4,5-trifluoro-3-(3-(piperazin-1-yl)quinoline-6-carbonyl)phenyl)benzamide,
4-chloro-N-(2,4,5-trifluoro-3-(3-(piperazin-1-yl)quinoline-6-carbonyl)phenyl)benzamide,
3-fluoro-N-(2,4,5-trifluoro-3-(3-(pyridin-3-yl)quinoline-6-carbonyl)phenyl)benzamide,
3-fluoro-N-(2,4,5-trifluoro-3-(3-((2-hydroxyethyl)amino)quinoline-6-carbonyl)phenyl)benzamide,
3-fluoro-N-(2,4,5-trifluoro-3-(3-(2-hydroxyethoxy)quinoline-6-carbonyl)phenyl)benzamide,
N-(3-(3-(1H-pyrazol-4-yl)quinoline-6-carbonyl)-2,4,5-trifluorophenyl)-3-fluorobenzamide,
N-(3-(3-(1H-imidazol-1-yl)quinoline-6-carbonyl)-2,4,5-trifluorophenyl)-3-fluorobenzamide,
3-fluoro-N-(2,4,5-trifluoro-3-(quinazoline-6-carbonyl)phenyl)benzamide,
4-fluoro-N-(2,4,5-trifluoro-3-(quinazoline-6-carbonyl)phenyl)benzamide,
3,4-difluoro-N-(2,4,5-trifluoro-3-(quinazoline-6-carbonyl)phenyl)benzamide,
3-fluoro-N-(2,4,5-trifluoro-3-(1,7-naphthyridine-6-carbonyl)phenyl)benzamide,
3,4-difluoro-N-(2,4,5-trifluoro-3-(1,7-naphthyridine-6-carbonyl)phenyl)benzamide,
3-fluoro-N-(2,4,5-trifluoro-3-(3-morpholino-1,7-naphthyridine-6-carbonyl)phenyl)benzamide,
3,4-difluoro-N-(2,4,5-trifluoro-3-(3-morpholino-1,7-naphthyridine-6-carbonyl)phenyl)benzamide,
3-fluoro-N-(2,4,5-trifluoro-3-(pyrido[3,4-b]pyrazine-7-carbonyl)phenyl)benzamide,
4-fluoro-N-(2,4,5-trifluoro-3-(pyrido[3,4-b]pyrazine-7-carbonyl)phenyl)benzamide,
4-fluoro-N-(2,4,5-trifluoro-3-(2-morpholinopyrido[3,4-b]pyrazine-7-carbonyl)phenyl)benzamide,
3-fluoro-N-(2,4,5-trifluoro-3-(2-morpholinopyrido[3,4-b]pyrazine-7-carbonyl)phenyl)benzamide,
3-fluoro-N-(2,4,5-trifluoro-3-(1,5-naphthyridine-2-carbonyl)phenyl)benzamide,
3-fluoro-N-(2,4,5-trifluoro-3-(7-morpholino-1,5-naphthyridine-2-carbonyl)phenyl)benzamide,
N-(3-(benzo[d]oxazole-6-carbonyl)-2,4,5-trifluorophenyl)-3-fluorobenzamide,
N-(3-(benzo[d]oxazole-5-carbonyl)-2,4,5-trifluorophenyl)-3-fluorobenzamide,
N-(3-(benzo[d]thiazole-6-carbonyl)-2,4,5-trifluorophenyl)-3-fluorobenzamide,
N-(3-(3a,7a-dihydro-1H-pyrazolo[3,4-b]pyridine-3-carbonyl)-2,4,5-trifluorophenyl)-3-fluorobenzamide,
N-(3-(7,7a-dihydro-4aH-pyrrolo[2,3-d]pyrimidine-5-carbonyl)-2,4,5-trifluorophenyl)-3-fluorobenzamide,
N-(3-(5,7a-dihydro-4aH-pyrrolo[2,3-b]pyrazine-7-carbonyl)-2,4,5-trifluorophenyl)-3-fluorobenzamide,
N-(3-(3a,7a-dihydro-1H-pyrazolo[3,4-b]pyrazine-3-carbonyl)-2,4,5-trifluorophenyl)-3-fluorobenzamide, and
N-(3-(7,7a-dihydro-4aH-pyrrolo[2,3-c]pyridazine-5-carbonyl)-2,4,5-trifluorophenyl)-3-fluorobenzamide.

\* \* \* \* \*